US012747234B2

(12) United States Patent
Feng et al.

(10) Patent No.: US 12,747,234 B2
(45) Date of Patent: Sep. 29, 2026

(54) KINASE INHIBITORS FOR THE TREATMENT OF NEURODEGENERATIVE DISEASES

(71) Applicants: Ohio State Innovation Foundation, Columbus, OH (US); REACTION BIOLOGY CORPORATION, Malvern, PA (US)

(72) Inventors: Yangbo Feng, Malvern, PA (US); Sung Ok Yoon, Columbus, OH (US)

(73) Assignees: Ohio State Innovation Foundation, Columbus, OH (US); REACTION BIOLOGY CORPORATION, Malvern, PA (US)

( * ) Notice: Subject to any disclaimer, the term of this patent is extended or adjusted under 35 U.S.C. 154(b) by 552 days.

(21) Appl. No.: 18/249,147

(22) PCT Filed: Oct. 12, 2021

(86) PCT No.: PCT/US2021/054540
§ 371 (c)(1),
(2) Date: Apr. 14, 2023

(87) PCT Pub. No.: WO2022/081552
PCT Pub. Date: Apr. 21, 2022

(65) Prior Publication Data

US 2024/0246942 A1 Jul. 25, 2024

Related U.S. Application Data

(60) Provisional application No. 63/092,333, filed on Oct. 15, 2020.

(51) Int. Cl.
*C07D 409/14* (2006.01)
*A61K 31/4155* (2006.01)
*C07D 405/14* (2006.01)

(52) U.S. Cl.
CPC ........ *C07D 409/14* (2013.01); *A61K 31/4155* (2013.01)

(58) Field of Classification Search
CPC .. C07D 405/14; C07D 409/04; C07D 409/14; A61K 31/4155; A61P 25/28
USPC ........................................ 548/365.7; 514/407
See application file for complete search history.

(56) References Cited

U.S. PATENT DOCUMENTS

2014/0309210 A1 10/2014 Burch et al.

FOREIGN PATENT DOCUMENTS

WO 2010091310 A1 8/2010

OTHER PUBLICATIONS

International Search Report and Written Opinion for PCT/US2021/054540 mailed Jan. 5, 2022.

Pubchem, Substance Record for SID 333069152. Available Date: Apr. 11, 2018. [retrieved on 1-46 Dec. 2, 2021]. Retrieved from the Internet: <https://pubchern.ncbi .nlm.nih .gov/substance/333069152> entire document.

Pubchem, Substance Record for SID 277803627. Available Date: Jan. 12, 2016. [retrieved on Dec. 2, 2021]. Retrieved from the Internet: <https://pubchern.ncbi.nlm.nih.gov/substance/277803627>. entire document.

Feng et al., Thiophene-Pyrazolourea Derivatives as Potent, Orally Bioavailable, and Isofonn-Selective JNK3 Inhibitors, ACS Medicinal Chemistry Letters, vol. 12, No. 1, Dec. 13, 2020 [retrieved on Dec. 7, 2021]. Retrieved from the Internet: <URL: https://pubs.acs.org/doi/10.1021/acsmedchemlett.0c00533 >. abstract.

European Search Report for PCT/US2021054540 mailed Apr. 19, 2024.

Zheng et al. Design and Synthesis of Highly Potent and Isoform Selective JNK3 Inhibitors: SAR Studies on Aminopyrazole Derivatives Journal of Medicinal Chemistry 2014 57 (23), 10013-10030 DOI: 10.1021/jm501256y.

*Primary Examiner* — Charanjit Aulakh
(74) *Attorney, Agent, or Firm* — Thomas | Horstemeyer, LLP

(57) ABSTRACT

Described herein are compounds that are kinase inhibitors. The disclosed compounds have improved properties that lead to specific targeting of kinases without inhibiting the activity of related enzymes including, making them useful for therapeutic intervention in a variety of disorders and disease in which inhibition of the kinase can be clinically useful, e.g., Alzheimer's disease and other neurodegenerative diseases. In further aspects, the disclosed compounds can be used in methods of treating a neurodegenerative disease associated with inflammation, such as Alzheimer's disease, Huntington's disease, Parkinson's disease, epilepsy, stroke, amyotrophic lateral sclerosis (ALS), spinal muscular atrophy (SMA), or a disease or disorder such as deafness, glaucoma, organ failure, or cancers, including, but not limited to, those susceptible to combination therapy with epigenetic targets such as those associated with bromodomain (BRD) proteins, histone deacetylases (HDACs), and the like.

19 Claims, 3 Drawing Sheets

3

4

| | 3 | 4 |
|---|---|---|
| JNK3: | > 10 μM | 0.8 μM |
| JNK1: | > 20 μM | > 20 μM |

JNK biochemical inhibition $IC_{50}$

| | 5 | 6 |
|---|---|---|
| JNK3: | 0.2 μM | 0.05 μM |
| JNK1: | > 20 μM | 3.6 μM |
| ($p38^{\alpha}$): | (> 20 μM) | (> 20 μM) |

5

6

KINASE INHIBITORS FOR THE TREATMENT OF NEURODEGENERATIVE DISEASES

CROSS REFERENCE TO RELATED APPLICATIONS

This application is a 35 U.S.C. § 371 national stage application of PCT application serial number PCT/US2021/054540, filed on Oct. 12, 2021, which claims priority to U.S. provisional application entitled "KINASE INHIBITORS FOR THE TREATMENT OF NEURODEGENERATIVE DISEASES," having Ser. No. 63/092,333, filed on Oct. 15, 2020, which are entirely incorporated herein by reference.

STATEMENT REGARDING FEDERALLY SPONSORED RESEARCH OR DEVELOPMENT

This disclosure was made with U.S. Government support under grant number 5R01AG055059, awarded by the National Institute on Aging, a division of the National Institutes of Health. The U.S. government has certain rights in the disclosure.

BACKGROUND

Alzheimer's disease is an irreversible brain disease that slowly destroys memory, thinking skills, and the ability to carry out simple tasks. Alzheimer's disease is the most common form of dementia, with as many as 5.9 million patients in the United States, alone. No cure currently exists, and, furthermore, drugs targeting β-amyloid, a crucial component of the amyloid plaques found in the brain of Alzheimer's patients, have so far been unsuccessful. Thus, current approaches to treating Alzheimer's disease focus on treating cognitive symptoms without altering the underlying causes of the disease.

The mitogen-activated protein kinase 10 gene, or MAPK10, produces proteins known as c-Jun N-terminal kinases (JNK). JNK proteins have multiple isoforms due to alternative splicing; JNK3 is a JNK protein specific to the central nervous system and is activated by inflammation, reactive oxygen species, cholesterol, endoplasmic reticulum stress, and autophagy, all of which manifest in Alzheimer's disease. Experiments in which JNK3 was deleted from an aggressive Alzheimer's disease mouse model resulted in a 90% reduction of β-amyloid, an increase in neuron numbers, and improvement in synaptic function.

JNK3 has also been implicated in the progression of Huntington's disease, Parkinson's disease, stroke, amyotrophic lateral sclerosis (ALS), spinal muscular atrophy (SMA), deafness, glaucoma, organ failure, and several cancers, including, but not limited to, those susceptible to combination therapy with epigenetic targets such as those associated with bromodomain (BRD) proteins, histone deacetylases (HDACs), and the like. JNK3 is further involved in other functions related to the central nervous system including the control of feeding, the regulation of energy homeostasis, and body weight. Identifying compounds that inhibit JNK3 activity without also causing side effects related to JNK1 and JNK2 is desirable in terms of developing new neuroprotective therapies for JNK3-associated diseases and conditions.

Despite advances in Alzheimer's disease research, there is still a scarcity of compounds that are both potent, efficacious, and selective inhibitors of JNK3 as well as effective in the treatment of inflammation associated with cell and tissue stress and central nervous system diseases in which JNK3 is implicated. These needs and other needs are satisfied by the present disclosure.

SUMMARY

In accordance with the purpose(s) of the present disclosure, as embodied and broadly described herein, the disclosure, in one aspect, relates to compounds that are kinase inhibitors. The disclosed compounds have improved properties that lead to specific targeting of kinases without inhibiting the activity of related enzymes including, making them useful for therapeutic intervention in a variety of disorders and disease in which inhibition of the kinase can be clinically useful, e.g., Alzheimer's disease and other neurodegenerative diseases.

In further aspects, the disclosed compounds can be used in methods of treating a neurodegenerative disease associated with inflammation, such as Alzheimer's disease, Huntington's disease, Parkinson's disease, epilepsy, stroke, amyotrophic lateral sclerosis (ALS), spinal muscular atrophy (SMA), or a disease or disorder such as deafness, glaucoma, organ failure, or cancers, including, but not limited to, those susceptible to combination therapy with epigenetic targets such as those associated with bromodomain (BRD) proteins, histone deacetylases (HDACs), and the like.

Disclosed are compounds having a formula represented by a structure:

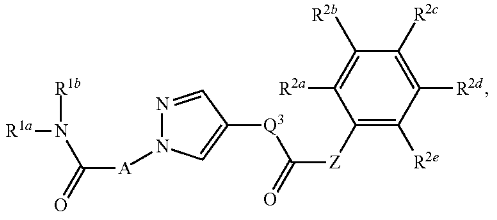

wherein each of $R^{1a}$ and $R^{1b}$ are independently selected from hydrogen, C1-C8 nitrile, C1-C8 alkyl, C1-C8 alkoxy, C1-C8 haloalkyl, C3-C8 cycloalkyl, C3-C8 heterocyclyl, heteroaryl, and aryl;

wherein each of $R^{2a}$, $R^{2b}$, $R^{2c}$, $R^{2d}$, and $R^{2e}$ are independently selected from hydrogen, halo, hydroxy, nitro, azido, —$SF_5$, C1-C3 alkyl, C1-C3 haloalkyl, C1-C3 alkoxy, C1-C3 aminoalkyl, C1-C3 hydroxyalkyl, and —(C1-C3 alkanediyl)-$NR^{5a}R^{5b}$;

wherein each occurrence of $R^{5a}$ and $R^{5b}$ is independently selected from hydrogen, C1-C3 alkyl, C3-C8 cycloalkyl, C3-C8 heterocycloalkyl, aryl and heteroaryl;

wherein A is a structure represented by a formula:

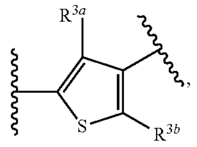

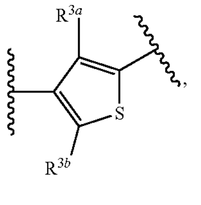

or

-continued

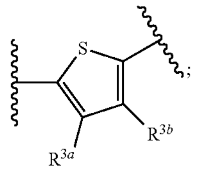

wherein each of $R^{3a}$ and $R^{3b}$ is selected from hydrogen, halo, hydroxy, nitro, amino, azido, —$SF_5$, C1-C3 alkyl, C1-C3 haloalkyl, C1-C3 alkoxy, C1-C3 aminoalkyl, and C1-C3 hydroxyalkyl;

wherein $Q^3$ is $NR^{4c}$, $CR^{4c}$, or O;

wherein $R^{4c}$ is selected from hydrogen, halo, hydroxy, nitro, azido, —$SF_5$, C1-C3 alkyl, C1-C3 haloalkyl, C1-C3 alkoxy, C1-C3 aminoalkyl, C1-C3 hydroxyalkyl, and —(C0-C3 alkanediyl)-$NR^{5a}R^{5b}$;

wherein Z is selected from —O—, —S—, and —$NR^6$—;

wherein $R^6$ is selected from hydrogen and C1-C3 alkyl; or a pharmaceutically acceptable salt thereof.

Also disclosed are pharmaceutical compositions comprising a therapeutically effective amount of a disclosed compound, or a pharmaceutically acceptable salt thereof, and a pharmaceutically acceptable carrier.

Also disclosed are methods for the treatment of a disease or disorder in a mammal comprising the step of administering to the mammal a therapeutically effective amount of at least one disclosed compound, or a pharmaceutically acceptable salt thereof, or a disclosed pharmaceutical composition.

Also disclosed are methods for the treatment of a neurodegenerative disease or disorder in a mammal comprising the step of administering to the mammal a therapeutically effective amount of at least one disclosed compound, or a pharmaceutically acceptable salt thereof, or a disclosed pharmaceutical composition.

Also disclosed are methods for the treatment of a disease or disorder of the peripheral or central nervous system in a mammal comprising the step of administering to the mammal a therapeutically effective amount of at least one disclosed compound, or a pharmaceutically acceptable salt thereof, or a disclosed pharmaceutical composition.

Other systems, methods, features, and advantages of the present disclosure will be or become apparent to one with skill in the art upon examination of the following detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

Additional advantages of the disclosure will be set forth in part in the description which follows, and in part will be obvious from the description, or can be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

Further aspects of the present disclosure will be readily appreciated upon review of the detailed description of its various embodiments, described below, when taken in conjunction with the accompanying drawings.

DETAILED DESCRIPTION

Figure 1:
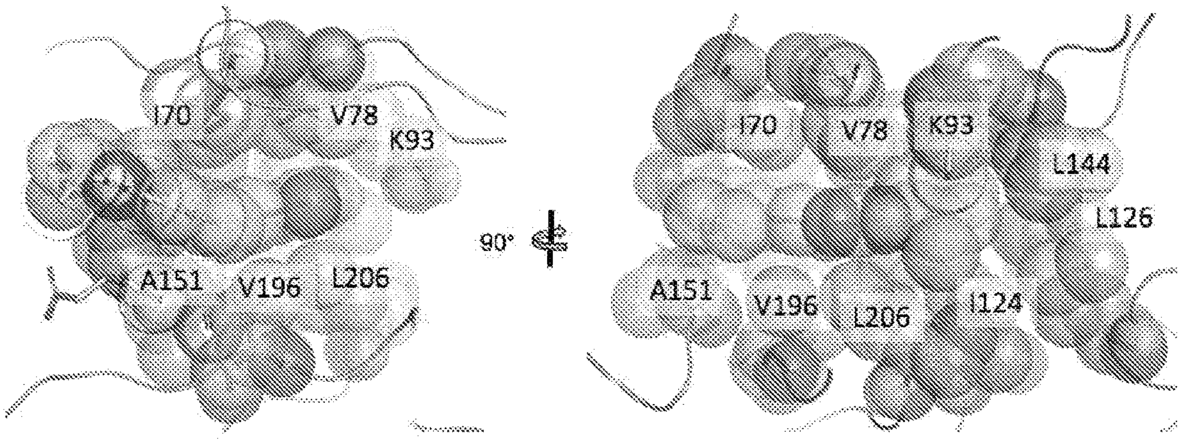
FIG. 1 shows the transparent sphere and wire model of residues involved in hydrophobic pocket formation. The residues, 170 and A151 sandwich the thiophene ring. V78, A91 (not visible), and V196 VdW contact with pyrazole ring. The residues K93, I124, L126 and L144 wraps around Cl-phenyl ring. 17 is colored blue and the protein residues are colored grey.

Many modifications and other embodiments disclosed herein will come to mind to one skilled in the art to which the disclosed compositions and methods pertain having the benefit of the teachings presented in the foregoing descriptions. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Disclosed are the components to be used to prepare the compositions of the disclosure as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the disclosure. Thus, if there are a variety of additional steps that can be performed it is understood that each of these additional steps can be performed with any specific embodiment or combination of embodiments of the methods of the disclosure.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

Described herein are compounds that can inhibit one or more kinases and have therapeutic or clinical utility for a disease or disorder that can be treated by inhibition of the kinase. Also described herein are methods of synthesizing the disclosed compounds. Further described herein are methods of administering the disclosed compounds to a subject in need thereof. In some aspects, the subject can have a disease or disorder associated with kinase activity, such as Alzheimer's disease, Huntington's disease, Parkinson's disease, epilepsy, amyotrophic lateral sclerosis (ALS), spinal muscular atrophy (SMA), deafness, glaucoma, organ failure, or cancer. Other compositions, compounds, methods, features, and advantages of the present disclosure will be or become apparent to one having ordinary skill in the art upon examination of the following detailed description and examples. It is intended that all such additional compositions, compounds, methods, features, and advantages be included within this description, and be within the scope of the present disclosure.

All publications and patents cited in this specification are cited to disclose and describe the methods and/or materials in connection with which the publications are cited. All such publications and patents are herein incorporated by reference as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Aspects of the present disclosure will employ, unless otherwise indicated, techniques of molecular biology, microbiology, organic chemistry, biochemistry, physiology, cell biology, and the like, which are within the skill of the art. Such techniques are explained fully in the literature.

Prior to describing the various aspects of the present disclosure, the following definitions are provided and should be used unless otherwise indicated. Additional terms may be defined elsewhere in the present disclosure.

Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a pharmaceutically-acceptable salt," "a pharmaceutically-acceptable ester," or "a pharmaceutically-acceptable carrier," includes, but is not limited to, combinations and/or mixtures of two or more such pharmaceutically-acceptable salts, esters, or carriers, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

As used herein, "c-Jun N-terminal kinase 3," "JNK3," "mitogen-activated protein kinase 10," and "MAPK10" can be used interchangeably, and refer to an enzyme encoded by a gene in humans with a cytogenetic location of 4q21.3 and a molecular location of base pairs 86,010,395-86,594,131 on the reverse strand of chromosome 4 (*Homo sapiens* Annotation Release 89, GRCh38.p10). The gene structure in humans contains 20 exons and 19 introns, 16 of which are alternative, leading to 7 distinct JNK protein isoforms. JNK3 has an EC classification of 2.7.11.24; an intracellular location within the nucleus; and regulates signal transduction in response to environmental stress by phosphorylation of various transcription factors including ATF2, Elk-1, and members of the Jun family through phosphorylating target substrates on serine or threonine residues followed by a proline. JNK3 is a neuron-specific isoform of JNK and activation and nuclear localization of JNK3 has been associated with hypoxic and/or ischemic damage of CA1 neurons in the hippocampus. Phosphorylation of specific tyrosine and threonine residues of JNK3 are required for activation. JNK3 has also been referred to as FLJ12099, FLJ33785, JNK3A, MGC50974, PRKM10, p493F12, p54bSAPK, MAP kinase p49 3F12, stress-activated protein kinase 1b (SAPK1b), stress-activated protein kinase JNK3, ERK, extracellular signal-regulated kinase, microtubule-associated protein kinase, and myelin basic protein kinase.

As used herein, JNK1 is a c-Jun N-terminal kinase product of the MAPK8 gene that is found in all tissues and cells and is involved in a wide variety of cellular processes related to biochemical signaling including proliferation, differentiation, and apoptosis, including UV-radiation induced apoptosis. P38 proteins are mitogen-activated protein kinases from MAPK11, MAPK12, MAPK13, and MAPK14 genes and are responsive to stress stimuli including, but not limited to, cytokines, UV radiation, heat shock, and osmotic shock. In one aspect, compounds that inhibit JNK3 also undesirably target JNK1 and P38.

As used herein, JNK2 also referred to as MAP kinase 7 or MKK7 is a serine/threonine-protein kinase encoded by a gene in humans with a cytogenetic location of 5q35.3. JNK2 has an EC classification of 2.7.11.24. JNK2 is involved in various processes such as cell proliferation, differentiation, migration, transformation and programmed cell death.

As used herein, p38a kinase also referred to as MAP kinase 14 or MAPK14 is a protein that, in humans, is encoded by the MAPK14 gene.

As used herein, mitogen-activated protein kinase kinase kinase kinase (MAP4K) is a family of proteins involved in cellular signal transduction.

As used herein, ABL1, also known as Tyrosine-protein kinase ABL1, is a protein that, in humans, is encoded by the ABL1 gene (previous symbol ABL) located on chromosome 9.

As used herein, ABL2, also known as Tyrosine-protein kinase ABL2, is a protein that, in humans, is encoded by the ABL2 gene.

As used herein, DDR1, also known as Discoidin domain receptor member 1, is a protein that, in humans, is encoded by the DDR1 gene.

As used herein, DDR2, also known as Discoidin domain receptor member 2, is a protein that, in humans, is encoded by the DDR2 gene.

As used herein, CK1, also known as Casein kinase 1, are protein kinases that function as regulators of signal transduction pathways in most eukaryotic cell types.

As used herein, MINK1, also known as Misshapen-like kinase 1, are enzymes that in humans are encoded by the MINK1 gene.

As used herein, HGK, also known as hepatocyte progenitor kinase-like/germinal center kinase-like kinase, is a member of the human STE20/mitogen-activated protein kinase kinase kinase kinase family of serine/threonine kinases.

As used herein, TNIK, also known as TRAF2 and NCK-interacting protein kinase, is a protein that, in humans, is encoded by the TNIK gene.

As used herein, GCK, also known mitogen-activated protein kinase kinase kinase kinase 2 is an enzyme that in humans is encoded by the MAP4K2 gene.

The terms "inhibits," "inhibiting," or "inhibitor" of kinase, as used herein, refer to inhibition of the enzyme, unless otherwise specified.

As used herein, "$IC_{50}$," is intended to refer to the concentration of a substance (e.g., a compound or a drug) that is required for 50% inhibition of a biological process, enzymatic reaction, or component of a biological or enzymatic process. For example, $IC_{50}$ refers to the half maximal (50%) inhibitory concentration (IC) of a substance as determined in a suitable assay. For example, an $IC_{50}$ for JNK3 activity can be determined in an in vitro enzymatic assay using the methods described herein.

As used herein, "administering" can refer to an administration that is oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, "therapeutic agent" can refer to any substance, compound, molecule, and the like, which can be biologically active or otherwise can induce a pharmacologic, immunogenic, biologic and/or physiologic effect on a subject to which it is administered to by local and/or systemic action. A therapeutic agent can be a primary active agent, or in other words, the component(s) of a composition to which the whole or part of the effect of the composition is attributed. A therapeutic agent can be a secondary therapeutic agent, or in other words, the component(s) of a composition to which an additional part and/or other effect of the composition is attributed. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents and are meant to include future updates.

As used herein, "attached" can refer to covalent or non-covalent interaction between two or more molecules. Non-covalent interactions can include ionic bonds, electrostatic interactions, van der Waals forces, dipole-dipole interactions, dipole-induced-dipole interactions, London dispersion forces, hydrogen bonding, halogen bonding, electromagnetic interactions, π-π interactions, cation-π interactions, anion-π interactions, polar π-interactions, and hydrophobic effects.

As used interchangeably herein, "subject," "individual," or "patient" can refer to a vertebrate organism, such as a mammal (e.g. human). "Subject" can also refer to a cell, a population of cells, a tissue, an organ, or an organism, preferably to human and constituents thereof. It is understood that a vertebrate can be mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Moreover, adult and newborn subjects, as well as fetuses, whether male or female, are intended to be covered. A patient refers to a subject afflicted with a clinical condition, disease or disorder. The term "patient" includes human and veterinary subjects.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as Alzheimer's disease, Huntington's disease, Parkinson's disease, amyotrophic lateral sclerosis (ALS), spinal muscular atrophy (SMA), deafness, glaucoma, organ failure, or a cancer. The effect can be therapeutic in terms of a partial or complete cure of a disease, condition, symptom or adverse effect attributed to the disease, disorder, or condition. The term "treatment" as used herein can include any treatment of Alzheimer's disease, Huntington's disease, Parkinson's disease, amyotrophic lateral sclerosis (ALS), spinal muscular atrophy (SMA), deafness, glaucoma, organ failure, or cancer in a subject, particularly a human and can include any one or more of the following: (a) preventing the disease from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, e.g., such as treating the pain of a subject by administration of an analgesic agent even though such agent does not treat the cause of the pain.

As used herein, "dose," "unit dose," or "dosage" can refer to physically discrete units suitable for use in a subject, each unit containing a predetermined quantity of a disclosed compound and/or a pharmaceutical composition thereof calculated to produce the desired response or responses in association with its administration.

As used herein, "therapeutic" can refer to treating, healing, and/or ameliorating a disease, disorder, condition, or side effect, or to decreasing in the rate of advancement of a disease, disorder, condition, or side effect.

As used herein, "effective amount" can refer to the amount of a disclosed compound or pharmaceutical composition provided herein that is sufficient to effect beneficial or desired biological, emotional, medical, or clinical response of a cell, tissue, system, animal, or human. An effective amount can be administered in one or more administrations, applications, or dosages. The term can also include within its scope amounts effective to enhance or restore to substantially normal physiological function.

As used herein, the term "therapeutically effective amount" refers to an amount that is sufficient to achieve the desired therapeutic result or to have an effect on undesired symptoms but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors within the knowledge and expertise of the health practitioner and which may be well known in the medical arts. In the case of treating a particular disease or condition, in some instances, the desired response can be inhibiting the progression of the disease or condition. This may involve only slowing the progression of the disease temporarily. However, in other instances, it may be desirable to halt the progression of the disease permanently. This can be monitored by routine diagnostic methods known to one of ordinary skill in the art for any particular disease. The desired response to treatment of the disease or condition also can be delaying the onset or even preventing the onset of the disease or condition.

For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. It is generally preferred that a maximum dose of the pharmacological agents of the disclosure (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

A response to a therapeutically effective dose of a disclosed compound and/or pharmaceutical composition, for example, can be measured by determining the physiological effects of the treatment or medication, such as the decrease or lack of disease symptoms following administration of the treatment or pharmacological agent. Other assays will be known to one of ordinary skill in the art and can be employed for measuring the level of the response. The amount of a treatment may be varied for example by increasing or decreasing the amount of a disclosed compound and/or pharmaceutical composition, by changing the disclosed compound and/or pharmaceutical composition administered, by changing the route of administration, by changing the dosage timing and so on. Dosage can vary, and can be administered in one or more dose administrations daily, for one or several days. Guidance can be found in the literature for appropriate dosages for given classes of pharmaceutical products.

In the present disclosure, it is understood that in some cases, an effective amount or dose of a disclosed compound is the amount of the composition that is capable of inhibiting a kinase to provide a clinically meaningful decrease in the signs, symptoms, or causes of a disease, or any other desired alteration of a biological system, as a result of inhibiting the kinase. For example, an "effective amount" for therapeutic uses. In some aspects, an appropriate "effective" amount in any individual case is determined using techniques, such as a dose escalation study.

As used herein, the term "prophylactically effective amount" refers to an amount effective for preventing onset or initiation of a disease or condition.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

The term "pharmaceutically acceptable salts", as used herein, means salts of the active principal agents which are prepared with acids or bases that are tolerated by a biological system or tolerated by a subject or tolerated by a biological system and tolerated by a subject when administered in a therapeutically effective amount. When compounds of the present disclosure contain relatively acidic functionalities, base addition salts can be obtained by contacting the neutral form of such compounds with a sufficient amount of the desired base, either neat or in a suitable inert solvent. Examples of pharmaceutically acceptable base addition salts include, but are not limited to; sodium, potassium, calcium, ammonium, organic amino, magnesium salt, lithium salt, strontium salt or a similar salt. When compounds of the present disclosure contain relatively basic functionalities, acid addition salts can be obtained by contacting the neutral form of such compounds with a sufficient amount of the desired acid, either neat or in a suitable inert solvent. Examples of pharmaceutically acceptable acid addition salts include, but are not limited to; those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydroiodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like.

The term "pharmaceutically acceptable ester" refers to esters of compounds of the present disclosure which hydrolyze in vivo and include those that break down readily in the human body to leave the parent compound or a salt thereof. Examples of pharmaceutically acceptable, non-toxic esters of the present disclosure include C 1-to-C 6 alkyl esters and C 5-to-C 7 cycloalkyl esters, although C 1-to-C 4 alkyl esters are preferred. Esters of disclosed compounds can be prepared according to conventional methods. Pharmaceutically acceptable esters can be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, for example with methyl iodide, benzyl iodide, cyclopentyl iodide or alkyl triflate. They also can be prepared by reaction of the compound with an acid such as hydrochloric acid and an alcohol such as ethanol or methanol.

The term "pharmaceutically acceptable amide" refers to non-toxic amides of the present disclosure derived from ammonia, primary C 1-to-C 6 alkyl amines and secondary C 1-to-C 6 dialkyl amines. In the case of secondary amines, the amine can also be in the form of a 5- or 6-membered heterocycle containing one nitrogen atom. Amides derived from ammonia, C 1-to-C 3 alkyl primary amides and C 1-to-C 2 dialkyl secondary amides are preferred. Amides of disclosed compounds can be prepared according to conventional methods. Pharmaceutically acceptable amides can be prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable amides are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, and piperidine. They also can be prepared by reaction of the compound with an acid such as sulfuric acid and an alkylcarboxylic acid such as acetic acid, or with acid and an arylcarboxylic acid such as benzoic acid under dehydrating conditions such as with molecular sieves added. The composition can contain a compound of the present disclosure in the form of a pharmaceutically acceptable prodrug.

The term "pharmaceutically acceptable prodrug" or "prodrug" represents those prodrugs of the compounds of the present disclosure which are, within the scope of sound medical judgment, suitable for use in contact with the tissues of humans and lower animals without undue toxicity, irritation, allergic response, and the like, commensurate with a reasonable benefit/risk ratio, and effective for their intended use. Prodrugs of the present disclosure can be rapidly transformed in vivo to a parent compound having a structure of a disclosed compound, for example, by hydrolysis in blood. A thorough discussion is provided in T. Higuchi and V. Stella, Pro-drugs as Novel Delivery Systems, V. 14 of the A.C.S. Symposium Series, and in Edward B. Roche, ed., Bioreversible Carriers in Drug Design, American Pharmaceutical Association and Pergamon Press (1987).

The term "contacting" as used herein refers to bringing a disclosed compound or pharmaceutical composition in proximity to a cell, a target protein, or other biological entity together in such a manner that the disclosed compound or pharmaceutical composition can affect the activity of the a cell, target protein, or other biological entity, either directly; i.e., by interacting with the cell, target protein, or other biological entity itself, or indirectly; i.e., by interacting with another molecule, co-factor, factor, or protein on which the activity of the cell, target protein, or other biological entity itself is dependent.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. Similarly, "$Ar^1$," "$Ar^2$," "$Ar^3$," and "$Ar^4$" are used herein as generic symbols to represent various specific aryl substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, nitrile, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein. In one aspect, the heterocycloalkyl group can be a lactam, including but not limited to an N-substituted lactam.

Throughout the specification "alkyl" is generally used to refer to both unsubstituted alkyl groups and substituted alkyl groups; however, substituted alkyl groups are also specifically referred to herein by identifying the specific substituent (s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like. The term "nitrilealkyl" specifically refers to an alkyl group that is substituted with one or more nitrile groups.

The term "alkanediyl", as used herein, unless otherwise indicated, means bivalent straight and branched chained saturated hydrocarbon radicals having carbon atoms. For example, "C1-C6 alkanediyl" would refer to bivalent straight and branched chained saturated hydrocarbon radicals having 1 to 6 carbon atoms, such as, for example, methylene, 1,2-ethanediyl, 1,3-propanediyl, 1,4-butanediyl, 1,5-pentanediyl, 1,6-hexanediyl and the branched isomers thereof.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or -$OA^1$-$(OA^2)_a$-$OA^3$, where "a" is an integer of from 1 to 200 and $A^1$, $A^2$, and $A^3$ are alkyl and/or cycloalkyl groups.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "heteroaryl" as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multicyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl" as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) or —N(-alkyl)$_2$ where alkyl is a described herein. Representative examples include, but are not limited to, methylamino group, ethylamino group, propylamino group, isopropylamino group, butylamino group, isobutylamino group, (sec-butyl)amino group, (tert-butyl) amino group, pentylamino group, isopentylamino group, (tert-pentyl)amino group, hexylamino group, and the like.

The term "ester" as used herein is represented by the formula —$OC(O)A^1$ or —$C(O)OA^1$, where $A^1$ can be alkyl, cycloalkyl, alkenyl, cycloalkenyl, alkynyl, cycloalkynyl, aryl, or heteroaryl group as described herein. The term "polyester" as used herein is represented by the formula $-(A^1O(O)C\text{-}A^2\text{-}C(O)O)_a$ or $-(A^1O(O)C\text{-}A^2\text{-}OC(O))_a$, where $A^1$ and $A^2$ can be, independently, an alkyl, cycloalkyl, alkenyl, cycloalkenyl, alkynyl, cycloalkynyl, aryl, or heteroaryl group described herein and "a" is an integer from 1 to 500.

The term "ether" as used herein is represented by the formula $A^1OA^2$, where $A^1$ and $A^2$ can be, independently, an alkyl, cycloalkyl, alkenyl, cycloalkenyl, alkynyl, cycloalkynyl, aryl, or heteroaryl group described herein. The term "polyether" as used herein is represented by the formula $-(A^1O\text{-}A^2O)_a$, where $A^1$ and $A^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen" or "halide," as used herein can be used interchangeably and refer to F, Cl, Br, or I.

The term "hydroxyl" or "hydroxy" as used herein is represented by the formula —OH.

The term "nitro" as used herein is represented by the formula —$NO_2$.

The term "nitrile" or "cyano" as used herein is represented by the formula —CN.

The term "azide" or "azido" as used herein is represented by the formula —$N_3$.

"$R^1$," "$R^2$," "$R^3$," . . . "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

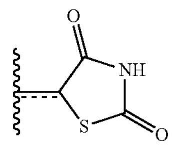

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present disclosure unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfonyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, isotopes, salts of esters or amides, and N-oxides of a parent compound.

Compounds described herein can contain one or more double bonds and, thus, potentially give rise to cis/trans (E/Z) isomers, as well as other conformational isomers. Unless stated to the contrary, the disclosure includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present disclosure includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the disclosure include isotopes of hydrogen, carbon, nitrogen, oxygen, sulfur, fluorine and chlorine, such as $^{2}H$ (D), $^{3}H$ (T), $^{11}C$, $^{13}C$, $^{14}C$, $^{15}N$, $^{18}O$, $^{17}O$, $^{35}S$, $^{18}F$, $^{19}F$, and $^{36}Cl$, respectively. Compounds further comprise prodrugs thereof and pharmaceutically acceptable salts of said compounds or of said prodrugs which contain the aforementioned isotopes and/or other isotopes of other atoms are within the scope of this disclosure. Certain isotopically-labeled compounds of the present disclosure, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of the present disclosure and prodrugs thereof can generally be prepared by carrying out the procedures below, by substituting a readily available isotopically labeled reagent for a non-isotopically labeled reagent.

It is known that chemical substances form solids which are present in different states of order which are termed polymorphic forms or modifications. The different modifications of a polymorphic substance can differ greatly in their physical properties. The compounds according to the disclosure can be present in different polymorphic forms, with it being possible for particular modifications to be metastable. Unless stated to the contrary, the disclosure includes all such possible polymorphic forms.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise specified, temperatures referred to herein are based on atmospheric pressure (i.e. one atmosphere).

Described herein are compounds that inhibit one or more kinases while not affecting the activity of closely-related enzymes and that have therapeutic or clinical utility. Also described herein are methods of synthesizing the disclosed compounds. Also described herein are methods of administering the disclosed compounds to a subject in need thereof. In some aspects, the subject can have a neurodegenerative disease such as, for example, Alzheimer's disease, Huntington's disease, Parkinson's disease, epilepsy, stroke, amyotrophic lateral sclerosis (ALS), spinal muscular atrophy (SMA), deafness, glaucoma, organ failure, and several cancers, including, but not limited to, those susceptible to combination therapy with epigenetic targets such as those associated with bromodomain (BRD) proteins, histone deacetylases (HDACs), and the like. Other compositions, compounds, methods, features, and advantages of the present disclosure will be or become apparent to one having ordinary skill in the art upon examination of the following detailed description and examples. It is intended that all such additional compositions, compounds, methods, features, and advantages be included within this description, and be within the scope of the present disclosure.

Compounds

Disclosed are compounds having a formula represented by a structure:

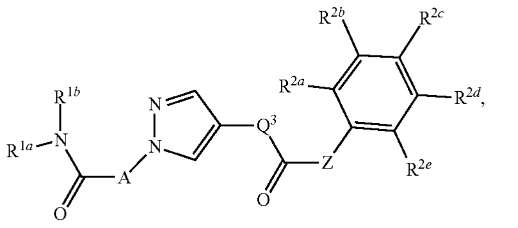

wherein each of $R^{1a}$ and $R^{1b}$ are independently selected from hydrogen, C1-C8 nitrile, C1-C8 alkyl, C1-C8 alkoxy, C1-C8 haloalkyl, C3-C8 cycloalkyl, C3-C8 heterocyclyl, heteroaryl, and aryl;

wherein each of $R^{2a}$, $R^{2b}$, $R^{2c}$, $R^{2d}$, and $R^{2e}$ are independently selected from hydrogen, halo, hydroxy, nitro, azido, —$SF_5$, C1-C3 alkyl, C1-C3 haloalkyl, C1-C3 alkoxy, C1-C3 aminoalkyl, C1-C3 hydroxyalkyl, and —(C1-C3 alkanediyl)-$NR^{5a}R^{5b}$;

wherein each occurrence of $R^{5a}$ and $R^{5b}$ is independently selected from hydrogen, C1-C3 alkyl, C3-C8 cycloalkyl, C3-C8 heterocycloalkyl, aryl and heteroaryl;

wherein A is a structure represented by a formula:

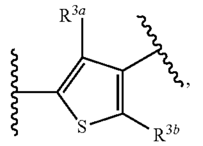 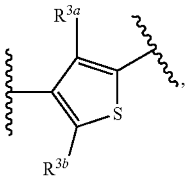 or

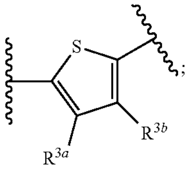

wherein each of $R^{3a}$ and $R^{3b}$ is selected from hydrogen, halo, hydroxy, nitro, amino, azido, —$SF_5$, C1-C3 alkyl, C1-C3 haloalkyl, C1-C3 alkoxy, C1-C3 aminoalkyl, and C1-C3 hydroxyalkyl;

wherein $Q^3$ is $NR^{4c}$, $CR^{4c}$, or O;

wherein $R^{4c}$ is selected from hydrogen, halo, hydroxy, nitro, azido, —$SF_5$, C1-C3 alkyl, C1-C3 haloalkyl, C1-C3 alkoxy, C1-C3 aminoalkyl, C1-C3 hydroxyalkyl, and —(C0-C3 alkanediyl)-$NR^{5a}R^{5b}$;

wherein Z is selected from —O—, —S—, and —$NR^6$—;

wherein $R^6$ is selected from hydrogen and C1-C3 alkyl; or a pharmaceutically acceptable salt thereof.

In one aspect, the disclosed compounds can possess at least one center of asymmetry, they can be present in the form of their racemates, in the form of the pure enantiomers and/or diastereomers or in the form of mixtures of these enantiomers and/or diastereomers. The stereoisomers can be present in the mixtures in any arbitrary proportions. In some aspects, provided this is possible, the disclosed compounds can be present in the form of the tautomers.

Thus, methods which are known per se can be used, for example, to separate the disclosed compounds which possess one or more chiral centers and occur as racemates into their optical isomers, i.e., enantiomers or diastereomers. The separation can be effected by means of column separation on chiral phases or by means of recrystallization from an optically active solvent or using an optically active acid or base or by means of derivatizing with an optically active reagent, such as an optically active alcohol, and subsequently cleaving off the residue.

The compounds described in the disclosure can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the disclosure to form solvates and hydrates. Unless stated to the contrary, the disclosure includes all such possible solvates.

The disclosed compounds can be used in the form of salts derived from inorganic or organic acids. Pharmaceutically acceptable salts include salts of acidic or basic groups present in the disclosed compounds. Suitable pharmaceutically acceptable salts include base addition salts, including alkali metal salts, e.g., sodium or potassium salts; alkaline earth metal salts, e.g., calcium or magnesium salts; and salts formed with suitable organic ligands, e.g., quaternary ammonium salts, which may be similarly prepared by reacting the drug compound with a suitable pharmaceutically acceptable base. The salts can be prepared in situ during the final isolation and purification of the compounds of the present disclosure; or following final isolation by reacting a free base function, such as a secondary or tertiary amine, of a disclosed compound with a suitable inorganic or organic acid; or reacting a free acid function, such as a carboxylic acid, of a disclosed compound with a suitable inorganic or organic base.

Acidic addition salts can be prepared in situ during the final isolation and purification of a disclosed compound, or separately by reacting moieties comprising one or more nitrogen groups with a suitable acid. In various aspects, acids which may be employed to form pharmaceutically acceptable acid addition salts include such inorganic acids as hydrochloric acid, sulfuric acid and phosphoric acid and such organic acids as oxalic acid, maleic acid, succinic acid and citric acid. In a further aspect, salts further include, but are not limited, to the following: hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzensulfonate, p-toluenesulfonate, butyrate, camphorate, camphorsulfonate, digluconate, glycerophosphate, hemisulfate, heptanoate, hexanoate, fumarate, hydrochloride, 2-hydroxyethanesulfonate (isethionate), nicotinate, 2-naphthalenesulfonate, oxalate, pectinate, persulfate, 3-phenylpropionate, picrate, pivalate, propionate, succinate, tartrate, thiocyanate, phosphate, glutamate, bicarbonate, undecanoate, and pamoate (i.e., 1,1'-methylene-bis-(2-hydroxy-3-naphthoate)) salts. Also, basic nitrogen-containing groups can be quaternized with such agents as lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others.

Basic addition salts can be prepared in situ during the final isolation and purification of a disclosed compound, or separately by reacting carboxylic acid moieties with a suitable base such as the hydroxide, carbonate or bicarbonate of a pharmaceutical acceptable metal cation or with ammonia, or an organic primary, secondary or tertiary amine. Pharmaceutical acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine and the like. In further aspects, bases which may be used in the preparation of pharmaceutically acceptable salts include the following: ammonia, L-arginine, benethamine, benzathine, calcium hydroxide, choline, deanol, diethanolamine, diethylamine, 2-(diethylamino)-ethanol, ethanolamine, ethylenediamine, N-methylglucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, secondary amine, sodium hydroxide, triethanolamine, tromethamine and zinc hydroxide.

Methods of Making the Compounds

In one aspect, the present disclosure relates to methods of making compounds useful as selective inhibitors of kinases, which can be useful in the treatment of clinical conditions, diseases, and disorders associated with kinase dysfunction and other diseases in which is the kinases described herein are involved. In one aspect, the disclosure relates to disclosed synthetic manipulations. In a further aspect, the disclosed compounds include the products of the synthetic methods described herein. In a further aspect, the disclosed compounds include a compound produced by the synthetic method described herein. In a still further aspect, the disclosure includes a pharmaceutical composition containing a therapeutically effective amount of the product of the disclosed methods and a pharmaceutically acceptable carrier. In a still further aspect, the disclosure includes a method for manufacturing a medicament including combining at least one compound of any of the disclosed compounds or at least one product of any of the disclosed methods with a pharmaceutically acceptable carrier or diluent.

The compounds of this disclosure can be prepared by employing reactions as shown in the disclosed schemes, in addition to other standard manipulations that are known in the literature, exemplified in the experimental sections or clear to one skilled in the art. The following examples are provided so that the disclosure might be more fully understood, are illustrative only, and should not be construed as limiting. For clarity, examples having fewer substituents can be shown where multiple substituents are allowed under the definitions disclosed herein.

It is contemplated that each disclosed method can further include additional steps, manipulations, and/or components. It is also contemplated that any one or more steps, manipulations, and or components can be optionally omitted from the disclosure. It is understood that a disclosed method can be used to provide the disclosed compounds. It is also understood that the products of the disclosed methods can be employed in the disclosed compositions, kits, and uses.

In one aspect, the compounds described herein can be prepared generically by the synthetic scheme as shown below, wherein certain substituents and/or functional groups can be varied on the reaction intermediates to produce, for example, different substituents on the phenyl ring or at any other variable position in the structure:

Scheme 1

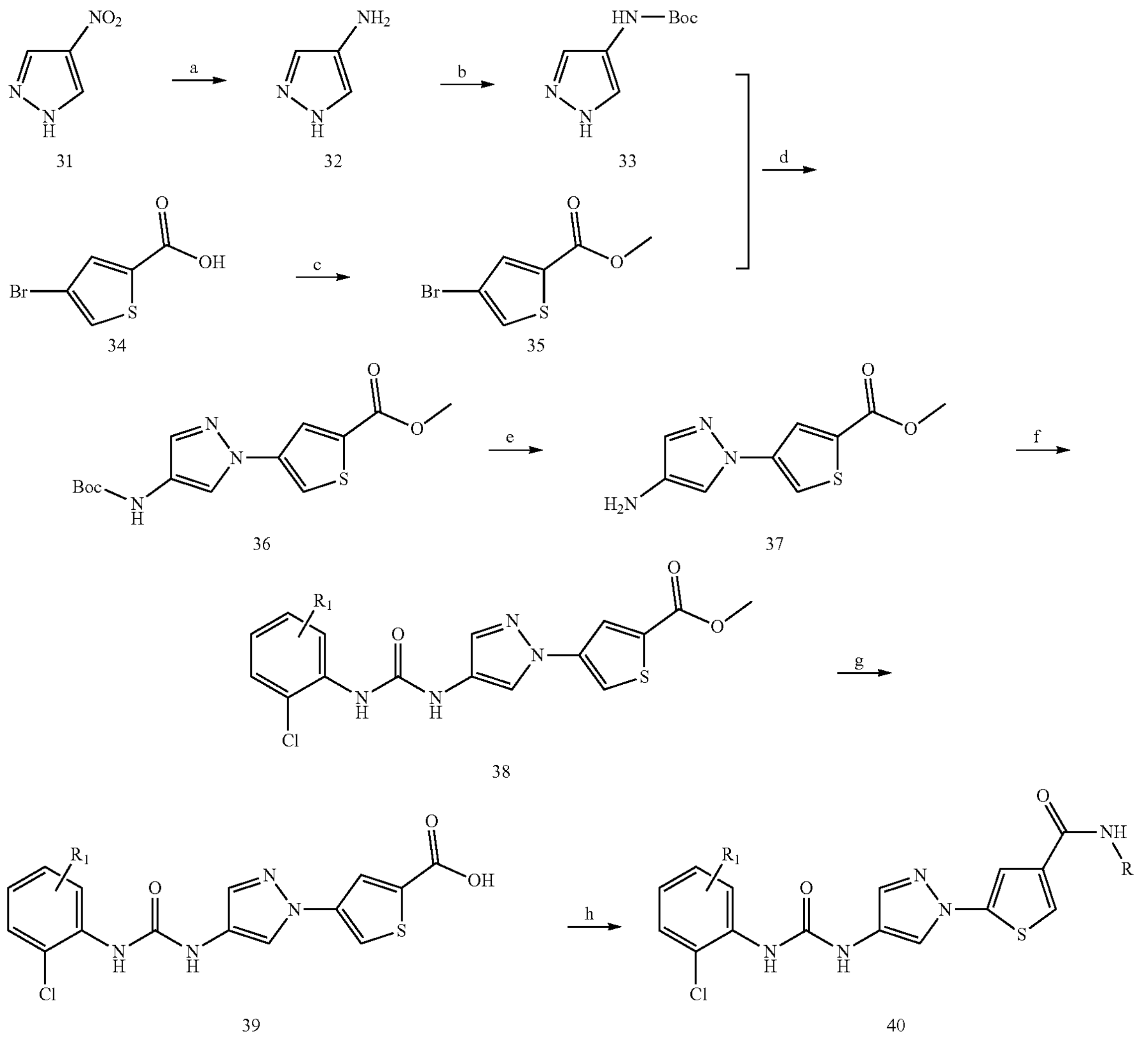

Referring to Scheme 1, 4-nitro-1H-pyrazole 31 is hydrogenated in the presence of Pd/c to produce 4-amino-1H-pyrazole 32 (step a). To a solution of compound 32 was added $Boc_2O$ (step b) to produce tert-butyl 1H-pyrazol-4-ylcarbamate 33.

In a separate reaction, 4-bromothiophene-2-carboxylic acid 34 was converted to methyl 4-bromothiophene-2-carboxylate 35 (step c). Tert-butyl 1H-pyrazol-4-ylcarbamate 33 and methyl 4-bromothiophene-2-carboxylate 35 are coupled to one another in the presence of CuI to produce methyl 4-(4-(tert-butoxycarbonylamino)-1H-pyrazol-1-yl)thiophene-2-carboxylate 36 (step d). Compound 36 is mixed with an acid to remove the Boc group and produce methyl 4-(4-amino-1H-pyrazol-1-yl)thiophene-2-carboxylate 37 (step e). Compound 37 was reacted with an aniline derivative (e.g., 2-chloroaniline or a substituted compound thereof) to produce compound 38 (step f). Compound 38 is next hydrolyzed to produce the acid compound 39 (step g). Finally, compound 39 is converted to an amide 40 by reacting compound 39 with an amine (step h).

Compounds having the structure 40 are those described herein. However, different starting materials and reagents can be used to vary the type and degree of substitution of the compounds. For example, the thiophene compound 34 can be substituted with one or more alkyl groups. Alternatively, the bromo group in thiophene 34 can be at other positions of the ring besides the 3-position. In other aspects, different aniline compounds can be reacted with compound 37 to vary the substitution of the phenyl ring. The Examples provide non-limiting procedures for making and purifying the compounds in Scheme 1.

Pharmaceutical Compositions

In various aspects, the present disclosure relates to pharmaceutical compositions comprising a therapeutically effective amount of at least one disclosed compound, at least one product of a disclosed method, or a pharmaceutically acceptable salt thereof. As used herein, "pharmaceutically-acceptable carriers" means one or more of a pharmaceutically acceptable diluents, preservatives, antioxidants, solubilizers, emulsifiers, coloring agents, releasing agents, coating agents, sweetening, flavoring and perfuming agents, and adjuvants. The disclosed pharmaceutical compositions can be conveniently presented in unit dosage form and prepared by any of the methods well known in the art of pharmacy and pharmaceutical sciences.

In a further aspect, the disclosed pharmaceutical compositions comprise a therapeutically effective amount of at least one disclosed compound, at least one product of a disclosed method, or a pharmaceutically acceptable salt thereof as an active ingredient, a pharmaceutically acceptable carrier, optionally one or more other therapeutic agent, and optionally one or more adjuvant. The disclosed pharmaceutical compositions include those suitable for oral, rectal, topical, pulmonary, nasal, and parenteral administration, although the most suitable route in any given case will depend on the particular host, and nature and severity of the conditions for which the active ingredient is being administered. In a further aspect, the disclosed pharmaceutical composition can be formulated to allow administration orally, nasally, via inhalation, parenterally, paracancerally, transmucosally, transdermally, intramuscularly, intravenously, intradermally, subcutaneously, intraperitonealy, intraventricularly, intracranially and intratumorally.

As used herein, "parenteral administration" includes administration by bolus injection or infusion, as well as administration by intravenous, intramuscular, intraarterial, intrathecal, intracapsular, intraorbital, intracardiac, intradermal, intraperitoneal, transtracheal, subcutaneous, subcuticular, intraarticular, subcapsular subarachnoid, intraspinal, epidural and intrasternal injection and infusion.

In various aspects, the present disclosure also relates to a pharmaceutical composition comprising a pharmaceutically acceptable carrier or diluent and, as active ingredient, a therapeutically effective amount of a disclosed compound, a product of a disclosed method of making, a pharmaceutically acceptable salt, a hydrate thereof, a solvate thereof, a polymorph thereof, or a stereochemically isomeric form thereof. In a further aspect, a disclosed compound, a product of a disclosed method of making, a pharmaceutically acceptable salt, a hydrate thereof, a solvate thereof, a polymorph thereof, or a stereochemically isomeric form thereof, or any subgroup or combination thereof may be formulated into various pharmaceutical forms for administration purposes.

Pharmaceutically acceptable salts can be prepared from pharmaceutically acceptable non-toxic bases or acids. For therapeutic use, salts of the disclosed compounds are those wherein the counter ion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are contemplated by the present disclosure. Pharmaceutically acceptable acid and base addition salts are meant to comprise the therapeutically active non-toxic acid and base addition salt forms which the disclosed compounds are able to form.

In various aspects, a disclosed compound comprising an acidic group or moiety, e.g., a carboxylic acid group, can be used to prepare a pharmaceutically acceptable salt. For example, such a disclosed compound may comprise an isolation step comprising treatment with a suitable inorganic or organic base. In some cases, it may be desirable in practice to initially isolate a compound from the reaction mixture as a pharmaceutically unacceptable salt and then simply convert the latter back to the free acid compound by treatment with an acidic reagent, and subsequently convert the free acid to a pharmaceutically acceptable base addition salt. These base addition salts can be readily prepared using conventional techniques, e.g., by treating the corresponding acidic compounds with an aqueous solution containing the desired pharmacologically acceptable cations and then evaporating the resulting solution to dryness, preferably under reduced pressure. Alternatively, they also can be prepared by mixing lower alkanolic solutions of the acidic compounds and the desired alkali metal alkoxide together, and then evaporating the resulting solution to dryness in the same manner as before.

Bases which can be used to prepare the pharmaceutically acceptable base-addition salts of the base compounds are those which can form non-toxic base-addition salts, i.e., salts containing pharmacologically acceptable cations such as, alkali metal cations (e.g., lithium, potassium and sodium), alkaline earth metal cations (e.g., calcium and magnesium), ammonium or other water-soluble amine addition salts such as N-methylglucamine-(meglumine), lower alkanolammonium and other such bases of organic amines. In a further aspect, derived from pharmaceutically acceptable organic non-toxic bases include primary, secondary, and tertiary amines, as well as cyclic amines and substituted amines such as naturally occurring and synthesized substituted amines. In various aspects, such pharmaceutically acceptable organic non-toxic bases include, but are not limited to, ammonia, methylamine, ethylamine, propylamine, isopropylamine, any of the four butylamine isomers, betaine, caffeine, choline, dimethylamine, diethylamine, diethanolamine, dipropylamine, diisopropylamine, di-n-butylamine, N,N'-dibenzylethylenediamine, pyrrolidine, piperidine, morpholine, trimethylamine, triethylamine, tripropylamine, tromethamine, 2-diethylaminoethanol, 2-dimethylaminoethanol, ethanolamine, quinuclidine, pyridine, quinoline and isoquinoline; benzathine, N-methyl-D-glucamine, ethylenediamine, N-ethylmorpholine, N-ethylpiperidine, glucamine, glucosamine, methylglucamine, morpholine, piperazine, piperidine, polyamine resins, procaine, purines, theobromine, hydrabamine salts, and salts with amino acids such as, for example, histidine, arginine, lysine and the like. The foregoing salt forms can be converted by treatment with acid back into the free acid form.

In various aspects, a disclosed compound comprising a protonatable group or moiety, e.g., an amino group, can be used to prepare a pharmaceutically acceptable salt. For example, such a disclosed compound may comprise an isolation step comprising treatment with a suitable inorganic or organic acid. In some cases, it may be desirable in practice to initially isolate a compound from the reaction mixture as a pharmaceutically unacceptable salt and then simply convert the latter back to the free base compound by treatment with a basic reagent, and subsequently convert the free base to a pharmaceutically acceptable acid addition salt. These acid addition salts can be readily prepared using conventional techniques, e.g., by treating the corresponding basic compounds with an aqueous solution containing the desired pharmacologically acceptable anions and then evaporating the resulting solution to dryness, preferably under reduced pressure. Alternatively, they also can be prepared by treating the free base form of the disclosed compound with a suitable pharmaceutically acceptable non-toxic inorganic or organic acid.

Acids which can be used to prepare the pharmaceutically acceptable acid-addition salts of the base compounds are those which can form non-toxic acid-addition salts, i.e., salts containing pharmacologically acceptable anions formed from their corresponding inorganic and organic acids. Exemplary, but non-limiting, inorganic acids include hydrochloric hydrobromic, sulfuric, nitric, phosphoric and the like. Exemplary, but non-limiting, organic acids include acetic, benzenesulfonic, benzoic, camphorsulfonic, citric, ethanesulfonic, fumaric, gluconic, glutamic, isethionic, lactic, maleic, malic, mandelicmethanesulfonic, mucic, pamoic, pantothenic, succinic, tartaric, p-toluenesulfonic acid and the like. In a further aspect, the acid-addition salt comprises an anion formed from hydrobromic, hydrochloric, maleic, phosphoric, sulfuric, and tartaric acids.

In practice, the compounds of the present disclosure, or pharmaceutically acceptable salts thereof, of the present disclosure can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the present disclosure, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

It is especially advantageous to formulate the aforementioned pharmaceutical compositions in unit dosage form for ease of administration and uniformity of dosage. The term “unit dosage form,” as used herein, refers to physically discrete units suitable as unitary dosages, each unit containing a predetermined quantity of active ingredient calculated to produce the desired therapeutic effect in association with the required pharmaceutical carrier. That is, a “unit dosage form” is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets (including scored or coated tablets), capsules or pills for oral administration; single dose vials for injectable solutions or suspension; suppositories for rectal administration; powder packets; wafers; and segregated multiples thereof. This list of unit dosage forms is not intended to be limiting in any way, but merely to represent typical examples of unit dosage forms.

The pharmaceutical compositions disclosed herein comprise a compound of the present disclosure (or pharmaceutically acceptable salts thereof) as an active ingredient, a pharmaceutically acceptable carrier, and optionally one or more additional therapeutic agents. In various aspects, the disclosed pharmaceutical compositions can include a pharmaceutically acceptable carrier and a disclosed compound, or a pharmaceutically acceptable salt thereof. In a further aspect, a disclosed compound, or pharmaceutically acceptable salt thereof, can also be included in a pharmaceutical composition in combination with one or more other therapeutically active compounds. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Techniques and compositions for making dosage forms useful for materials and methods described herein are described, for example, in the following references: Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington’s Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

The compounds described herein are typically to be administered in admixture with suitable pharmaceutical diluents, excipients, extenders, or carriers (termed herein as a pharmaceutically acceptable carrier, or a carrier) suitably selected with respect to the intended form of administration and as consistent with conventional pharmaceutical practices. The deliverable compound will be in a form suitable for oral, rectal, topical, intravenous injection or parenteral administration. Carriers include solids or liquids, and the type of carrier is chosen based on the type of administration being used. The compounds may be administered as a dosage that has a known quantity of the compound.

Because of the ease in administration, oral administration can be a preferred dosage form, and tablets and capsules represent the most advantageous oral dosage unit forms in which case solid pharmaceutical carriers are obviously employed. However, other dosage forms may be suitable depending upon clinical population (e.g., age and severity of clinical condition), solubility properties of the specific disclosed compound used, and the like. Accordingly, the disclosed compounds can be used in oral dosage forms such as pills, powders, granules, elixirs, tinctures, suspensions, syrups, and emulsions. In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such as powders, capsules and tablets. Because of their ease of administration, tablets and capsules are the preferred oral dosage units whereby solid pharmaceutical carriers are employed. Optionally, tablets can be coated by standard aqueous or nonaqueous techniques.

The disclosed pharmaceutical compositions in an oral dosage form can comprise one or more pharmaceutical excipient and/or additive. Non-limiting examples of suitable excipients and additives include gelatin, natural sugars such as raw sugar or lactose, lecithin, pectin, starches (for example corn starch or amylose), dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated, aliphatic oxyalcohols, for example methyl oxypropyl cellulose, methyl cellulose, hydroxypropyl methyl cellulose, hydroxypropyl methyl cellulose phthalate), fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also optionally hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10-18 carbon atoms) with monovalent aliphatic alcohols (1 to 20 carbon atoms) or multivalent alcohols such as glycols, glycerol, diethylene glycol, pentacrythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with C1-C12-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances useful in preparing an oral dosage form are those that cause disintegration (so-called disintegrants), such as: cross-linked polyvinyl pyrrolidone, sodium carboxymethyl starch, sodium carboxymethyl cellulose or microcrystalline cellulose. Conventional coating substances may also be used to produce the oral dosage form. Those that may for example be considered are: polymerizates as well as copolymerizates of acrylic acid and/or methacrylic acid and/or their esters; copolymerizates of acrylic and methacrylic acid esters with a lower ammonium group content (for example Eudragit® RS), copolymerizates of acrylic and methacrylic acid esters and trimethyl ammonium methacrylate (for example Eudragit® RL); polyvinyl acetate; fats, oils, waxes, fatty alcohols; hydroxypropyl methyl cellulose phthalate or acetate succinate; cellulose acetate phthalate, starch acetate phthalate as well as polyvinyl acetate phthalate, carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginine.

Plasticizing agents that may be considered as coating substances in the disclosed oral dosage forms are: citric and tartaric acid esters (acetyl-triethyl citrate, acetyl tributyl-, tributyl-, triethyl-citrate); glycerol and glycerol esters (glycerol diacetate, -triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and diburylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbar 50); sorbitan monooleate.

Moreover, suitable binders, lubricants, disintegrating agents, coloring agents, flavoring agents, flow-inducing agents, and melting agents may be included as carriers. The pharmaceutical carrier employed can be, for example, a solid, liquid, or gas. Examples of solid carriers include, but are not limited to, lactose, terra alba, sucrose, glucose, methylcellulose, dicalcium phosphate, calcium sulfate, mannitol, sorbitol talc, starch, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In various aspects, a binder can include, for example, starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. In a further aspect, a disintegrator can include, for example, starch, methyl cellulose, agar, bentonite, xanthan gum, and the like.

In various aspects, an oral dosage form, such as a solid dosage form, can comprise a disclosed compound that is attached to polymers as targetable drug carriers or as a prodrug. Suitable biodegradable polymers useful in achieving controlled release of a drug include, for example, polylactic acid, polyglycolic acid, copolymers of polylactic and polyglycolic acid, caprolactones, polyhydroxy butyric acid, polyorthoesters, polyacetals, polydihydropyrans, polycyanoacylates, and hydrogels, preferably covalently crosslinked hydrogels.

Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing a disclosed compound can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent. Molded tablets can be made by molding in a suitable machine, a mixture of the powdered compound moistened with an inert liquid diluent.

In various aspects, a solid oral dosage form, such as a tablet, can be coated with an enteric coating to prevent ready decomposition in the stomach. In various aspects, enteric coating agents include, but are not limited to, hydroxypropylmethylcellulose phthalate, methacrylic acid-methacrylic acid ester copolymer, polyvinyl acetate-phthalate and cellulose acetate phthalate. Akihiko Hasegawa "Application of solid dispersions of Nifedipine with enteric coating agent to prepare a sustained-release dosage form" Chem. Pharm. Bull. 33:1615-1619 (1985). Various enteric coating materials may be selected on the basis of testing to achieve an enteric coated dosage form designed ab initio to have a preferable combination of dissolution time, coating thicknesses and diametral crushing strength (e.g., see S. C. Porter et al. "The Properties of Enteric Tablet Coatings Made From Polyvinyl Acetate-phthalate and Cellulose acetate Phthalate", J. Pharm. Pharmacol. 22:42p (1970)). In a further aspect, the enteric coating may comprise hydroxypropylmethylcellulose phthalate, methacrylic acid-methacrylic acid ester copolymer, polyvinyl acetate-phthalate and cellulose acetate phthalate.

In various aspects, an oral dosage form can be a solid dispersion with a water soluble or a water insoluble carrier. Examples of water soluble or water insoluble carrier include, but are not limited to, polyethylene glycol, polyvinylpyrrolidone, hydroxypropylmethyl-cellulose, phosphatidylcholine, polyoxyethylene hydrogenated castor oil, hydroxypropylmethylcellulose phthalate, carboxymethylethylcellulose, or hydroxypropylmethylcellulose, ethyl cellulose, or stearic acid.

In various aspects, an oral dosage form can be in a liquid dosage form, including those that are ingested, or alternatively, administered as a mouth wash or gargle. For example, a liquid dosage form can include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the present disclosure may also be in the form of oil-in-water emulsions, which may also contain excipients such as sweetening and flavoring agents.

For the preparation of solutions or suspensions it is, for example, possible to use water, particularly sterile water, or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of a liquid dosage form such as a drinkable solutions, the following substances may be used as stabilizers or solubilizers: lower aliphatic mono- and multivalent alcohols with 2-4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic C1-C6-carboxylic acids with ammonia or primary, secondary or tertiary C1-C4-amines or C1-C4-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids.

In preparing the disclosed liquid dosage form can comprise solubilizers and emulsifiers such as the following non-limiting examples can be used: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20. Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride). Examples of oleotriglycerides are olive oil, peanut oil, castor oil, sesame oil, cottonseed oil, corn oil. See also Dr. H. P. Fiedler "Lexikon der Hillsstoffe für Pharmazie, Kostnetik und angrenzende Gebiete" 1971, pages 191-195.

In various aspects, a liquid dosage form can further comprise preservatives, stabilizers, buffer substances, flavor correcting agents, sweeteners, colorants, antioxidants and complex formers and the like. Complex formers which may be for example be considered are: chelate formers such as ethylene diamine retrascetic acid, nitrilotriacetic acid, diethylene triamine pentacetic acid and their salts.

It may optionally be necessary to stabilize a liquid dosage form with physiologically acceptable bases or buffers to a pH range of approximately 6 to 9. Preference may be given to as neutral or weakly basic a pH value as possible (up to pH 8).

In order to enhance the solubility and/or the stability of a disclosed compound in a disclosed liquid dosage form, a parenteral injection form, or an intravenous injectable form, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the present disclosure in pharmaceutical compositions.

In various aspects, a disclosed liquid dosage form, a parenteral injection form, or an intravenous injectable form can further comprise liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions of the present disclosure are suitable for injection, such as parenteral administration, such as intravenous, intramuscular, or subcutaneous administration. Pharmaceutical compositions for injection can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for parenteral administration can include sterile aqueous or oleaginous solutions, suspensions, or dispersions. Furthermore, the compositions can be in the form of sterile powders for the extemporaneous preparation of such sterile injectable solutions or dispersions. In some aspects, the final injectable form is sterile and must be effectively fluid for use in a syringe. The pharmaceutical compositions should be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Injectable solutions, for example, can be prepared in which the carrier comprises saline solution, glucose solution or a mixture of saline and glucose solution. Injectable suspensions may also be prepared in which case appropriate liquid carriers, suspending agents and the like may be employed. In some aspects, a disclosed parenteral formulation can comprise about 0.01-0.1 M, e.g. about 0.05 M, phosphate buffer. In a further aspect, a disclosed parenteral formulation can comprise about 0.9% saline.

In various aspects, a disclosed parenteral pharmaceutical composition can comprise pharmaceutically acceptable carriers such as aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include but not limited to water, alcoholic/aqueous solutions, emulsions or suspensions, including saline and buffered media. Parenteral vehicles can include mannitol, normal serum albumin, sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like. In a further aspect, a disclosed parenteral pharmaceutical composition can comprise may contain minor amounts of additives such as substances that enhance isotonicity and chemical stability, e.g., buffers and preservatives. Also contemplated for injectable pharmaceutical compositions are solid form preparations that are intended to be converted, shortly before use, to liquid form preparations. Furthermore, other adjuvants can be included to render the formulation isotonic with the blood of the subject or patient.

In addition to the pharmaceutical compositions described herein above, the disclosed compounds can also be formulated as a depot preparation. Such long acting formulations can be administered by implantation (e.g., subcutaneously or intramuscularly) or by intramuscular injection. Thus, for example, the compounds can be formulated with suitable polymeric or hydrophobic materials (e.g., as an emulsion in an acceptable oil) or ion exchange resins, or as sparingly soluble derivatives, e.g., as a sparingly soluble salt.

Pharmaceutical compositions of the present disclosure can be in a form suitable for topical administration. As used herein, the phrase "topical application" means administration onto a biological surface, whereby the biological surface includes, for example, a skin area (e.g., hands, forearms, elbows, legs, face, nails, anus and genital areas) or a mucosal membrane. By selecting the appropriate carrier and optionally other ingredients that can be included in the composition, as is detailed herein below, the compositions of the present disclosure may be formulated into any form typically employed for topical application. A topical pharmaceutical composition can be in a form of a cream, an ointment, a paste, a gel, a lotion, milk, a suspension, an aerosol, a spray, foam, a dusting powder, a pad, and a patch. Further, the compositions can be in a form suitable for use in transdermal devices. These formulations can be prepared, utilizing a compound of the present disclosure, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

Ointments are semisolid preparations, typically based on petrolatum or petroleum derivatives. The specific ointment base to be used is one that provides for optimum delivery for the active agent chosen for a given formulation, and, preferably, provides for other desired characteristics as well (e.g., emollience). As with other carriers or vehicles, an ointment base should be inert, stable, nonirritating and nonsensitizing. As explained in Remington: The Science and Practice of Pharmacy, 19th Ed., Easton, Pa.: Mack Publishing Co. (1995), pp. 1399-1404, ointment bases may be grouped in four classes: oleaginous bases; emulsifiable bases; emulsion bases; and water-soluble bases. Oleaginous ointment bases include, for example, vegetable oils, fats obtained from animals, and semisolid hydrocarbons obtained from petroleum. Emulsifiable ointment bases, also known as absorbent ointment bases, contain little or no water and include, for example, hydroxystearin sulfate, anhydrous lanolin and hydrophilic petrolatum. Emulsion ointment bases are either water-in-oil (W/O) emulsions or oil-in-water (O/W) emulsions, and include, for example, cetyl alcohol, glyceryl monostearate, lanolin and stearic acid. Preferred water-soluble ointment bases are prepared from polyethylene glycols of varying molecular weight.

Lotions are preparations that are to be applied to the skin surface without friction. Lotions are typically liquid or semiliquid preparations in which solid particles, including the active agent, are present in a water or alcohol base. Lotions are typically preferred for treating large body areas, due to the ease of applying a more fluid composition. Lotions are typically suspensions of solids, and oftentimes comprise a liquid oily emulsion of the oil-in-water type. It is generally necessary that the insoluble matter in a lotion be finely divided. Lotions typically contain suspending agents to produce better dispersions as well as compounds useful for localizing and holding the active agent in contact with the skin, such as methylcellulose, sodium carboxymethylcellulose, and the like.

Creams are viscous liquids or semisolid emulsions, either oil-in-water or water-in-oil. Cream bases are typically water-washable, and contain an oil phase, an emulsifier and an aqueous phase. The oil phase, also called the "internal" phase, is generally comprised of petrolatum and/or a fatty alcohol such as cetyl or stearyl alcohol. The aqueous phase typically, although not necessarily, exceeds the oil phase in volume, and generally contains a humectant. The emulsifier in a cream formulation is generally a nonionic, anionic, cationic or amphoteric surfactant. Reference may be made to Remington: The Science and Practice of Pharmacy, supra, for further information.

Pastes are semisolid dosage forms in which the bioactive agent is suspended in a suitable base. Depending on the nature of the base, pastes are divided between fatty pastes or those made from a single-phase aqueous gel. The base in a fatty paste is generally petrolatum, hydrophilic petrolatum and the like. The pastes made from single-phase aqueous gels generally incorporate carboxymethylcellulose or the like as a base. Additional reference may be made to Remington: The Science and Practice of Pharmacy, for further information.

Gel formulations are semisolid, suspension-type systems. Single-phase gels contain organic macromolecules distributed substantially uniformly throughout the carrier liquid, which is typically aqueous, but also, preferably, contain an alcohol and, optionally, an oil. Preferred organic macromolecules, i.e., gelling agents, are crosslinked acrylic acid polymers such as the family of carbomer polymers, e.g., carboxypolyalkylenes that may be obtained commercially under the trademark Carbopol™. Other types of preferred polymers in this context are hydrophilic polymers such as polyethylene oxides, polyoxyethylene-polyoxypropylene copolymers and polyvinylalcohol; modified cellulose, such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Sprays generally provide the active agent in an aqueous and/or alcoholic solution which can be misted onto the skin for delivery. Such sprays include those formulated to provide for concentration of the active agent solution at the site of administration following delivery, e.g., the spray solution can be primarily composed of alcohol or other like volatile liquid in which the active agent can be dissolved. Upon delivery to the skin, the carrier evaporates, leaving concentrated active agent at the site of administration.

Foam compositions are typically formulated in a single or multiple phase liquid form and housed in a suitable container, optionally together with a propellant which facilitates the expulsion of the composition from the container, thus transforming it into a foam upon application. Other foam forming techniques include, for example the "Bag-in-a-can" formulation technique. Compositions thus formulated typically contain a low-boiling hydrocarbon, e.g., isopropane. Application and agitation of such a composition at the body temperature cause the isopropane to vaporize and generate the foam, in a manner similar to a pressurized aerosol foaming system. Foams can be water-based or aqueous alkanolic, but are typically formulated with high alcohol content which, upon application to the skin of a user, quickly evaporates, driving the active ingredient through the upper skin layers to the site of treatment.

Skin patches typically comprise a backing, to which a reservoir containing the active agent is attached. The reservoir can be, for example, a pad in which the active agent or composition is dispersed or soaked, or a liquid reservoir. Patches typically further include a frontal water permeable adhesive, which adheres and secures the device to the treated region. Silicone rubbers with self-adhesiveness can alternatively be used. In both cases, a protective permeable layer can be used to protect the adhesive side of the patch prior to its use. Skin patches may further comprise a removable cover, which serves for protecting it upon storage.

Examples of patch configuration which can be utilized with the present disclosure include a single-layer or multi-layer drug-in-adhesive systems which are characterized by the inclusion of the drug directly within the skin-contacting adhesive. In such a transdermal patch design, the adhesive not only serves to affix the patch to the skin, but also serves as the formulation foundation, containing the drug and all the excipients under a single backing film. In the multi-layer drug-in-adhesive patch a membrane is disposed between two distinct drug-in-adhesive layers or multiple drug-in-adhesive layers are incorporated under a single backing film.

Examples of pharmaceutically acceptable carriers that are suitable for pharmaceutical compositions for topical applications include carrier materials that are well-known for use in the cosmetic and medical arts as bases for e.g., emulsions, creams, aqueous solutions, oils, ointments, pastes, gels, lotions, milks, foams, suspensions, aerosols and the like, depending on the final form of the composition. Representative examples of suitable carriers according to the present disclosure therefore include, without limitation, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Other suitable carriers according to the present disclosure include, without limitation, alcohols, such as, for example, monohydric and polyhydric alcohols, e.g., ethanol, isopropanol, glycerol, sorbitol, 2-methoxyethanol, diethyleneglycol, ethylene glycol, hexyleneglycol, mannitol, and propylene glycol; ethers such as diethyl or dipropyl ether; polyethylene glycols and methoxypolyoxyethylenes (carbowaxes having molecular weight ranging from 200 to 20,000); polyoxyethylene glycerols, polyoxyethylene sorbitols, stearoyl diacetin, and the like.

Topical compositions of the present disclosure can, if desired, be presented in a pack or dispenser device, such as an FDA-approved kit, which may contain one or more unit dosage forms containing the active ingredient. The dispenser device may, for example, comprise a tube. The pack or dispenser device may be accompanied by instructions for administration. The pack or dispenser device may also be accompanied by a notice in a form prescribed by a governmental agency regulating the manufacture, use, or sale of pharmaceuticals, which notice is reflective of approval by the agency of the form of the compositions for human or veterinary administration. Such notice, for example, may include labeling approved by the U.S. Food and Drug Administration for prescription drugs or of an approved product insert. Compositions comprising the topical composition of the disclosure formulated in a pharmaceutically acceptable carrier may also be prepared, placed in an appropriate container, and labeled for treatment of an indicated condition.

Another patch system configuration which can be used by the present disclosure is a reservoir transdermal system design which is characterized by the inclusion of a liquid compartment containing a drug solution or suspension separated from the release liner by a semi-permeable membrane and adhesive. The adhesive component of this patch system can either be incorporated as a continuous layer between the membrane and the release liner or in a concentric configuration around the membrane. Yet another patch system configuration which can be utilized by the present disclosure is a matrix system design which is characterized by the inclusion of a semisolid matrix containing a drug solution or suspension which is in direct contact with the release liner. The component responsible for skin adhesion is incorporated in an overlay and forms a concentric configuration around the semisolid matrix.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

Pharmaceutical compositions containing a compound of the present disclosure, and/or pharmaceutically acceptable salts thereof, can also be prepared in powder or liquid concentrate form.

The pharmaceutical composition (or formulation) may be packaged in a variety of ways. Generally, an article for distribution includes a container that contains the pharmaceutical composition in an appropriate form. Suitable containers are well known to those skilled in the art and include materials such as bottles (plastic and glass), sachets, foil blister packs, and the like. The container may also include a tamper proof assemblage to prevent indiscreet access to the contents of the package. In addition, the container typically has deposited thereon a label that describes the contents of the container and any appropriate warnings or instructions.

The disclosed pharmaceutical compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Pharmaceutical compositions comprising a disclosed compound formulated in a compatible pharmaceutical carrier may also be prepared, placed in an appropriate container, and labeled for treatment of an indicated condition.

The exact dosage and frequency of administration depends on the particular disclosed compound, a product of a disclosed method of making, a pharmaceutically acceptable salt, solvate, or polymorph thereof, a hydrate thereof, a solvate thereof, a polymorph thereof, or a stereochemically isomeric form thereof; the particular condition being treated and the severity of the condition being treated; various factors specific to the medical history of the subject to whom the dosage is administered such as the age; weight, sex, extent of disorder and general physical condition of the particular subject, as well as other medication the individual may be taking; as is well known to those skilled in the art. Furthermore, it is evident that said effective daily amount may be lowered or increased depending on the response of the treated subject and/or depending on the evaluation of the physician prescribing the compounds of the present disclosure.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

In the treatment conditions which require inhibition of a kinase, an appropriate dosage level will generally be about 0.01 to 1000 mg per kg patient body weight per day and can be administered in single or multiple doses. In various aspects, the dosage level will be about 0.1 to about 500 mg/kg per day, about 0.1 to 250 mg/kg per day, or about 0.5 to 100 mg/kg per day. A suitable dosage level can be about 0.01 to 1000 mg/kg per day, about 0.01 to 500 mg/kg per day, about 0.01 to 250 mg/kg per day, about 0.05 to 100 mg/kg per day, or about 0.1 to 50 mg/kg per day. Within this range the dosage can be 0.05 to 0.5, 0.5 to 5.0 or 5.0 to 50 mg/kg per day. For oral administration, the compositions are preferably provided in the form of tablets containing 1.0 to 1000 mg of the active ingredient, particularly 1.0, 5.0, 10, 15, 20, 25, 50, 75, 100, 150, 200, 250, 300, 400, 500, 600, 750, 800, 900 and 1000 mg of the active ingredient for the symptomatic adjustment of the dosage of the patient to be treated. The compound can be administered on a regimen of 1 to 4 times per day, preferably once or twice per day. This dosing regimen can be adjusted to provide the optimal therapeutic response.

Such unit doses as described hereinabove and hereinafter can be administered more than once a day, for example, 2, 3, 4, 5 or 6 times a day. In various aspects, such unit doses can be administered 1 or 2 times per day, so that the total dosage for a 70 kg adult is in the range of 0.001 to about 15 mg per kg weight of subject per administration. In a further aspect, dosage is 0.01 to about 1.5 mg per kg weight of subject per administration, and such therapy can extend for a number of weeks or months, and in some cases, years. It will be understood, however, that the specific dose level for any particular patient will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

A typical dosage can be one 1 mg to about 100 mg tablet or 1 mg to about 300 mg taken once a day, or, multiple times per day, or one time-release capsule or tablet taken once a day and containing a proportionally higher content of active ingredient. The time-release effect can be obtained by capsule materials that dissolve at different pH values, by capsules that release slowly by osmotic pressure, or by any other known means of controlled release.

It can be necessary to use dosages outside these ranges in some cases as will be apparent to those skilled in the art. Further, it is noted that the clinician or treating physician will know how and when to start, interrupt, adjust, or terminate therapy in conjunction with individual patient response.

The present disclosure is further directed to a method for the manufacture of a medicament for modulating kinase activity (e.g., treatment of one or more central nervous system disorders associated with JNK3 dysfunction) in mammals (e.g., humans) comprising combining one or more disclosed compounds, products, or compositions with a pharmaceutically acceptable carrier or diluent. Thus, in one aspect, the present disclosure further relates to a method for manufacturing a medicament comprising combining at least one disclosed compound or at least one disclosed product with a pharmaceutically acceptable carrier or diluent.

The disclosed pharmaceutical compositions can further comprise other therapeutically active compounds, which are usually applied in the treatment of the above mentioned pathological or clinical conditions.

It is understood that the disclosed compositions can be prepared from the disclosed compounds. It is also understood that the disclosed compositions can be employed in the disclosed methods of using.

As already mentioned, the present disclosure relates to a pharmaceutical composition comprising a therapeutically effective amount of a disclosed compound, a product of a disclosed method of making, a pharmaceutically acceptable salt, a hydrate thereof, a solvate thereof, a polymorph thereof, and a pharmaceutically acceptable carrier. Additionally, the present disclosure relates to a process for preparing such a pharmaceutical composition, characterized in that a pharmaceutically acceptable carrier is intimately mixed with a therapeutically effective amount of a compound according to the present disclosure.

As already mentioned, the present disclosure also relates to a pharmaceutical composition comprising a disclosed compound, a product of a disclosed method of making, a pharmaceutically acceptable salt, a hydrate thereof, a solvate thereof, a polymorph thereof, and one or more other drugs in the treatment, prevention, control, amelioration, or reduction of risk of diseases or conditions for a disclosed compound or the other drugs may have utility as well as to the use of such a composition for the manufacture of a medicament. The present disclosure also relates to a combination of disclosed compound, a product of a disclosed method of making, a pharmaceutically acceptable salt, a hydrate thereof, a solvate thereof, a polymorph thereof, and a JNK3 inhibitor. The present disclosure also relates to such a combination for use as a medicine. The present disclosure also relates to a product comprising (a) disclosed compound, a product of a disclosed method of making, a pharmaceutically acceptable salt, a hydrate thereof, a solvate thereof, a polymorph thereof, and (b) an additional therapeutic agent active on the central nervous system, as a combined preparation for simultaneous, separate or sequential use in the treatment or prevention of a condition in a mammal, including a human, the treatment or prevention of which is affected or facilitated by the modulatory effect of the disclosed compound and the additional therapeutic agent. The different drugs of such a combination or product may be combined in a single preparation together with pharmaceutically acceptable carriers or diluents, or they may each be present in a separate preparation together with pharmaceutically acceptable carriers or diluents.

Methods of Using the Compounds

In a further aspect, the present disclosure provides methods of treatment comprising administration of a therapeutically effective amount of a disclosed compound or pharmaceutical composition as disclosed herein above to a subject in need thereof. In particular, the disclosed compounds and disclosed pharmaceutical compositions can be used in methods of treating a disease or disorder that are associated with increased, aberrant, or dysfunctional levels of c-Jun N-terminal kinase 1 (JNK1) c-Jun N-terminal kinase 2 (JNK2), c-Jun N-terminal kinase 3 (JNK3), kinase p38a, ABL1, ABL2, DDR1, DDR2, CK1, MAP4K, GCK, MINK1, HGK, TNIK activity in a neuron. That is, the disclosed compounds and disclosed pharmaceutical compositions can be used to inhibit specific kinase activity in a neuron, nervous tissue, or organism to provide a clinical or therapeutic benefit to a subject which has been determined to or been diagnosed to have increased, aberrant, or dysfunctional levels of the specific activity. In one aspect, the compounds described herein can selectively inhibit one kinase while not affecting the activity of other kinases. For example, the compounds disclosed herein selectively inhibit JNK3 while not affecting JNK1 and P38. In an alternative aspect, the compounds disclosed herein also inhibit JNK1 and/or P38 but to a significantly lesser degree than with respect to JNK3.

The compounds described herein have good bioavailability. For example, the compounds described herein can be administered orally and delivered into the brain (i.e., penetrate the blood-brain barrier). These features make the compounds described herein useful in central nervous system applications.

In some aspects of the disclosed methods, the subject has been diagnosed with a need for treatment prior to the administering step. In some aspects of the disclosed method, the subject has been diagnosed with a disorder treatable by inhibition of the kinase and/or a need for inhibition of the kinase prior to the administering step. In some aspects of the disclosed method, the subject has been diagnosed with a cancer, a neurodegenerative disorder, a disorder of the central or peripheral nervous system, organ failure, or the like, or may be at risk for developing such a disorder prior to the administering step. In some aspects of the disclosed methods, the subject has been identified with a need for treatment prior to the administering step.

The disclosed compounds can be used as single agents or in combination with one or more other drugs in the treatment, prevention, control, amelioration, or reduction of risk of the aforementioned diseases, disorders, and conditions for which the disclosed compounds and other drugs have utility, where the combination of drugs together is safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound will be more efficacious than either as a single agent.

In one aspect, the compounds described herein inhibit the activity of JNK3. JNK3 is an enzyme that catalyzes phosphorylation of c-Jun on Ser-63 and Ser-73 within its transcription activation domain following activation by stress stimuli including, but not limited to, cytokines, ultraviolet irradiation, gamma irradiation, heat shock, and osmotic shock. JNK genes are activated when threonine and tyrosine residues in a Thr-Pro-Tyr motif in subdomain VIII are phosphorylated and can be inactivate by Ser/Thr and Tyr protein phosphatases. This pathway is believed to contribute to inflammatory responses in mammals. In one aspect, the JNK3 pathway is a cell-death signaling pathway that controls response to a harmful extracellular stimulus such as those stress stimuli discussed above. In the case that DNA damage caused by the stimuli cannot be repaired, apoptosis must be activated through any of several methods including c-Jun phosphorylation which, in turn, activates transcription of pro-apoptotic genes.

JNK3 has a fold typical of other protein kinases and includes an ATP-binding site in a cleft between the N- and C-terminal domains. The ATP-binding site is well-ordered with a nucleotide-binding sequence having numerous glycine residues forming a β-strand-turn-β-strand structure. Unphosphorylated JNK3 has an open conformation wherein some catalytic residues are misaligned, thus likely accounting for low activity of unphosphorylated JNK3. JNK3 has two domains, an N-terminal domain that contains a catalytic lysine residue (Lys93) and a C-terminal domain containing a disordered loop (i.e., the "DFG loop") just before the previously-described nucleotide-binding sequence. The remainder of the protein is primarily α-helical in structure with isolated β-sheet structure somewhat distal from the substrate protein binding site (see Xie, X. et al., Structure, 1998, 6:983-991).

In an organism, JNK3 is highly expressed and activated in Alzheimer's disease patients and is involved in neuronal ischemic apoptosis as well as neuronal differentiation. Activated JNK3 phosphorylates numerous proteins including mitochondrial proteins, leading to aberrant mitochondrial function in addition to apoptosis-related functions already mentioned.

Inhibition of JNK3 results in inactivation or lower activation levels of phosphorylation of target proteins such as c-Jun, which in turn decreases the production of other apoptosis-related gene products in the JNK3 signaling cascade. This, in turn, results in decreased levels of neuronal cell death in response to stress signals and inflammation. Therefore, inhibitors of JNK3 show beneficial anti-apoptosis, anti-inflammatory, and neuroprotective effects in human diseases.

Accordingly, in various aspects, the present disclosure pertains to methods of treating a variety of diseases or disorders, including, but not limited to, cancers, diseases of the central and peripheral nervous system, immune and inflammatory diseases, neurodegenerative disorders, organ failure, and the like. In a further aspect, the present disclosure pertains to methods of treating a variety of diseases or disorders, including, but not limited to, injuries to the nervous system, such as spinal cord injury, traumatic brain injury, and stroke; neurodegenerative conditions, such as Parkinson's disease, Huntington's disease, and Alzheimer's disease; inflammatory diseases, such as multiple sclerosis and type-2 diabetes. In a still further aspect, the present disclosure pertains to methods of treating a variety of diseases or disorders, including, but not limited to, cancer, rheumatoid arthritis, vascular diseases, and other disorders resulting from excessive angiogenesis.

In a further aspect, the present disclosure pertains to methods for treating a cancer, a disease of the central and/or peripheral nervous system, an immune or inflammatory disease, a neurodegenerative disease, or organ failure via inhibition of one or more kinases described herein by administering to a subject in need of such treatment an effective amount of at least one disclosed compound or at least one disclosed pharmaceutical composition.

In a further aspect, the present disclosure pertains to methods for treating a cancer, a disease of the central and/or peripheral nervous system, an immune or inflammatory disease, a neurodegenerative disease, or organ failure via inhibition of one or more kinases described herein by administering to a patient in need of such treatment an effective amount of at least one disclosed compound or at least one disclosed pharmaceutical composition in combination (simultaneously or sequentially) with at least one other anti-inflammatory, neuroprotective, or anti-cancer agent.

Neurodegenerative diseases that can be treated by the disclosed compounds or disclosed pharmaceutical compositions include, but are not limited to, Alzheimer's disease, Huntington's disease, Parkinson's disease, epilepsy, stroke, amyotrophic lateral sclerosis (ALS), and spinal muscular atrophy (SMA), and deafness and glaucoma especially when caused by aberrant JNK3 activity in the associated cranial nerves. Other inflammatory conditions that can be treated by the disclosed compounds or disclosed pharmaceutical compositions include, but are not limited to, organ failure, cancers, and the like.

In various aspects, the disclosed compounds can be used in methods of treating a cancer, including a cancer comprising a mutation in the JNK3 gene. JNK3 gene is located on the long arm of chromosome 4 (4q), which is often lost in tumors. In fact, SNP of JNK3 gene was identified in brain tumor cell lines, which resulted in loss of JNK3 gene (Yoshida S, Fukino K, Harada H, Nagai H, Imoto I, et al. 2001. J Hum Genet 46: 182-7). Also in leukemia, JNK3 gene expression was downregulated in 82 tumor cell lines (Ying et al 2006 Leukemia 20: 1173-5). It is believed that the role of JNK1/2 in cancers is mainly due to their ability to activate c-jun by phosphorylation. For instance, fibroblasts without c-jun cannot be transformed by Ras (Johnson et al 1996 Mol Cell Biol 16: 4504-11).

In various aspects, the disclosed compounds can be used to augment or enhance regeneration after injury in the nervous system. DLK1 is an upstream kinase for JNK. It was shown that deleting DLK1 or inhibiting JNK pharmacologically improves regeneration of damaged axons in culture (Miller et al 2009 *Nat Neurosci* 12: 387-9). In the CNS, JNK1 and 3 are mainly responsible for the effect on degeneration (Yang et al 2015 Cell 160: 161-76).

In further aspects, the disclosed compounds or disclosed pharmaceutical compositions can act as modulators of apoptosis and, accordingly, can be useful in the treatment of cancer, viral infections (including but not limited to herpes viruses, poxvirus, Epstein-Barr virus, Sindbis virus, and adenoviruses), prevention of AIDS development in HIV-infected individuals, autoimmune diseases (including but not limited to systemic lupus erythematosus, autoimmune mediated glomerulonephritis, rheumatoid arthritis, psoriasis, inflammatory bowel disease, and autoimmune diabetes mellitus), neurodegenerative disorders not already mentioned (including retinitis pigmentosa and cerebellar degeneration), myelodysplastic syndromes, aplastic anemia, ischemic injury associated with myocardial infarctions, reperfusion injury, arrhythmia, atherosclerosis, toxin-induced or alcohol-related liver diseases, hematological diseases (including but not limited to chronic anemia and aplastic anemia), degenerative diseases of the musculoskeletal system (including but not limited to osteoporosis and arthritis), aspirin-sensitive rhinosinusitis, cystic fibrosis, multiple sclerosis, kidney diseases, and cancer pain.

In further aspects, the disclosed compounds and disclosed pharmaceutical compositions can also be combined with other active compounds in the treatment of diseases where the inhibition of one or more kinases described herein is known to show beneficial effect.

In a further aspect, the disclosed compounds and disclosed pharmaceutical compositions can be used in the treatment of a variety of inflammatory diseases including, but not limited to, inflammation, glomerulonephritis, uveitis, hepatic diseases or disorders, renal diseases or disorders, chronic obstructive pulmonary disease, rheumatoid arthritis, inflammatory bowel disease, vasculitis, dermatitis, osteoarthritis, inflammatory muscle disease, allergic rhinitis, vaginitis, interstitial cystitis, scleroderma, osteoporosis, eczema, allogeneic or xenogeneic transplantation, graft rejection, graft-versus-host disease, corneal transplant rejection, lupus erythematosus, systemic lupus erythematosus, proliferative lupus nephritis, type I diabetes, pulmonary fibrosis, dermatomyositis, thyroiditis, myasthenia gravis, autoimmune hemolytic anemia, cystic fibrosis, chronic relapsing hepatitis, primary biliary cirrhosis, allergic conjunctivitis, hepatitis and atopic dermatitis, asthma and Sjogren's syndrome.

In a further aspect, the disclosed compounds and disclosed pharmaceutical compositions can be used in the treatment of a variety of diseases including Felty's syndrome, Wegener's granulomatosis, Crohn's disease, sarcoidosis, Still's disease, pemphigoid, Takayasu arteritis, systemic sclerosis, relapsing polychondritis, refractory IgA nephropathy, SAPHO2 syndrome (SAS), cytomegalovirus infection including rhinitis or cyst, psoriasis, IGG4 disease, and multiple myeloma.

In a further aspect, the disclosed compounds and disclosed pharmaceutical compositions can be used in combination (administered together or sequentially) with known anti-cancer treatments such as radiation therapy or with cytostatic or cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; BTK inhibitors, SYK inhibitors, ITK inhibitors, PI3-kinase inhibitors, FLT3 inhibitors, EGF inhibitors; PAK inhibitors, VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well. These agents can be used in combination with differentiation agents such as ATRA, EZH2 inhibitors, DNMT inhibitors, corticosteroids, IDH1 inhibitors, IDH2 inhibitors, and Vitamin C. These agents can be used in combination with small molecules that enhance DNA damage killing in cancer cells including PARP inhibitors, MDM2 inhibitors, NAMPT inhibitors, and HSP90 inhibitors. These agents can be used in combination with antibodies that target cell surface molecules on immune or cancer cells including but not limited to CD33, CD37, CD19, CD20, CD3, CD123, CD70, BAFFR, CD4, CD8, CD56, and CD38. These agents can be used in combination with antibodies or peptides which neutralize cytokines including, but not limited to IL1Beta, IL6, IL10, IL21, TNFA, TNFB, and IFN. These agents can be used in combination with cellular CAR-T cells to diminish cellular proliferation in the setting of significant cytokine release syndrome and neurotoxicity. These agents can be used to diminish T-cell proliferation, cytokine production, and neurotoxicity in combination with bi-specific antibodies or peptide molecules that target in a dual manner T-cells and immune/tumor cell antigens such as, but not limited to CD19, CD20 CD33, CD123, CD38, and CD37. These agents can be used to diminish T-cell proliferation and tissue damage caused by immune check point inhibitor antibodies to targets such as, but not limited to PD1, PDL1, CTLA4, and LAG3.

In a further aspect, diseases, disorders or conditions that can be treated or prevented using the disclosed compounds and disclosed pharmaceutical compositions are capable of inhibiting one or more kinases described herein, and accordingly, useful in the treatment of diseases, conditions or disorders involving inflammation and/or that are related to the immune system. These diseases include, but are not limited, to asthma, chronic obstructive pulmonary disease, rheumatoid arthritis, inflammatory bowel disease, glomerulonephritis, neuroinflammatory diseases such as multiple sclerosis, and disorders of the immune system.

In a further aspect, the disclosed compounds and disclosed pharmaceutical compositions can be used for treating immune and immune-related disorders, including, for example, chronic immune diseases/disorders, acute immune diseases/disorders, autoimmune and immunodeficiency diseases/disorders, diseases/disorders involving inflammation, organ transplant graft rejections and graft-versus-host disease and altered (e.g., hyperactive) immune responses. In a still further aspect, other exemplary immune disorders that can be treated using the disclosed compounds and disclosed pharmaceutical compositions include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

The methods disclosed herein are useful for treating angiogenesis-related diseases or disorders. By "angiogenesis-related diseases or disorders" is intended any pathophysiological condition that depends upon the growth of new blood vessels for development or progression or is the result of a lack of blood vessel growth. Thus, inhibition of JNK3 may result in amelioration of diseases which depend upon blood vessel growth, and activation of JNK3 may result in amelioration of diseases resulting from a lack of blood vessel growth.

Excessive angiogenesis occurs in diseases such as cancer, diabetic blindness, age-related macular degeneration, rheumatoid arthritis, psoriasis, and more than 70 other conditions. In these conditions, new blood vessels feed diseased tissues, destroy normal tissues, and in the case of cancer, the new vessels allow tumor cells to escape into the circulation and lodge in other organs (tumor metastases). Excessive angiogenesis occurs when diseased cells produce abnormal amounts of angiogenic growth factors, overwhelming the effects of natural angiogenesis inhibitors.

Angiogenesis is involved in the formation of new vessels and is essential for tumor growth and metastases. Antiangiogenic agents have been used to treat metastatic cancer and to prevent or decrease tumor growth. However, many of these therapies are not tolerated due to the toxic side effects of these agents on immune function (reviewed in Mauriz and Gonzalez-Gallego (2008) *J. Pharm. Sci.* 97(10):4129-54). The present disclosure provides a particularly beneficial mechanism for controlling angiogenesis by selectively targeting JNK3. Selective modulation of JNK3 may reduce the toxic side effects observed in non-selective JNK modulation and other pro- or antiangiogenic agents.

Cardiovascular disease and its associated maladies, dysfunctions and complications are a principal cause of disability and the chief cause of death in the United States. One factor contributing to cardiovascular disease is atherosclerosis. Atherosclerosis is a disease characterized by the deposition of fatty substances, primarily cholesterol, and subsequent fibrosis in the inner layer of an artery, resulting in plaque deposition on the inner surface of the arterial wall and degeneration. If allowed to progress, atherosclerosis can cause narrowing and obstruction of the lumen of the artery resulting in diminished or occluded blood flow. This can lead to ischemia or infarction of the predominantly affected organ or anatomical region, such as the brain, heart, intestine, or extremities. The use of angiogenesis inhibitors, specifically JNK3 inhibitors, to cut off the blood supply to the plaques may prevent atherosclerosis and its complications, including heart attack, stroke, and peripheral vascular disease.

Angiogenesis also plays a pivotal role in the development of diabetic retinopathy and age-related macular degeneration, both of which are major causes of blindness, as well as retinopathy of prematurity in preterm infants (Wong T. Y., et al. *Am. J. Opthalmol.* 2006; 141:446-455). As these disorders progress, the blood vessels of the eye not only proliferate excessively, but the new vessels are weak and leaky and prone to hemorrhage. In both macular degeneration and diabetic retinopathy, new abnormal vessels bleed and cause blindness.

JNK3 inhibitors may also have a role in treating endometriosis, which is characterized by the migration of tissue from the lining of the uterus to the ovaries, urethra and other pelvic structures. The migrant tissue waxes and wanes just as the endometrium does during the menstrual cycle. As it grows, it can interfere with ovarian function and become a source of pain. Angiogenesis inhibitors may be able to "starve" the unwanted tissue by robbing it of its rich blood supply.

Other angiogenesis-related diseases and disorders for which JNK3 inhibitors can be used to treat include rheumatoid arthritis, Crohn's disease, psoriasis, uterine fibroids, benign prostatic hypertrophy, preeclampsia, and certain diseases of premature infants.

The angiogenesis-related diseases treated by the present disclosure are diseases of mammals. The word mammal means any mammal. Some examples of mammals include, for example, pet animals, such as dogs and cats; farm animals, such as pigs, cattle, sheep, and goats; laboratory animals, such as mice and rats; primates, such as monkeys, apes, and chimpanzees; and humans. In some embodiments, humans are preferably treated by the methods of the disclosure.

Kits

In a further aspect, the present disclosure relates to kits comprising at least one disclosed compound, or a pharmaceutically acceptable salt, hydrate, solvate, or polymorph thereof, and one or more of: (a) at least one agent known to inhibit one or more kinases described herein activity, (b) at least one anti-cancer agent, (c) at least one agent known to treat a disorder associated with one or more kinases described herein activity, (d) at least one agent known to treat a neurodegenerative disorder or other inflammation-associated disorder, (e) instructions for treating a disorder associated with activity of one or more kinases described herein, or (f) instructions for administering the compound in connection with another therapy such as an anti-cancer therapy.

The disclosed compounds and/or pharmaceutical compositions comprising the disclosed compounds can conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient. In further aspects, a kit can include optional components that aid in the administration of the unit dose to patients, such as vials for reconstituting powder forms, syringes for injection, customized IV delivery systems, inhalers, etc. Additionally, a kit can contain instructions for preparation and administration of the compositions. The kit can be manufactured as a single use unit dose for one patient, multiple uses for a particular patient (at a constant dose or in which the individual compounds may vary in potency as therapy progresses); or the kit may contain multiple doses suitable for administration to multiple patients ("bulk packaging"). The kit components may be assembled in cartons, blister packs, bottles, tubes, and the like.

In some aspects, the at least one agent known to inhibit JNK3 activity can be an agent that inhibits one or more kinase involved with activation of JNK3, e.g., an inhibitor of MLK3 and/or MLK7.

In a further aspect, the disclosed kits can be packaged in a daily dosing regimen (e.g., packaged on cards, packaged with dosing cards, packaged on blisters or blow-molded plastics, etc.). Such packaging promotes products and increases patient compliance with drug regimens. Such packaging can also reduce patient confusion. The present disclosure also features such kits further containing instructions for use.

In a further aspect, the present disclosure also provides a pharmaceutical pack or kit comprising one or more containers filled with one or more of the ingredients of the pharmaceutical compositions of the disclosure. Associated with such container(s) can be a notice in the form prescribed by a governmental agency regulating the manufacture, use or sale of pharmaceuticals or biological products, which notice reflects approval by the agency of manufacture, use or sale for human administration.

In various aspects, the disclosed kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is contemplated that the disclosed kits can be used in connection with the disclosed methods of making, the disclosed methods of using or treating, and/or the disclosed compositions.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Aspects

Aspect 1. A compound having a structure represented by a formula:

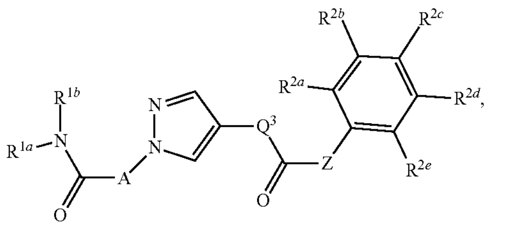

wherein each of $R^{1a}$ and $R^{1b}$ are independently selected from hydrogen, C1-C8 nitrile, C1-C8 alkyl, C1-C8 alkoxy, C1-C8 haloalkyl, C3-C8 cycloalkyl, C3-C8 heterocyclyl, heteroaryl, and aryl;

wherein each of $R^{2a}$, $R^{2b}$, $R^{2c}$, $R^{2d}$, and $R^{2e}$ are independently selected from hydrogen, halo, hydroxy, nitro, azido, —$SF_5$, C1-C3 alkyl, C1-C3 haloalkyl, C1-C3 alkoxy, C1-C3 aminoalkyl, C1-C3 hydroxyalkyl, and —(C1-C3 alkanediyl)-$NR^{5a}R^{5b}$;

wherein each occurrence of $R^{5a}$ and $R^{5b}$ is independently selected from hydrogen, C1-C3 alkyl, C3-C8 cycloalkyl, C3-C8 heterocycloalkyl, aryl and heteroaryl;

wherein A is a structure represented by a formula:

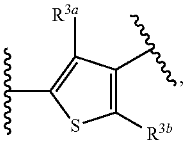

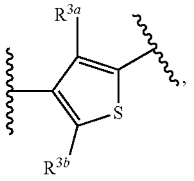

or

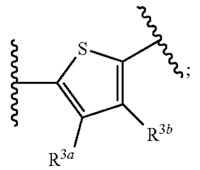

wherein each of $R^{3a}$ and $R^{3b}$ is selected from hydrogen, halo, hydroxy, nitro, amino, azido, —$SF_5$, C1-C3 alkyl, C1-C3 haloalkyl, C1-C3 alkoxy, C1-C3 aminoalkyl, and C1-C3 hydroxyalkyl;

wherein $Q^3$ is $NR^{4c}$, $CR^{4c}$, or O;

wherein $R^{4c}$ is selected from hydrogen, halo, hydroxy, nitro, azido, —$SF_5$, C1-C3 alkyl, C1-C3 haloalkyl, C1-C3 alkoxy, C1-C3 aminoalkyl, C1-C3 hydroxyalkyl, and —(C0-C3 alkanediyl)-$NR^{5a}R^{5b}$;

wherein Z is selected from —O—, —S—, and —$NR^6$—;

wherein $R^6$ is selected from hydrogen and C1-C3 alkyl;

or a pharmaceutically acceptable salt thereof.

Aspect 2. The compound of Aspect 1, having a structure represented by a formula:

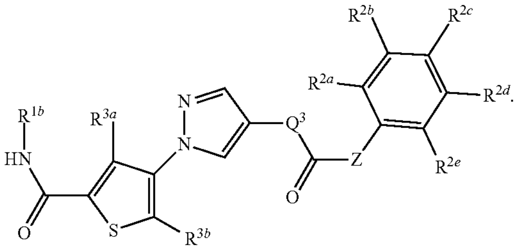

Aspect 3. The compound of Aspect 1 or 2, wherein Z is —O— and —NH—.

Aspect 4. The compound of any one of Aspects 1-3, wherein $Q^3$ is —O— and —NH—.

Aspect 5. The compound of Aspect 1 or 2, wherein Z and $Q^3$ are —NH—.

Aspect 6. The compound of any one of Aspects 1-5, wherein $R^{2b}$, $R^{2c}$, and $R^{2d}$ are hydrogen.

Aspect 7. The compound of Aspect 6, wherein $R^{2a}$ is halo and $R^{2e}$ is hydrogen.

Aspect 8. The compound of Aspect 6, wherein $R^{2a}$ is selected from —Cl and —F.

Aspect 9. The compound of Aspect 6, wherein $R^{2a}$ is —Cl.

Aspect 10. The compound of any one of Aspects 1-5, wherein $R^{2a}$ is —Cl and at least one of $R^{2b}$, $R^{2c}$, $R^{2d}$, and $R^{2e}$ is —F.

Aspect 11. The compound of any one of Aspects 1-5, wherein $R^{2a}$ is —Cl and $R^{2c}$ or $R^{2e}$ is —F.

Aspect 12. The compound of any one of Aspects 1-11, wherein $R^{1b}$ is selected from C1-C8 alkyl, C1-C8 haloalkyl, C1-C8 alkoxy, C3-C8 cycloalkyl, C3-C8 heterocyclyl, and heteroaryl.

Aspect 13. The compound of any one of Aspects 1-11, wherein $R^{1b}$ is methyl, ethyl, or isopropyl.

Aspect 14. The compound of any one of Aspects 1-11, wherein $R^{1b}$ is C3-C6 heterocyclyl.

Aspect 15. The compound of any one of Aspects 1-11, wherein $R^{1b}$ is C3-C5 cycloalkyl.

Aspect 16. The compound of any one of Aspects 1-15, wherein $R^{1a}$ is hydrogen.

Aspect 17. The compound of any one of Aspects 1-16, wherein $R^{3a}$ is hydrogen.

Aspect 18. The compound of any one of Aspects 1-16, wherein $R^{3a}$ and $R^{3b}$ are hydrogen.

Aspect 19. The compound of any one of Aspects 1-16, wherein $R^{3a}$ is hydrogen and $R^{3b}$ is C1-C3 alkyl.

Aspect 20. The compound of Aspect 1, having a structure represented by a formula:

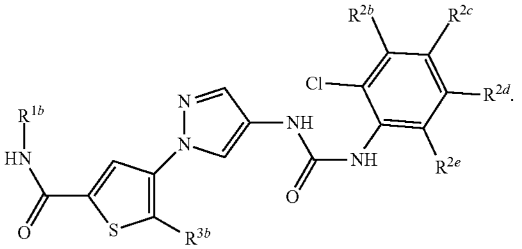

Aspect 21. The compound of Aspect 20, wherein $R^{3b}$ is hydrogen or C3-C6 heterocyclyl.

Aspect 22. The compound of Aspect 20 or 21, wherein at least one of $R^{2b}$, $R^{2c}$, $R^{2d}$, and $R^{2e}$ is —F.

Aspect 23. The compound of Aspect 20 or 21, wherein $R^{2b}$, $R^{2c}$, $R^{2d}$, and $R^{2e}$ are hydrogen.

Aspect 24. The compound of any one of Aspects 20-23, wherein $R^{1b}$ is C3-C6 heterocyclyl.

Aspect 25. The compound of any one of Aspects 20-23, wherein $R^{1b}$ is

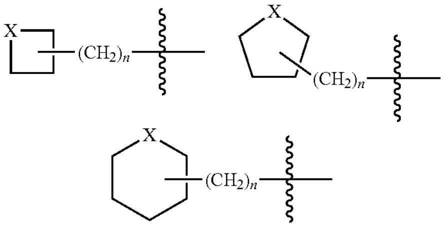

wherein X is O or $NR^7$, wherein $R^7$ is hydrogen or C1-C8 alkyl, and n is an integer from 0 to 5.

Aspect 26. The compound of any one of Aspects 20-23, wherein $R^{1b}$ is

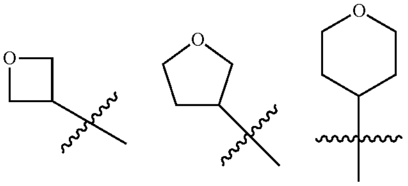 [SMILES: *C1COC1 ; *C1CCOC1 ; *C1CCOCC1]

Aspect 27. The compound of Aspect 1, wherein the compound is

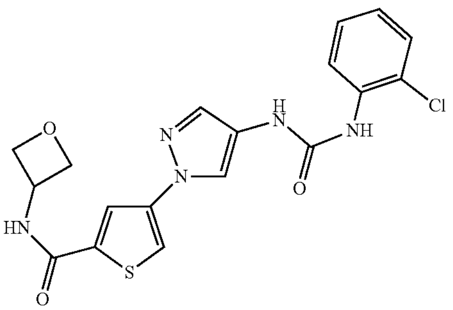 [SMILES: O=C(Nc1cnn(-c2csc(C(=O)NC3COC3)c2)c1)Nc1ccccc1Cl]

Aspect 28. The compound of any one of Aspects 1-27, wherein the compound is a pharmaceutically acceptable salt thereof.

Aspect 29. The compound of Aspect 28, wherein the pharmaceutically acceptable salt is a sodium salt, a potassium salt, or a lithium salt.

Aspect 30. A method for the treatment of a disease or disorder in a mammal comprising the step of administering to the mammal a therapeutically effective amount of at least one compound of any one of Aspects 1-28.

Aspect 31. The method of Aspect 30, wherein the mammal is a human.

Aspect 32. The method of Aspect 31, wherein the mammal has been diagnosed with a need for treatment of the disorder prior to the administering step.

Aspect 33. The method of any one of Aspects 30-32, wherein the disorder or disease can be treated by inhibition of the activity of c-Jun N-terminal kinase 1 (JNK1) c-Jun N-terminal kinase 2 (JNK2), c-Jun N-terminal kinase 3 (JNK3), kinase p38a, ABL1, ABL2, DDR1, DDR2, CK1, MAP4K, GCK, MINK1, HGK, TNIK, or any combination thereof.

Aspect 34. The method of any one of Aspects 30-32, wherein the disorder or disease is associated with increased activity of c-Jun N-terminal kinase 1 (JNK1) c-Jun N-terminal kinase 2 (JNK2), c-Jun N-terminal kinase 3 (JNK3), kinase p38a, or any combination thereof.

Aspect 35. The method of any one of Aspects 30-34, wherein the disorder or disease affects the central nervous system.

Aspect 36. The method of any one of Aspects 30-34, wherein the disorder or disease is selected from Huntington's disease, Parkinson's disease, epilepsy, stroke, amyotrophic lateral sclerosis (ALS), and spinal muscular atrophy (SMA).

Aspect 37. The method of any one of Aspects 30-34, wherein the disorder or disease affects the peripheral nervous system.

Aspect 38. The method of any one of Aspects 30-34, wherein the disorder or disease is selected from deafness and glaucoma.

Aspect 39. The method of any one of Aspects 30-34, wherein the disorder or disease is organ failure.

Aspect 40. The method of any one of Aspects 30-34, wherein the disorder or disease is a cancer.

Aspect 41. The method of any one of Aspects 30-34, wherein the disorder or disease is a nervous system injury, a neurodegenerative condition, or an inflammatory disease.

Aspect 42. The method of Aspect 41, wherein the nervous system injury is spinal cord injury, traumatic brain injury, or stroke.

Aspect 43. The method of Aspect 41, wherein the neurodegenerative condition is Parkinson's disease, Huntington's disease, or Alzheimer's disease.

Aspect 44. The method of Aspect 41, wherein the neurodegenerative condition is Alzheimer's disease.

Aspect 45. The method of Aspect 41, wherein the inflammatory disease is multiple sclerosis or type II diabetes.

Aspect 46. The method of any one of Aspects 30-45, wherein the compound is administered orally to the mammal.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Experimental Section

Commercially available reagents and anhydrous solvents were used without further purification unless otherwise specified. Thin layer chromatography (TLC) analyses were performed with precoated silica gel 60 F254. The mass spectra were recorded by LC/MS with Finnigan LCQ Advantage MAX spectrometer of Thermo Electron®. Flash chromatography was performed on prepacked columns of silica gel (230-400 Mesh, 40-63 μm) by CombiFlash® with EtOAc/hexane or MeOH/DCM as eluents. The preparative HPLC was performed on SunFire $C_{18}$ OBD 10 μm (30×250 mm) with $CH_3CN$+50% MeOH/$H_2O$+0.1% TFA as eluents to purify the targeted compounds. Analytic HPLC was performed on Agilent technologies 1200 series with $CH_3CN$ (Solvent B)/$H_2O$+0.9% $CH_3CN$+0.1% TFA (Solvent A) as eluents and the targeted products were detected by UV in the detection range of 215-310 nm. All compounds were determined to be >95% pure by this method. NMR spectra were recorded with a Bruker® 400 MHz spectrometer at ambient temperature with the residual solvent peaks as internal standards. The line positions of multiplets are in ppm (δ) and the coupling constants (J) are in Hertz. Calibration was performed with an external calibration mixture immediately prior to analysis.

1.1 General Synthetic Procedures:

The synthetic route for preparing inhibitors 3-28 is shown in Scheme 1. A mixture of 4-nitro-1H-pyrazole 31 (44.3 mmol) and Pd/c (500 mg) in anhydrous methanol (50 mL) under a balloon of hydrogen was stirred at room temperature for 3 h. The mixture was filtered through a celite pad and evaporated to give 4-amino-1H-pyrazole 32. To a solution of 4-amino-1H-pyrazole 32 (36.1 mmol) in $CH_2Cl_2$ (20 mL) was added dropwise $Boc_2O$ (36.1 mmol) in $CH_2Cl_2$ (10 mL) and TEA (108.4 mmol) at 0° C., then the mixture was stirred at room temperature for 3 h. The reaction mixture was washed with HCl (1M, 20 mL×2), water (20 mL×2), brine (20 mL), dried over anhydrous $Na_2SO_4$. The resulting solution was concentrated to yield a crude product tert-butyl 1H-pyrazol-4-ylcarbamate 33.

Scheme 1. Synthetic Scheme for compounds 3-28[a]

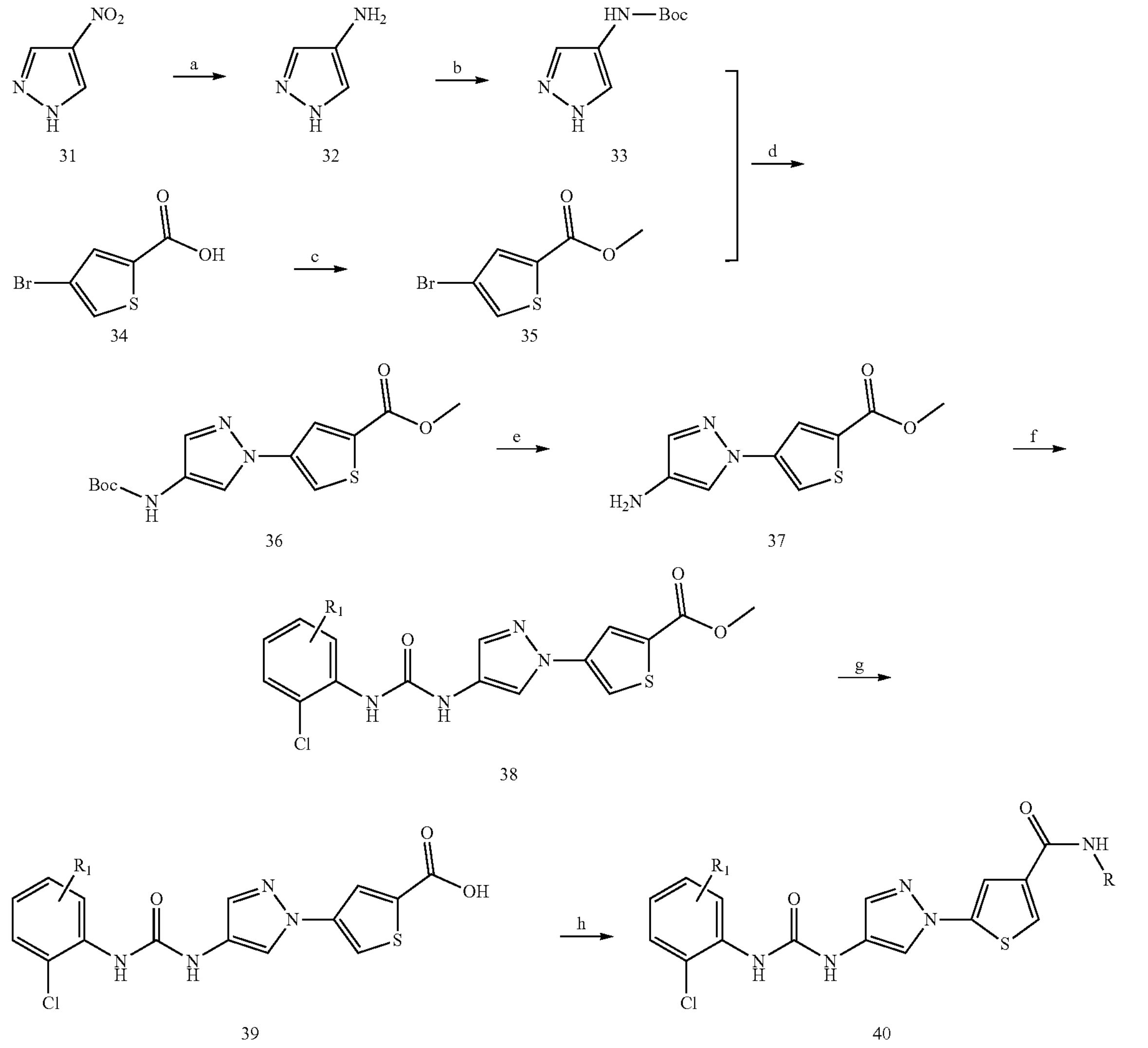

31 32 33 34 35 36 37 38 39 40

[a]Reagent and Conditions: (a) Pd/C, MeOH, $H_2$; (b) $Boc_2O$, TEA, DCM 0→25° C.; (c) $H_2SO_4$, MeOH, reflux; (d) CuI, trans-N,N-dimethylcyclohexane-1,2-diamine, $K_3PO_4$, DMF, 110° C.; (e) HCl/EA; (f) 2-chloroaniline derivative, 4-nitrophenyl carbonochloridate, DIPEA, DCM, 0→25° C.; (g) NaOH, MeOH/$H_2O$; (h) amine, PyBop, DIPEA, DMF, 0→25° C.

To a solution of 4-bromothiophene-2-carboxylic acid 34 (24.15 mmol) in methanol (50 mL) was added concentrated sulfuric acid (2 ml) and stirred at reflux for 3 h. The mixture was poured into water (50 mL) and extracted with EtOAc (50 mL×3), then washed with $NaHCO_3$ (sat., 50 mL×2), water (50 mL×2), brine (50 mL), dried over anhydrous $Na_2SO_4$. The resulting solution was concentrated in vacuo to yield crude product methyl 4-bromothiophene-2-carboxylate 35.

A mixture of tert-butyl 1H-pyrazol-4-ylcarbamate 33 (16.4 mmol), methyl 4-bromothiophene-2-carboxylate 35 (8.2 mmol), CuI (1.64 mmol), $K_3PO_4$ (24.6 mmol), trans-N,N-dimethylcyclohexane-1,2-diamine (3.28 mmol) in DMF (30 ml) was purged with nitrogen and stirred at 110° C. for overnight. The reaction mixture was cooled to room temperature, then poured into water (150 mL). The pH of mixture was adjusted to 3-4 via the addition of citric acid (sat.), then the mixture was extracted with EtOAc (100 mL×3). The organic phases were washed with water (100 mL×2), brine (100 mL), dried over anhydrous $Na_2SO_4$. The resulting solution was concentrated in vacuo and the residue was purified by flash column chromatography on silica gel to give methyl 4-(4-(tert-butoxycarbonylamino)-1H-pyrazol-1-yl)thiophene-2-carboxylate 36.

To a solution of methyl 4-(4-(tert-butoxycarbonylamino)-1H-pyrazol-1-yl)thiophene-2-carboxylate 36 (7.187 mmol), HCl/EA (3 mol/L, 30 mL) was added and the solution was stirred at room temperature overnight. The reaction mixture was filtered to give crude product methyl 4-(4-amino-1H-pyrazol-1-yl)thiophene-2-carboxylate 37.

To a solution of 4-nitrophenyl carbonochloridite (2.77 mmol) in dried $CH_2Cl_2$ (5 mL) was added a 2-chloroaniline derivative (3.01 mmol) in dried $CH_2Cl_2$ (2 mL) at room temperature and DIPEA (6.93 mmol) at 0° C., then stirred at room temperature for 1-2 h. Methyl 4-(4-amino-1H-pyrazol-1-yl)thiophene-2-carboxylate 37 (2.31 mmol) was added and DIPEA (4.62 mmol) at 0° C., then stirred at room temperature for another 1-2 h. The reaction mixture was diluted with EtOAc (20 mL), washed with $NaHCO_3$ (sat., 20 mL×3), water (20 mL×2), brine (20 mL), dried over anhydrous $Na_2SO_4$. The resulting solution was concentrated in vacuo, and the residue was purified by chromatography on silica gel (dichloromethane/methanol) to give methyl 4-(4-(3-(2-chlorophenyl)ureido)-1H-pyrazol-1-yl)thiophene-2-carboxylate derivative 38.

To a solution of methyl 4-(4-(3-(2-chlorophenyl)ureido)-1H-pyrazol-1-yl)thiophene-2-carboxylate 38 (0.90 mmol) in methanol (10 mL), NaOH in $H_2O$ (30%, 10 mL) was added dropwise and stirred at room temperature for overnight. The reaction mixture was washed with petroleum ether (20 mL×2), adjusted pH with citric acid (sat.) to 4-5, then extracted with EtOAc (20 mL×3). The organic phases were washed with water (20 mL×2), water (20 mL×2), brine (20 mL), dried over anhydrous $Na_2SO_4$. The resulting solution was concentrated in vacuo to give crude product 4-(4-(3-(2-chlorophenyl)ureido)-1H-pyrazol-1-yl)thiophene-2-carboxylic acid 39.

To a solution of 4-(4-(3-(2-chlorophenyl)ureido)-1H-pyrazol-1-yl)thiophene-2-carboxylic acid 39 (0.55 mmol) in anhydrous dimethyl formamide (3 mL) was added PyBop (0.83 mmol), DIPEA (1.66 mmol), and an amine (0.83 mmol) at 0° C., then stirred at room temperature for overnight. The reaction mixture was poured into water (20 mL), then extracted with EtOAc (10 mL×3). The organic phases were washed with water (10 mL×2), brine (10 mL), dried over anhydrous $Na_2SO_4$. The resulting solution was concentrated in vacuo and the residue was purified by preparative HPLC to give final products 6-28.

1.2 Characterization of Inhibitors 3-28.

N-(azetidin-3-yl)-2-(4-(3-(2-chlorophenyl)ureido)-1H-pyrazol-1-yl)thiazole-4-carboxamide (3)

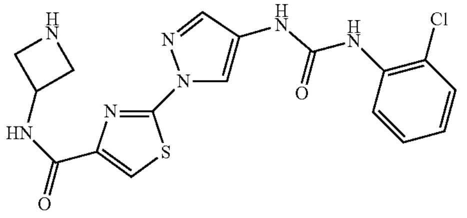 [SMILES: O=C(Nc1cnn(-c2nc(C(=O)NC3CNC3)cs2)c1)Nc1ccccc1Cl]

A similar scheme as described in Scheme 1 was used to prepare 3 by replacing the thiophene derivative 34 with a thiazole analog. $^1$H-NMR (400 MHz, DMSO): δ 9.66 (s, 1H), 9.13 (d, J=18 Hz, 1H), 8.76 (s, 1H), 8.64 (b, 1H), 8.49 (s, 1H), 8.14 (d, J=11 Hz, 1H), 8.09 (s, 1H), 7.90 (s, 1H), 7.48 (d, J=20 Hz, 1H), 7.33 (t, J=20 Hz, 1H), 7.07 (t, J=19 Hz, 1H), 4.85 (dd, J=20 Hz, 39 Hz, 1H), 4.19 (m, 4H). LC-MS, single peak monitoring at 254 nm. Formula: C17H16ClN7O2S, MS (ESI) m/z: [M+H] calcd: 418. found 418.

N-(azetidin-3-yl)-5-(4-(3-(2-chlorophenyl)ureido)-1H-pyrazol-1-yl)thiophene-2-carboxamide (4)

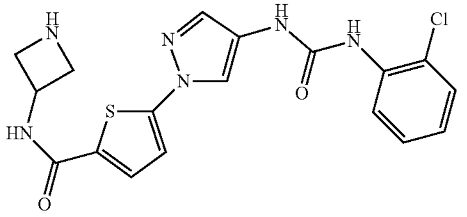 [SMILES: O=C(Nc1cnn(-c2ccc(C(=O)NC3CNC3)s2)c1)Nc1ccccc1Cl]

A similar scheme as described in Scheme 1 was used to prepare 4 by replacing the thiophene derivative 34 with the corresponding thiophene analog. $^1$H-NMR (400 MHz, DMSO): b 9.46 (s, 1H), 9.09-9.07 (m, 1H), 8.71-8.65 (m, 1H), 8.47 (s, 1H), 8.38 (s, 1H), 8.17-8.15 (m, 1H), 7.80 (s, 1H), 7.68-7.66 (m, 1H), 7.47-7.45 (m, 1H), 7.38-7.37 (m, 1H), 7.32-7.28 (m, 1H), 7.06-7.02 (m, 1H), 4.76-4.71 (m, 1H), 4.18-4.08 (m, 4H). LC-MS, single peak monitoring at 254 nm. Chemical Formula: C18H17ClN6O2S, MS (ESI) m/z: [M+H] calcd: 417. found 417.

N-(azetidin-3-yl)-5-(4-(3-(2-chlorophenyl)ureido)-1H-pyrazol-1-yl)thiophene-3-carboxamide (5)

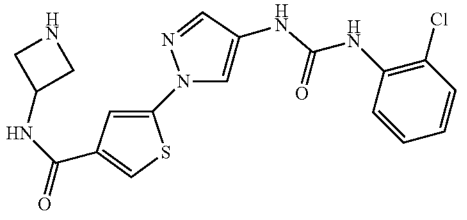 [SMILES: O=C(Nc1cnn(-c2cc(C(=O)NC3CNC3)cs2)c1)Nc1ccccc1Cl]

A similar scheme as described in Scheme 1 was used to prepare 5 by replacing the thiophene derivative 34 with a 2-Br thiophene analog. $^1$H NMR (400 MHz, DMSO): LC-MS, single peak monitoring at 254 nm. Chemical Formula: C18H17ClN6O2S, MS (ESI) m/z: [M+H] calcd: 417. found 417.

N-(azetidin-3-yl)-4-(4-(3-(2-chlorophenyl)ureido)-1H-pyrazol-1-yl)thiophene-2-carboxamide (6)

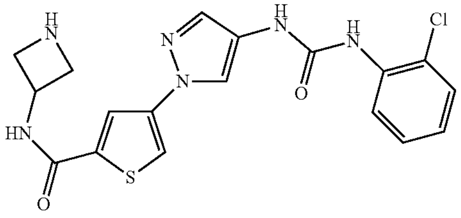 [SMILES: O=C(Nc1cnn(-c2csc(C(=O)NC3CNC3)c2)c1)Nc1ccccc1Cl]

Scheme 1 was used to prepare 6. $^1$H-NMR (400 MHz, DMSO): δ 9.463 (s, 1H), 9.303-9.287 (d, J=6.4 Hz, 1H), 8.719 (s, 2H), 8.414-8.383 (d, J=12.4 Hz, 2H), 8.265 (s, 1H), 8.187-8.166 (d, J=8.4 Hz, 1H), 7.986 (s, 1H), 7.741 (s, 1H), 7.471-7.451 (d, J=8.0 Hz, 1H), 7.318-7.287 (t, J=16.0 Hz, 1H), 7.053-7.014 (t, J=15.6 Hz, 1H), 4.810-4.753 (q, J=7.6 Hz, 1H), 4.204-4.157 (t, J=18.8 Hz, 2H), 4.116-4.069 (t, J=18.8 Hz, 2H). LC-MS, single peak monitoring at 254 nm. Chemical Formula: C18H17ClN6O2S, MS (ESI) m/z: [M+H] calcd: 417. found 417.

4-(4-(3-(2-chlorophenyl)ureido)-1H-pyrazol-1-yl)-N-methylthiophene-2-carboxamide (7)

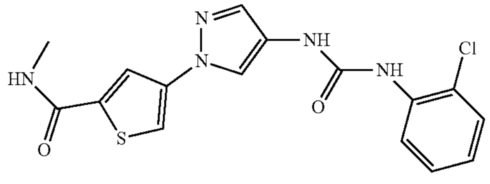 [SMILES: CNC(=O)c1cc(-n2cc(NC(=O)Nc3ccccc3Cl)cn2)cs1]

Scheme 1 was used to prepare 7. $^1$H-NMR (400 MHz, DMSO): δ 9.40 (s, 1H), 8.65 (m, 1H), 8.36 (d, J=20 Hz, 2H), 8.19 (d, J=20 Hz, 2H), 7.87 (s, 1H), 7.72 (s, 1H), 7.46 (dd, J=20 Hz, J=3 Hz, 1H), 7.31 (t, J=18 Hz, 1H), 7.03 (t, J=18 Hz, 1H), 2.78 (s, 3H). LC-MS, single peak monitoring at 254 nm. Chemical Formula: C16H14ClN5O2S, MS (ESI) m/z: [M+H] calcd: 376. found 376.

4-(4-(3-(2-chlorophenyl)ureido)-1H-pyrazol-1-yl)-N-cyclopropylthiophene-2-carboxamide (8)

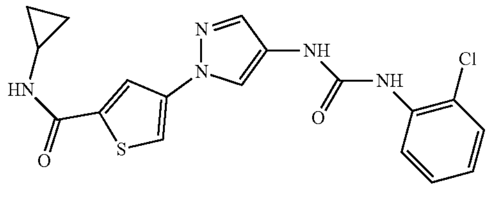 [SMILES: O=C(Nc1cnn(-c2csc(C(=O)NC3CC3)c2)c1)Nc1ccccc1Cl]

Scheme 1 was used to prepare 8. $^1$H-NMR (400 MHz, DMSO): δ 9.395 (s, 1H), 8.640-8.632 (d, J=3.2 Hz, 1H), 8.365-8.350 (d, J=6 Hz, 2H), 8.197-8.174 (d, J=9.2 Hz, 2H), 7.870 (s, 1H), 7.709 (s, 1H), 7.466-7.446 (d, J=8 Hz, 1H), 7.315-7.276 (t, J=8 Hz, 1H), 7.046-7.008 (t, J=7.6 Hz, 1H), 2.827-2.818 (d, J=3.6 Hz, 1H), 0.719-0.702 (d, J=6.8 Hz, 2H), 0.582 (s, 2H). LC-MS, single peak monitoring at 254 nm. Chemical Formula: C18H16ClN5O2S, MS (ESI) m/z: [M+H] calcd: 402. found 402.

(R)-4-(4-(3-(2-chlorophenyl)ureido)-1H-pyrazol-1-yl)-N-(pyrrolidin-3-yl)thiophene-2-carboxamide (9)

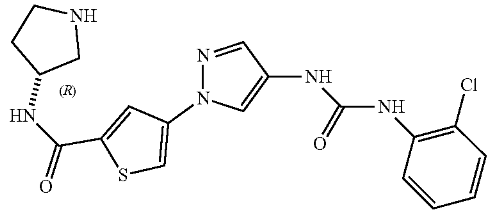

Scheme 1 was used to prepare 9. $^1$H-NMR (400 MHz, DMSO): δ 9.443 (s, 1H), 8.846 (s, 2H), 8.791-8.776 (d, J=6 Hz, 1H), 8.403-8.387 (d, J=6 Hz, 2H), 8.275 (s, 1H), 8.181-8.160 (d, J=8 Hz, 1H), 7.952 (s, 1H), 7.730 (s, 1H), 7.468-7.449 (d, J=8 Hz, 1H), 7.317-7.279 (t, J=15 Hz, 1H), 7.051-7.014 (t, J=15 Hz, 1H), 4.490-4.450 (m, 1H), 3.467-3.420 (m, 1H), 3.202-3.161 (m, 1H), 2.260-2.171 (m, 1H), 2.071-1.986 (m, 1H). LC-MS, single peak monitoring at 254 nm. Chemical Formula: C19H19ClN6O2S, MS (ESI) m/z: [M+H] calcd: 431. found 431.

(R)-4-(4-(3-(2-chlorophenyl)ureido)-1H-pyrazol-1-yl)-N-(1-methylpyrrolidin-3-yl)thiophene-2-carboxamide (10)

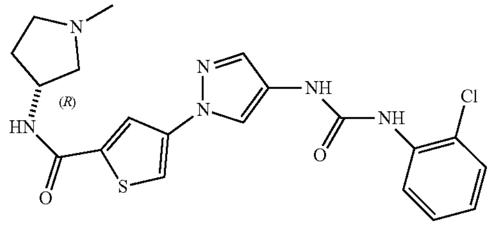

Scheme 1 was used to prepare 10. $^1$H-NMR (400 MHz, DMSO): δ 9.866 (s, 1H), 9.433 (s, 1H), 8.915-8.830 (d, J=34 Hz, 1H), 8.406-8.379 (d, J=11 Hz, 2H), 8.280 (s, 1H), 8.181-8.161 (d, J=8 Hz, 1H), 7.957 (s, 1H), 7.732 (s, 1H), 7.468-7.449 (d, J=8 Hz, 1H), 7.316-7.279 (t, J=15 Hz, 1H), 7.051-7.013 (t, J=15 Hz, 1H), 4.530 (s, 1H), 3.916-3.608 (m, 2H), 3.252-3.026 (m, 2H), 2.876 (s, 3H), 2.328-2.008 (m, 2H). LC-MS, single peak monitoring at 254 nm. Chemical Formula: C20H21ClN6O2S, MS (ESI) m/z: [M+H] calcd: 445. found 445.

(R)-4-(4-(3-(2-chlorophenyl)ureido)-1H-pyrazol-1-yl)-N-(1-(methyl-d3)pyrrolidin-3-yl)thiophene-2-carboxamide (11)

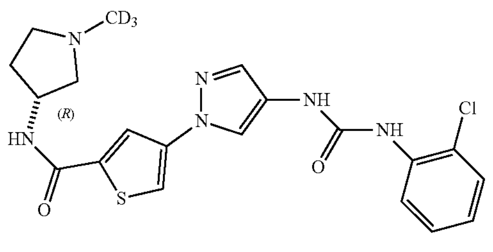

Scheme 1 was used to prepare 11. $^1$H-NMR (400 MHz, DMSO): δ 9.879 (s, 1H), 9.442 (s, 1H), 8.857 (s, 1H), 8.403-8.385 (d, J=7 Hz, 2H), 8.277 (s, 1H), 8.179-8.158 (d, J=8 Hz, 1H), 7.954 (s, 1H), 7.731 (s, 1H), 7.467-7.447 (d, J=8 Hz, 1H), 7.315-7.276 (d, J=16 Hz, 1H), 7.051-7.012 (d, J=16 Hz, 1H), 4.530 (s, 1H), 3.919-3.598 (m, 2H), 3.275-3.123 (m, 2H), 2.327-2.121 (m, 2H). LC-MS, single peak monitoring at 254 nm. Chemical Formula: C20H18D3ClN6O2S, MS (ESI) m/z: [M+H] calcd: 448. found 448.

(S)-4-(4-(3-(2-chlorophenyl)ureido)-1H-pyrazol-1-yl)-N-(1-methylpyrrolidin-3-yl)thiophene-2-carboxamide (12)

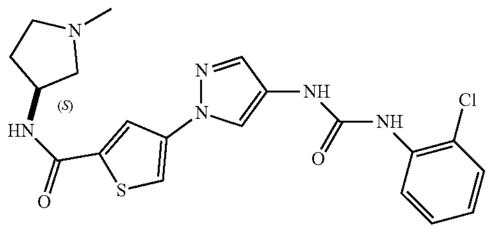

Scheme 1 was used to prepare 12. $^1$H-NMR (400 MHz, DMSO): δ 9.938 (s, 1H), 9.449 (s, 1H), 8.850 (s, 1H), 8.402-8.385 (d, J=7 Hz, 2H), 8.285 (s, 1H), 8.181-8.160 (d, J=8 Hz, 2H), 7.955 (s, 1H), 7.468-7.448 (d, J=8 Hz, 1H), 7.316-7.277 (t, J=16 Hz, 1H), 7.051-7.012 (t, J=16 Hz, 1H), 4.538 (s, 1H), 3.733-3.599 (m, 2H), 3.111-3.098 (m, 2H), 2.844 (s, 3H), 2.327-2.052 (m, 2H). LC-MS, single peak monitoring at 254 nm. Chemical Formula: C20H21ClN6O2S, MS (ESI) m/z: [M+H] calcd: 445. found 445.

(S)-4-(4-(3-(2-chlorophenyl)ureido)-1H-pyrazol-1-yl)-N-(1-isopropylpyrrolidin-3-yl)thiophene-2-carboxamide (13)

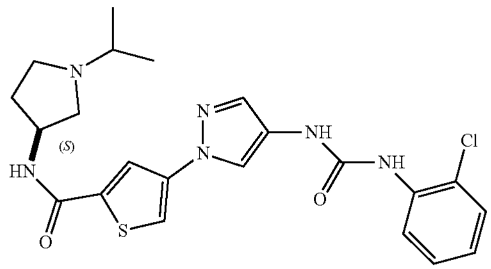

Scheme 1 was used to prepare 13. $^1$H-NMR (400 MHz, DMSO): δ 9.764 (s, 1H), 9.447-9.427 (d, J=8 Hz, 1H), 8.904-8.793 (m, 1H), 8.403-8.385 (d, J=7 Hz, 2H), 8.304-8.265 (d, J=16 Hz, 1H), 8.179-8.159 (d, J=8 Hz, 1H), 7.960 (s, 1H), 7.732 (s, 1H), 7.468-7.448 (d, J=8 Hz, 1H), 7.315-7.277 (t, J=15 Hz, 1H), 7.051-7.013 (m, 1H), 4.515-4.485 (t, J=12 Hz, 1H), 3.844-3.830 (m, 1H), 3.665-3.576 (m, 1H), 3.493-3.457 (t, J=14 Hz, 2H), 3.231-3.070 (m, 1H), 2.406-2.209 (m, 2H), 1.284-1.269 (d, J=6 Hz, 6H). LC-MS, single peak monitoring at 254 nm. Chemical Formula: C22H25ClN6O2S, MS (ESI) m/z: [M+H] calcd: 505. found 505.

4-(4-(3-(2-chlorophenyl)ureido)-1H-pyrazol-1-yl)-N-(1-methylpiperidin-4-yl)thiophene-2-carboxamide (14)

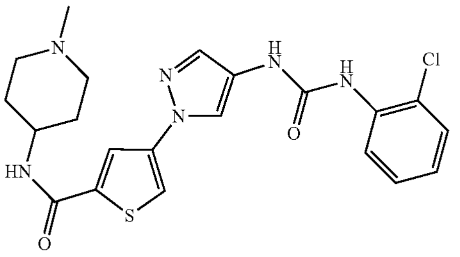 [SMILES: CN1CCC(NC(=O)c2cc(-n3cc(NC(=O)Nc4ccccc4Cl)cn3)cs2)CC1]

Scheme 1 was used to prepare 14. $^1$H-NMR (400 MHz, DMSO): δ 9.432 (s, 2H), 8.685-8.666 (d, J=8 Hz, 1H), 8.385 (s, 1H), 8.290 (s, 1H), 8.183-8.163 (d, J=8 Hz, 1H), 7.911 (s, 1H), 7.719 (s, 1H), 7.469-7.449 (d, J=8 Hz, 1H), 7.315-7.276 (t, J=16 Hz, 1H), 7.051-7.012 (t, J=16 Hz, 1H), 3.991-3.975 (d, J=6 Hz, 1H), 3.489-3.460 (d, J=12 Hz, 2H), 3.112-3.086 (d, J=10 Hz, 2H), 2.777 (s, 3H), 2.067-2.033 (d, J=16 Hz, 2H), 1.792-1.703 (m, 2H). LC-MS, single peak monitoring at 254 nm. Chemical Formula: C21H23ClN6O2S, MS (ESI) m/z: [M+H] calcd: 459. found 459.

4-(4-(3-(2-chlorophenyl)ureido)-1H-pyrazol-1-yl)-N-(tetrahydro-2H-pyran-4-yl)thiophene-2-carboxamide (15)

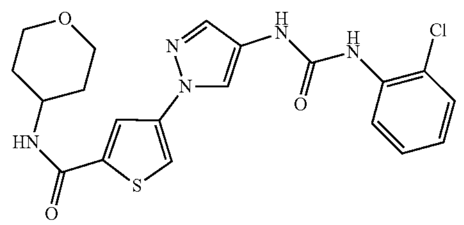 [SMILES: O=C(Nc1cnn(-c2csc(C(=O)NC3CCOCC3)c2)c1)Nc1ccccc1Cl]

Scheme 1 was used to prepare 15. $^{1}$H-NMR (400 MHz, DMSO): δ 9.398 (s, 1H), 8.531-8.513 (d, J=7 Hz, 2H), 8.390-8.356 (d, J=14 Hz, 1H), 8.296 (s, 1H), 8.199-8.178 (d, J=8 Hz, 1H), 7.877 (s, 1H), 7.716 (s, 1H), 7.467-7.447 (d, J=8 Hz, 1H), 7.317-7.279 (t, J=8 Hz, 1H), 7.047-7.009 (t, J=15 Hz, 1H), 3.951 (s, 1H), 3.896-3.872 (d, J=10 Hz, 2H), 3.413-3.384 (t, J=12 Hz, 2H), 1.792-1.766 (d, J=10 Hz, 2H), 1.606-1.526 (m, 2H). LC-MS, single peak monitoring at 254 nm. Chemical Formula: C20H20ClN5O3S, MS (ESI) m/z: [M+H] calcd: 446; found 446.

(R)-4-(4-(3-(2-chlorophenyl)ureido)-1H-pyrazol-1-yl)-N-(tetrahydrofuran-3-yl)thiophene-2-carboxamide (16)

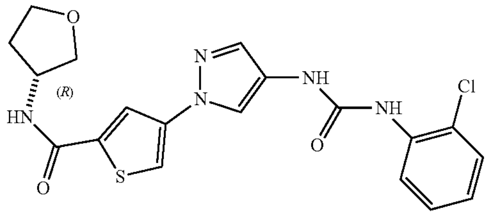

Scheme 1 was used to prepare 16. $^{1}$H-NMR (400 MHz, DMSO): δ 9.392 (s, 1H), 8.749-8.733 (d, J=6.4 Hz, 1H), 8.377 (s, 1H), 8.347-8.332 (d, J=6.0 Hz, 2H), 8.196-8.175 (d, J=8.4 Hz, 2H), 7.879 (s, 1H), 7.714 (s, 1H), 7.464-7.444 (d, J=8.0 Hz, 1H), 7.315-7.276 (t, J=15.6 Hz, 1H), 7.046-7.077 (t, J=15.6 Hz, 1H), 4.441 (s, 1H), 3.897-3.824 (m, 2H), 3.753-3.698 (dd, J=13.6, 8.0 Hz, 1H), 3.623-3.590 (dd, J=9.6, 4.0 Hz, 1H), 2.211-2.123 (m, 1H), 1.954-1.894 (m, 1H). LC-MS, single peak monitoring at 254 nm. Chemical Formula: C19H18ClN5O3S, MS (ESI) m/z: [M+H] calcd: 432. found 432.

4-(4-(3-(2-chlorophenyl)ureido)-1H-pyrazol-1-yl)-N-(oxetan-3-yl)thiophene-2-carboxamide (17)

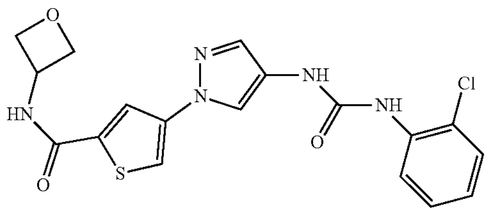 [SMILES: O=C(Nc1cnn(-c2csc(C(=O)NC3COC3)c2)c1)Nc1ccccc1Cl]

Scheme 1 was used to prepare 17. $^{1}$H-NMR (400 MHz, DMSO): δ 9.407 (s, 1H), 9.323-9.307 (d, J=6.4 Hz, 1H), 8.399 (s, 1H), 8.358-8.339 (d, J=7.6 Hz, 2H), 8.200-8.180 (d, J=8.0 Hz, 1H), 7.919 (s, 1H), 7.731 (s, 1H), 7.468-7.448 (d, J=8.0 Hz, 1H), 7.319-7.280 (t, J=15.6 Hz, 1H), 7.048-7.010 (t, J=15.2 Hz, 1H), 5.012-4.961 (q, J=6.8 Hz, 1H), 4.797-4.763 (t, J=13.6 Hz, 2H), 4.609-4.579 (t, J=12.0 Hz, 2H). LC-MS, single peak monitoring at 254 nm. Chemical Formula: C18H16ClN5O3S, MS (ESI) m/z: [M+H] calcd: 418. found 418.

4-(4-(3-(2-chlorophenyl)ureido)-1H-pyrazol-1-yl)-N-(3-methyloxetan-3-yl)thiophene-2-carboxamide (18)

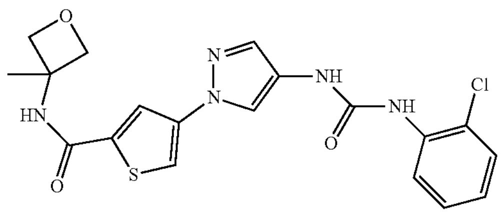 [SMILES: CC1(NC(=O)c2cc(-n3cc(NC(=O)Nc4ccccc4Cl)cn3)cs2)COC1]

Scheme 1 was used to prepare 18. $^{1}$H-NMR (400 MHz, DMSO): δ 9.44 (s, 1H), 9.10 (s, 1H), 8.39 (s, 1H), 8.38 (s, 1H), 8.26 (d, J=4.0 Hz, 1H), 8.19 (dd, J=4 Hz, 21 Hz, 1H), 7.91 (d, J=3 Hz, 1H), 7.73 (s, 1H), 7.46 (dd, J=4.0 Hz, 20 Hz, 1H), 7.30 (t, J=19 Hz, 1H), 7.03 (t, J=19 Hz, 1H), 4.72 (d, J=15 Hz, 2H), 4.38 (t, J=16 Hz, 2H), 1.61 (s, 3H). LC-MS, single peak monitoring at 254 nm. Chemical Formula: C19H18ClN5O3S, MS (ESI) m/z: [M+H] calcd: 432; found 432.

4-(4-(3-(2-chlorophenyl)ureido)-1H-pyrazol-1-yl)-N-((1-methylpiperidin-4-yl)methyl)thiophene-2-carboxamide (19)

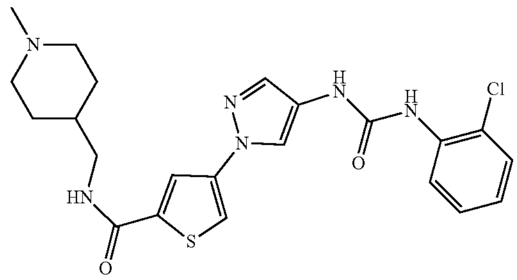 [SMILES: CN1CCC(CNC(=O)c2cc(-n3cc(NC(=O)Nc4ccccc4Cl)cn3)cs2)CC1]

Scheme 1 was used to prepare 19. $^{1}$H-NMR (400 MHz, DMSO): δ 9.449 (s, 1H), 9.218 (s, 1H), 8.775-8.748 (t, 1H), 8.383 (s, 1H), 8.252 (s, 1H), 8.180-8.159 (d, J=8.4 Hz, 1H), 7.897 (s, 1H), 7.716 (s, 1H), 7.467-7.447 (d, J=8.0 Hz, 1H), 7.314-7.274 (t, J=16.0 Hz, 1H), 7.050-7.011 (t, J=15.6 Hz, 1H), 3.192-3.163 (t, J=11.6 Hz, 2H), 2.912-2.889 (d, J=9.2 Hz, 2H), 2.800-2.669 (m, J=52.4 Hz, 3H), 2.005-1.774 (m, J=92.4 Hz, 4H), 1.414-1.351 (t, J=25.6 Hz, 2H), 0.863-0.800 (m, J=25.2 Hz, 1H). LC-MS, single peak monitoring at 254 nm. Chemical Formula: C22H25ClN6O2S, MS (ESI) m/z: [M+H] calcd: 473. found 473.

4-(4-(3-(2-chlorophenyl)ureido)-1H-pyrazol-1-yl)-N-(piperidin-4-ylmethyl)thiophene-2-carboxamide (20)

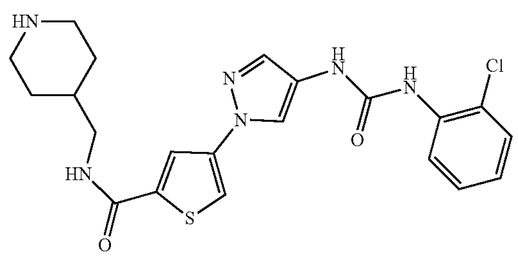 [SMILES: O=C(Nc1cnn(-c2csc(C(=O)NCC3CCNCC3)c2)c1)Nc1ccccc1Cl]

Scheme 1 was used to prepare 20. $^1$H-NMR (400 MHz, DMSO): δ 9.438 (s, 1H), 8.771-8.758 (d, J=5.2 Hz, 1H), 8.486 (s, 1H), 8.385-8.377 (d, J=3.2 Hz, 2H), 8.256 (s, 1H), 8.185-8.165 (d, J=8.0 Hz, 2H), 7.898 (s, 1H), 7.716 (s, 1H), 7.470-7.450 (d, J=8.0 Hz, 1H), 7.319-7.276 (t, J=17.2 Hz, 1H), 7.051-7.013 (t, J=15.2 Hz, 1H), 3.357-3.296 (d, J=24.4 Hz, 2H), 3.184 (s, 1H), 2.870-2.841 (d, J=11.6 Hz, 2H), 1.837-1.806 (m, J=12.4 Hz, 3H), 1.349-1.319 (d, J=12.0 Hz, 2H). LC-MS, single peak monitoring at 254 nm. Chemical Formula: C21H23ClN6O2S, MS (ESI) m/z: [M+H] calcd: 459. found 459.

(R)-4-(4-(3-(2-chlorophenyl)ureido)-1H-pyrazol-1-yl)-N-((1-methylpyrrolidin-3-yl)methyl)thiophene-2-carboxamide (21)

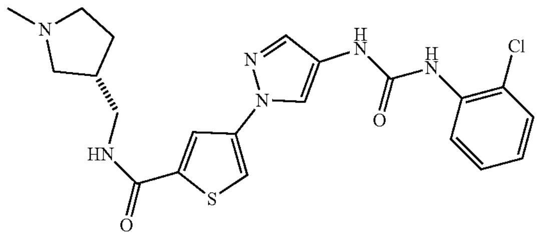

Scheme 1 was used to prepare 21. $^1$H-NMR (400 MHz, DMSO): δ 9.755 (s, 1H), 9.429 (s, 1H), 8.822 (s, 1H), 8.387-8.373 (d, J=5.6 Hz, 2H), 8.245-8.242 (d, J=1.2 Hz, 1H), 8.185-8.161 (dd, J=8.4, 1.2 Hz, 1H), 7.917-7.914 (d, J=1.2 Hz, 1H), 7.721 (s, 1H), 7.471-7.448 (dd, J=8.0, 1.2 Hz, 2H), 7.317-7.252 (m, 1H), 7.054-7.012 (m, 1H), 3.667-3.565 (d, J=40.8 Hz, 2H), 3.188-3.022 (m, 2H), 2.839 (s, 3H), 2.757 (s, 1H), 2.208-1.665 (m, 2H). LC-MS, single peak monitoring at 254 nm. Chemical Formula: C21H23ClN6O2S, MS (ESI) m/z: [M+H] calcd: 459. found 459.

(R)-4-(4-(3-(2-chlorophenyl)ureido)-1H-pyrazol-1-yl)-N-((tetrahydrofuran-3-yl)methyl)thiophene-2-carboxamide (22)

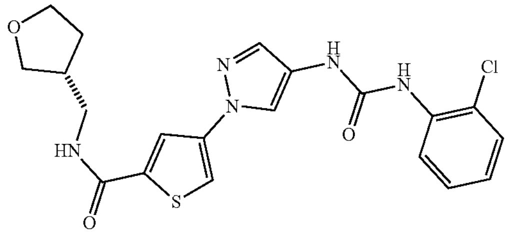

Scheme 1 was used to prepare 22. $^1$H-NMR (400 MHz, DMSO): δ 9.393 (s, 1H), 8.769-8.742 (t, J=10.8 Hz, 1H), 8.383-8.351 (d, J=12.8 Hz, 2H), 8.249 (s, 1H), 8.197-8.176 (d, J=8.4 Hz, 1H), 7.884 (s, 1H), 7.718 (s, 1H), 7.466-7.447 (d, J=7.6 Hz, 1H), 7.316-7.276 (t, J=16.0 Hz, 1H), 7.047-7.007 (t, J=16.0 Hz, 1H), 3.753-3.677 (m, 2H), 3.650-3.594 (m, 1H), 3.489-3.456 (m, 1H), 2.023-1.912 (m, 2H), 1.641-1.560 (m, 1H). LC-MS, single peak monitoring at 254 nm. Chemical Formula: C20H20ClN5O3S, MS (ESI) m/z: [M+H] calcd: 446. found 446.

(S)-4-(4-(3-(2-chlorophenyl)ureido)-1H-pyrazol-1-yl)-N-((1-methylpyrrolidin-2-yl)methyl)thiophene-2-carboxamide (23)

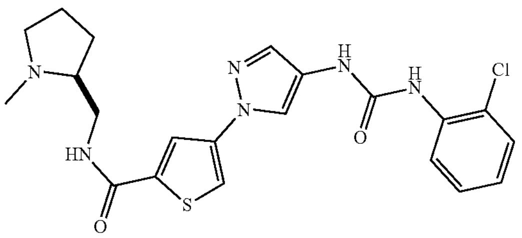

Scheme 1 was used to prepare 23. LC-MS, single peak monitoring at 254 nm. Chemical Formula: C21H23ClN6O2S, MS (ESI) m/z: [M+H] calcd: 459. found 459.

4-(4-(3-(2-chlorophenyl)ureido)-1H-pyrazol-1-yl)-N-((tetrahydro-2H-pyran-4-yl)methyl)thiophene-2-carboxamide (24)

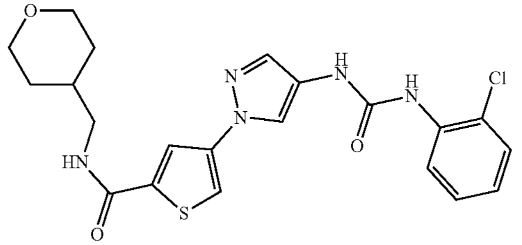 [SMILES: O=C(Nc1cnn(-c2csc(C(=O)NCC3CCOCC3)c2)c1)Nc1ccccc1Cl]

Scheme 1 was used to prepare 24. $^1$H-NMR (400 MHz, DMSO): δ 9.393 (s, 1H), 8.676-8.648 (t, J=11.2 Hz, 1H), 8.375-8.349 (d, J=10.4 Hz, 2H), 8.259-8.255 (d, J=1.6 Hz, 1H), 8.197-8.173 (dd, J=1.2, 8.4 Hz, 1H), 7.868-7.865 (d, J=1.2 Hz, 1H), 7.711 (s, 1H), 7.467-7.444 (dd, J=1.2, 8.0 Hz, 1H), 7.314-7.275 (m, J=15.6 Hz, 1H), 7.086-7.007 (m, 1H), 3.865-3.830 (dd, J=2.4, 11.2 Hz, 2H), 3.296-3.241 (t, J=22.0 Hz, 2H), 3.162-3.131 (t, J=12.4 Hz, 2H), 2.024-1.951 (m, 2H), 1.620-1.588 (d, J=12.8 Hz, 2H), 1.468-1.434 (m, 1H). LC-MS, single peak monitoring at 254 nm. Chemical Formula: C21H22ClN5O3S, MS (ESI) m/z: [M+H] calcd: 460. found 460.

4-(4-(3-(2-chloro-6-fluorophenyl)ureido)-1H-pyrazol-1-yl)-N-(oxetan-3-yl)thiophene-2-carboxamide (25)

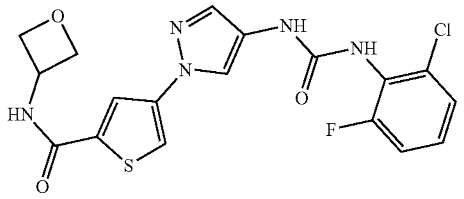 [SMILES: O=C(Nc1cnn(-c2csc(C(=O)NC3COC3)c2)c1)Nc1c(F)cccc1Cl]

Scheme 1 was used to prepare 25. $^1$H-NMR (400 MHz, DMSO): δ 9.27 (d, J=6.4 Hz, 1H), 8.91 (s, 1H), 8.31 (s, 2H), 8.26 (s, 1H), 7.86 (s, 1H), 7.68 (s, 1H), 7.33 (m, 3H), 4.97 (m, 1H), 4.77 (t, 2H), 4.58 (t, 2H). LC-MS, single peak monitoring at 254 nm. Chemical Formula: C18H15ClFN5O3S, MS (ESI) m/z: [M+H] calcd: 436. found 436.

4-(4-(3-(2-chloro-4-fluorophenyl)ureido)-1H-pyrazol-1-yl)-N-(oxetan-3-yl)thiophene-2-carboxamide (26)

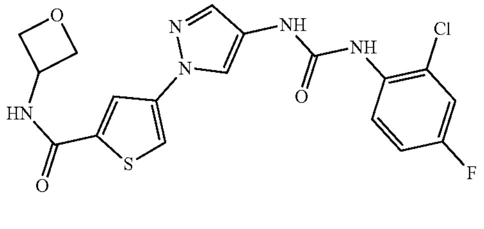 [SMILES: O=C(Nc1cnn(-c2csc(C(=O)NC3COC3)c2)c1)Nc1ccc(F)cc1Cl]

Scheme 1 was used to prepare 26. $^1$H-NMR (400 MHz, DMSO): δ 9.31 (s, 2H), 8.33-8.38 (t, 3H), 8.10-8.14 (m, 1H), 7.91 (s, 1H), 7.73 (s, 1H), 7.46-7.49 (m, 1H), 7.19-7.24 (m, 1H), 4.96-5.00 (m, 1H), 4.77-4.80 (t, 2H), 4.58-4.61 (t, 2H). LC-MS, single peak monitoring at 254 nm. Chemical Formula: C18H15ClFN5O3S, MS (ESI) m/z: [M+H] calcd: 436. found 436.

4-(4-(3-(2-chloro-6-fluorophenyl)ureido)-1H-pyrazol-1-yl)-5-methyl-N-(oxetan-3-yl)thiophene-2-carboxamide (27)

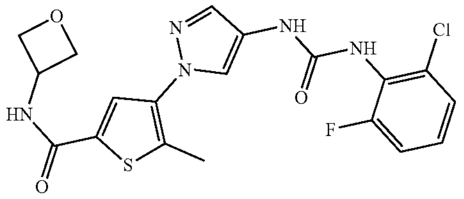 [SMILES: Cc1sc(C(=O)NC2COC2)cc1-n1cc(NC(=O)Nc2c(F)cccc2Cl)cn1]

Scheme 1 was used to prepare 27. $^1$H-NMR (400 MHz, DMSO): δ 9.15 (d, J=6.8 Hz, 1H), 8.90 (s, 1H), 8.24 (s, 1H), 8.10 (s, 1H), 8.02 (s, 1H), 7.71 (s, 1H), 7.26-7.40 (m, 3H), 4.92-4.99 (m, 1H), 4.76 (t, J=7.0 Hz, 2H), 4.56 (t, J=6.4 Hz, 2H), 2.52 (s, 3H). LC-MS, single peak monitoring at 254 nm. Chemical Formula: C19H17ClFN5O3S, MS (ESI) m/z: [M+H] calcd: 450; found 450.

(R)-4-(4-(3-(2-chloro-6-fluorophenyl)ureido)-1H-pyrazol-1-yl)-5-methyl-N-(tetrahydrofuran-3-yl)thiophene-2-carboxamide (28)

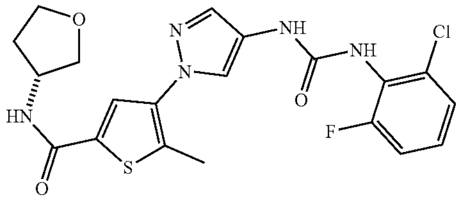

Scheme 1 was used to prepare 28. $^1$H-NMR (400 MHz, DMSO): δ 8.90 (s, 1H), 8.59 (d, J=6.4 Hz, 1H), 8.24 (s, 1H), 8.09 (s, 1H), 8.02 (s, 1H), 7.70 (s, 1H), 7.26-7.39 (m, 3H), 4.37-4.44 (m, 1H), 3.80-3.87 (m, 2H), 3.68-3.73 (m, 1H), 3.55-3.59 (m, 1H), 2.51 (s, 3H), 2.10-2.19 (m, 1H), 1.84-1.91 (m, 1H). LC-MS, single peak monitoring at 254 nm. Chemical Formula: C20H19ClFN5O3S, MS (ESI) m/z: [M+H] calcd: 464. found 464.

2.1 JNK-1/2/3 and p38 Assays

Homogeneous Time-resolved Fluorescence Assay-Enzyme inhibition studies were performed in 384-well polystyrene homogeneous time-resolved fluorescence plates (Grainier) for 1 hr. at ambient temperature (~22° C.) with 0.5 μM biotinylated FL-ATF-2, 1.25 μM ATP, 0.75 nM activated JNK3α1 (with a control in the absence of kinase for determining the basal signal), JNK2, or JNK1 in 10-μl volumes containing the final concentrations of the following: 50 mM Hepes, pH 7.0, 2.5 mM $MgCl_2$, 0.1 mg/ml bovine serum albumin, 1 mM DL-dithiothreitol, 0.01% Triton X-100 (all from Sigma-Aldrich), and 5% DMSO (with or without compound). A 10-point titration of all compounds was carried out in 3-fold dilutions from 10 μM to 0.5 nM. After 22 min, the kinase reaction was terminated by addition of 10 μl of quenching solution (1× Lance Buffer, detection reagents, streptavidin-xIAPC (200 nM) and europium cryptate-labeled rabbit polyclonal anti-phospho-ATF-2 (1 nM), were from Cis-Bio. The homogeneous time-resolved fluorescence signal was detected using an EnVision plate reader 1 hr post-quenching. The data from four different experiments were averaged and presented as the mean±S.D. $IC_{50}$ values were determined by fitting the data to the equation for a four-parameter logistic.

2.2 JNK3 Inhibition Assays in Rat Primary Neuron Cultures

Both hippocampal and cortical neurons were isolated from E18 rat embryos and cultured in NbActive 1 medium that contains B27 (Brainbits, LLC) plus penicillin/streptomycin (Life Technologies). At the $7^{th}$ day in culture, cells were treated with different concentrations of inhibitors diluted in DMSO and 80 ng/ml Anisomycin for 30 min to activate the endogenous JNK3. At the end of incubation time, whole cell lysates were prepared in RIPA buffer containing 50 mM Tris (pH 8.0), 150 mM NaCl, 2 mM EDTA, 1% NP-40, 0.5% deoxycholate supplemented with 10 mM Na pyrophosphate, 1 mM sodium orthovanadate, 25 mM NaF, 10 μg/ml leupeptin, 10 μg/ml aprotinin, 1 mM β-glycerophosphate, and 2 mM PMSF. The lysates were subjected to Western blotting to detect whether inhibitors block JNK3-dependent phosphorylation of APP at T668 and c-jun at S73. Phospho-$APP^{T668}$, phosphor-c-$jun^{S73}$, APP, and c-jun antibodies were from Cell Signaling Technology.

2.3 MTT Cytotoxicity Assay

SHSY5Y cells were cultured in DMEM/F12 (Life Technologies) supplemented with 10% fetal bovine serum (FBS) and penicillin/streptomycin. A day before the assay, cells were plated at 50,000/well in 96 well plates in the culture medium. Next day, compounds were added at 10 μM final concentration, and cells were incubated for 48 hrs at 37° C. After the incubation, cells were subjected to MTT assay using Vybrant MTT Cell Proliferation kit as directed by the vendor (Life Technologies).

2.4 Kinase Panel Profiling Studies

The wild-type kinase panel of Reaction Biology Corporation (www.reactionbiology.com) (374 kinases which does not including those lipophilic kinases) was used to perform the profiling studies. An inhibitor concentration of >100-fold of its JNK3 $IC_{50}$ value was generally used in the profiling. Detailed profiling data for inhibitors 17, 25 and 27 are shown in the Table 1.

TABLE 1

| | % Enzyme Activity (relative to DMSO controls) | | | | | |
|---|---|---|---|---|---|---|
| | Compound 17 (5 uM) | | Compound 25 (5 uM) | | Compound 27 (10 uM) | |
| Kinase: | Data 1 | Data 2 | Data 1 | Data 2 | Data 1 | Data 2 |
| ABL1 | 83.38 | 82.39 | 100.85 | 99.61 | 101.96 | 101.15 |
| ABL2/ARG | 92.71 | 92.27 | 88.74 | 84.21 | 122.68 | 122.22 |
| ACK1 | 85.64 | 85.44 | 94.57 | 85.87 | 106.16 | 98.53 |
| AKT1 | 95.44 | 94.02 | 105.05 | 102.94 | 104.78 | 101.26 |
| AKT2 | 89.50 | 88.19 | 104.39 | 103.87 | 89.76 | 88.94 |
| AKT3 | 87.30 | 84.52 | 97.63 | 96.98 | 94.84 | 94.19 |
| ALK | 101.15 | 99.78 | 89.19 | 84.18 | 100.18 | 99.92 |
| ALK1/ACVRL1 | 107.21 | 103.64 | 120.21 | 119.05 | 78.71 | 78.63 |
| ALK2/ACVR1 | 104.72 | 104.38 | 95.68 | 95.05 | 107.63 | 104.44 |
| ALK3/BMPR1A | 105.42 | 104.59 | 102.62 | 99.98 | 92.49 | 84.86 |
| ALK4/ACVR1B | 123.55 | 112.23 | 82.02 | 80.08 | 78.52 | 78.37 |
| ALK5/TGFBR1 | 102.96 | 101.31 | 97.42 | 97.31 | 104.00 | 103.56 |
| ALK6/BMPR1B | 108.84 | 107.90 | 114.21 | 111.40 | 103.88 | 100.94 |
| ARAF | 95.08 | 91.90 | 94.43 | 92.64 | 84.06 | 83.25 |
| ARK5/NUAK1 | 97.91 | 97.71 | 95.21 | 94.11 | 96.93 | 96.10 |
| ASK1/MAP3K5 | 91.18 | 87.11 | 91.07 | 89.42 | 94.02 | 89.70 |
| Aurora A | 105.35 | 105.00 | 83.13 | 82.07 | 88.44 | 85.37 |
| Aurora B | 93.04 | 91.41 | 69.79 | 68.59 | 96.38 | 94.10 |
| Aurora C | 104.47 | 99.98 | 58.49 | 58.15 | 104.19 | 101.47 |
| AXL | 96.72 | 93.82 | 73.03 | 71.80 | 86.60 | 85.74 |
| BLK | 79.19 | 77.85 | 96.11 | 95.53 | 111.64 | 110.69 |
| BMPR2 | 109.83 | 99.57 | 77.18 | 74.94 | 84.46 | 78.97 |
| BMX/ETK | 106.00 | 99.36 | 96.84 | 94.77 | 92.91 | 91.90 |
| BRAF | 93.33 | 86.38 | 99.94 | 97.46 | 104.84 | 100.71 |
| BRK | 118.11 | 100.93 | 85.73 | 85.37 | 78.89 | 77.07 |
| BRSK1 | 85.45 | 84.52 | 99.37 | 99.31 | 87.80 | 84.97 |
| BRSK2 | 101.84 | 100.62 | 100.00 | 98.75 | 101.58 | 99.81 |
| BTK | 92.58 | 91.63 | 89.33 | 89.05 | 87.63 | 86.96 |
| c-Kit | 89.25 | 88.34 | 94.05 | 93.89 | 64.36 | 63.84 |
| c-MER | 92.67 | 92.36 | 77.10 | 76.05 | 102.90 | 100.99 |
| c-MET | 101.60 | 100.21 | 86.10 | 84.17 | 76.98 | 74.48 |
| c-Src | 91.06 | 85.52 | 98.44 | 97.60 | 96.57 | 96.02 |
| CAMK1a | 87.10 | 85.37 | 97.98 | 97.46 | 114.97 | 113.30 |
| CAMK1b | 96.26 | 92.06 | 102.48 | 101.77 | 80.14 | 74.09 |
| CAMK1d | 103.67 | 101.19 | 99.58 | 98.89 | 104.84 | 104.05 |
| CAMK1g | 94.21 | 94.01 | 93.95 | 91.73 | 93.14 | 92.52 |
| CAMK2a | 100.41 | 99.62 | 99.44 | 98.52 | 99.68 | 98.98 |
| CAMK2b | 104.90 | 103.78 | 99.09 | 95.67 | 100.05 | 99.77 |
| CAMK2d | 102.59 | 102.33 | 93.47 | 92.93 | 91.34 | 90.36 |
| CAMK2g | 96.39 | 94.54 | 90.14 | 89.86 | 102.19 | 99.23 |
| CAMK4 | 114.38 | 103.67 | 98.67 | 97.56 | 98.49 | 96.54 |
| CAMKK1 | 130.50 | 128.91 | 93.74 | 93.63 | 121.11 | 116.36 |
| CAMKK2 | 91.14 | 84.08 | 80.99 | 78.68 | 111.01 | 109.73 |
| CDC7/DBF4 | 110.97 | 108.83 | 84.27 | 81.54 | 106.89 | 99.54 |
| CDK1/cyclin A | 95.46 | 94.64 | 86.35 | 85.97 | 105.30 | 103.17 |

TABLE 1-continued

| | % Enzyme Activity (relative to DMSO controls) | | | | | |
|---|---|---|---|---|---|---|
| | Compound 17 (5 uM) | | Compound 25 (5 uM) | | Compound 27 (10 uM) | |
| Kinase: | Data 1 | Data 2 | Data 1 | Data 2 | Data 1 | Data 2 |
| CDK1/cyclin B | 92.57 | 91.19 | 105.47 | 105.10 | 92.73 | 92.47 |
| CDK1/cyclin E | 94.72 | 86.44 | 98.36 | 95.05 | 100.09 | 97.13 |
| CDK14/cyclin Y (PFTK1) | 106.61 | 105.71 | 110.11 | 103.59 | 100.37 | 95.26 |
| CDK16/cyclin Y (PCTAIRE) | 94.81 | 93.16 | 101.27 | 100.38 | 101.76 | 93.30 |
| CDK17/cyclin Y (PCTK2) | 106.10 | 105.77 | 96.03 | 94.30 | 102.18 | 101.79 |
| CDK18/cyclin Y (PCTK3) | 101.21 | 98.85 | 91.93 | 89.49 | 118.84 | 117.76 |
| CDK19/cyclin C | 104.67 | 104.15 | 96.17 | 93.31 | 98.09 | 96.75 |
| CDK2/cyclin A | 93.61 | 92.31 | 93.81 | 91.26 | 98.34 | 98.06 |
| CDK2/Cyclin A1 | 105.66 | 100.91 | 94.17 | 91.11 | 110.76 | 110.18 |
| CDK2/cyclin E | 98.99 | 97.70 | 94.59 | 93.28 | 106.26 | 103.08 |
| CDK2/cyclin E2 | 106.94 | 101.91 | 98.88 | 96.32 | 90.79 | 89.27 |
| CDK2/cyclin O | 93.24 | 91.32 | 94.07 | 93.54 | 105.25 | 105.15 |
| CDK3/cyclin E | 106.51 | 103.23 | 92.16 | 90.92 | 91.20 | 90.95 |
| CDK3/cyclin E2 | 95.81 | 95.18 | 109.45 | 102.15 | 102.60 | 99.40 |
| CDK4/cyclin D1 | 92.21 | 90.56 | 90.27 | 90.16 | 78.01 | 72.89 |
| CDK4/cyclin D3 | 98.21 | 96.07 | 79.41 | 78.31 | 96.53 | 94.52 |
| CDK5/P25 | 101.10 | 101.02 | 88.15 | 87.76 | 97.64 | 97.00 |
| CDK5/p35 | 95.38 | 94.35 | 94.35 | 94.17 | 102.73 | 101.68 |
| CDK6/cyclin D1 | 95.43 | 95.10 | 105.31 | 101.02 | 101.25 | 95.95 |
| CDK6/cyclin D3 | 113.72 | 108.98 | 92.62 | 92.38 | 95.20 | 93.51 |
| CDK7/cyclin H | 99.70 | 96.56 | 95.80 | 94.87 | 102.77 | 101.79 |
| CDK8/cyclin C | 101.20 | 100.48 | 99.05 | 98.79 | 92.65 | 91.81 |
| CDK9/cyclin K | 100.31 | 92.42 | 120.29 | 119.71 | 85.36 | 85.02 |
| CDK9/cyclin T1 | 80.17 | 78.30 | 96.07 | 95.78 | 107.15 | 106.08 |
| CDK9/cyclin T2 | 91.08 | 87.96 | 92.98 | 90.35 | 101.18 | 97.27 |
| CHK1 | 98.73 | 97.38 | 141.35 | 138.23 | 117.85 | 112.53 |
| CHK2 | 97.83 | 94.70 | 91.47 | 89.85 | 95.15 | 93.80 |
| CK1a1 | 98.47 | 93.32 | 76.62 | 74.42 | 81.09 | 80.23 |
| CK1a1L | 109.15 | 106.14 | 81.14 | 80.89 | 104.98 | 104.70 |
| CK1d | 100.73 | 100.16 | 116.74 | 111.80 | 111.63 | 106.74 |
| CK1epsilon | 89.59 | 88.97 | 88.62 | 87.18 | 97.93 | 97.52 |
| CK1g1 | 99.02 | 95.46 | 102.18 | 101.70 | 100.79 | 97.70 |
| CK1g2 | 98.47 | 94.22 | 90.24 | 89.00 | 103.84 | 99.09 |
| CK1g3 | 103.19 | 100.86 | 92.58 | 91.24 | 91.28 | 90.51 |
| CK2a | 95.35 | 71.10 | 90.53 | 87.51 | 96.99 | 96.34 |
| CK2a2 | 97.32 | 94.89 | 96.58 | 95.95 | 95.49 | 93.35 |
| CLK1 | 80.96 | 80.50 | 74.91 | 74.16 | 98.36 | 96.78 |
| CLK2 | 103.48 | 103.14 | 112.33 | 108.85 | 104.91 | 99.95 |
| CLK3 | 120.16 | 117.28 | 93.46 | 90.44 | 99.57 | 96.35 |
| CLK4 | 66.05 | 63.23 | 93.23 | 92.90 | 101.58 | 101.37 |
| COT1/MAP3K8 | 92.74 | 92.01 | 93.58 | 87.64 | 104.85 | 104.84 |
| CSK | 99.19 | 98.31 | 97.48 | 96.48 | 97.97 | 94.91 |
| CTK/MATK | 99.69 | 97.17 | 100.13 | 99.12 | 97.76 | 97.28 |
| DAPK1 | 104.08 | 98.58 | 98.93 | 97.01 | 104.44 | 101.73 |
| DAPK2 | 102.82 | 101.59 | 101.91 | 97.72 | 99.54 | 97.33 |
| DCAMKL1 | 99.25 | 94.99 | 84.20 | 83.29 | 67.21 | 66.10 |
| DCAMKL2 | 99.89 | 97.52 | 94.31 | 91.97 | 106.96 | 105.46 |
| DDR1 | 98.38 | 95.87 | 88.88 | 84.28 | 83.65 | 83.36 |
| DDR2 | 99.83 | 98.92 | 96.59 | 94.12 | 110.69 | 104.24 |
| DLK/MAP3K12 | 96.45 | 92.39 | 82.16 | 81.42 | | |
| DMPK | 101.81 | 101.43 | 110.50 | 110.17 | 95.21 | 94.17 |
| DMPK2 | 86.96 | 85.52 | 118.65 | 115.14 | 117.81 | 100.83 |
| DRAK1/STK17A | 98.39 | 98.34 | 89.43 | 89.42 | 111.19 | 107.90 |
| DYRK1/DYRK1A | 85.97 | 85.45 | 75.09 | 74.37 | 95.47 | 94.26 |
| DYRK1B | 87.00 | 86.59 | 82.78 | 82.19 | 105.31 | 104.26 |
| DYRK2 | 88.23 | 87.06 | 93.61 | 91.95 | 96.34 | 95.63 |
| DYRK3 | 93.30 | 92.61 | 99.24 | 99.09 | 101.28 | 99.17 |
| DYRK4 | 94.62 | 91.60 | 96.15 | 93.54 | 93.69 | 87.29 |
| EGFR | 99.67 | 98.74 | 89.44 | 85.58 | 98.46 | 95.17 |
| EPHA1 | 99.09 | 98.05 | 88.36 | 87.48 | 88.49 | 86.42 |
| EPHA2 | 101.18 | 95.39 | 97.87 | 97.57 | 101.94 | 100.00 |
| EPHA3 | 103.87 | 102.79 | 96.14 | 95.44 | 109.05 | 104.71 |
| EPHA4 | 100.36 | 98.18 | 89.09 | 87.82 | 116.16 | 113.09 |
| EPHA5 | 96.92 | 93.87 | 95.00 | 92.04 | 105.51 | 103.31 |
| EPHA6 | 99.53 | 99.03 | 95.69 | 95.27 | 80.19 | 78.80 |
| EPHA7 | 102.97 | 100.96 | 91.24 | 89.79 | 98.64 | 95.88 |
| EPHA8 | 102.53 | 101.47 | 93.83 | 92.71 | 91.74 | 90.38 |
| EPHB1 | 100.48 | 99.40 | 96.08 | 92.94 | 100.29 | 98.70 |
| EPHB2 | 101.07 | 99.31 | 99.86 | 98.31 | 109.04 | 107.17 |
| EPHB3 | 95.57 | 84.83 | 96.46 | 95.92 | 97.24 | 95.82 |

TABLE 1-continued

| | % Enzyme Activity (relative to DMSO controls) | | | | | |
|---|---|---|---|---|---|---|
| | Compound 17 (5 uM) | | Compound 25 (5 uM) | | Compound 27 (10 uM) | |
| Kinase: | Data 1 | Data 2 | Data 1 | Data 2 | Data 1 | Data 2 |
| EPHB4 | 97.85 | 97.02 | 98.09 | 94.70 | 93.73 | 93.67 |
| ERBB2/HER2 | 102.80 | 100.91 | 97.00 | 95.53 | 64.09 | 63.27 |
| ERBB4/HER4 | 105.02 | 103.78 | 101.85 | 100.85 | 95.04 | 94.58 |
| ERK1 | 92.80 | 90.11 | 92.37 | 92.07 | 107.04 | 106.53 |
| ERK2/MAPK1 | 109.74 | 104.15 | 85.88 | 83.94 | 90.75 | 85.53 |
| ERK5/MAPK7 | 118.72 | 110.13 | 75.94 | 71.15 | 95.68 | 95.01 |
| ERK7/MAPK15 | 140.43 | 122.73 | 107.57 | 104.76 | 103.00 | 100.48 |
| ERN1/IRE1 | 94.29 | 93.93 | 95.84 | 94.61 | 94.09 | 93.26 |
| ERN2/IRE2 | 100.11 | 100.06 | 100.33 | 98.47 | 80.71 | 67.84 |
| FAK/PTK2 | 95.65 | 95.10 | 88.95 | 87.53 | 104.00 | 103.33 |
| FER | 101.03 | 100.17 | 89.79 | 89.16 | 89.98 | 89.54 |
| FES/FPS | 99.35 | 96.09 | 87.84 | 83.88 | 93.73 | 93.20 |
| FGFR1 | 98.53 | 95.93 | 93.20 | 91.44 | 114.41 | 111.37 |
| FGFR2 | 95.60 | 94.71 | 103.03 | 102.55 | 105.57 | 105.21 |
| FGFR3 | 97.78 | 84.94 | 92.01 | 90.95 | 137.06 | 136.20 |
| FGFR4 | 88.21 | 88.01 | 99.57 | 98.51 | 96.76 | 94.67 |
| FGR | 90.00 | 89.22 | 95.53 | 95.52 | 80.17 | 70.96 |
| FLT1/VEGFR1 | 101.29 | 96.75 | 86.06 | 82.27 | 84.13 | 82.63 |
| FLT3 | 89.66 | 88.39 | 99.15 | 98.71 | 69.13 | 68.41 |
| FLT4/VEGFR3 | 93.81 | 93.50 | 86.58 | 86.16 | 81.92 | 79.20 |
| FMS | 105.23 | 104.80 | 98.87 | 97.36 | 103.26 | 100.68 |
| FRK/PTK5 | 97.37 | 96.66 | 95.63 | 95.58 | 87.35 | 86.33 |
| FYN | 97.83 | 91.46 | 90.28 | 88.53 | 99.85 | 97.10 |
| GCK/MAP4K2 | 104.91 | 101.55 | 95.33 | 90.96 | 90.19 | 88.53 |
| GLK/MAP4K3 | 97.50 | 96.25 | 100.27 | 99.15 | 117.79 | 117.10 |
| GRK1 | 91.88 | 91.85 | 92.91 | 92.72 | 112.87 | 108.66 |
| GRK2 | 96.08 | 96.04 | 106.16 | 104.29 | 106.27 | 106.21 |
| GRK3 | 102.23 | 102.06 | 101.19 | 100.13 | 106.77 | 104.98 |
| GRK4 | 97.03 | 93.20 | 93.61 | 93.46 | 112.87 | 107.95 |
| GRK5 | 97.97 | 97.86 | 101.75 | 100.70 | 112.82 | 110.81 |
| GRK6 | 97.93 | 97.75 | 102.38 | 97.97 | 91.45 | 89.66 |
| GRK7 | 96.38 | 94.88 | 94.04 | 92.57 | 99.89 | 98.35 |
| GSK3a | 97.42 | 97.03 | 93.53 | 93.48 | 128.22 | 128.04 |
| GSK3b | 94.97 | 94.45 | 95.66 | 94.78 | 94.86 | 94.56 |
| Haspin | 111.79 | 109.87 | 110.88 | 108.04 | 92.41 | 92.33 |
| HCK | 94.03 | 89.72 | 91.33 | 90.95 | 95.04 | 92.55 |
| HGK/MAP4K4 | 81.09 | 80.14 | 90.41 | 81.60 | 93.42 | 92.65 |
| HIPK1 | 96.26 | 92.79 | 91.66 | 91.33 | 115.54 | 114.53 |
| HIPK2 | 101.63 | 100.28 | 92.56 | 92.50 | 102.68 | 98.63 |
| HIPK3 | 97.62 | 96.89 | 98.77 | 96.59 | 88.47 | 84.89 |
| HIPK4 | 100.37 | 97.20 | 110.76 | 103.92 | 98.39 | 97.39 |
| HPK1/MAP4K1 | 132.29 | 127.20 | 92.66 | 89.08 | 99.22 | 95.40 |
| IGF1R | 95.83 | 94.87 | 94.86 | 94.40 | 101.94 | 101.66 |
| IKKa/CHUK | 167.10 | 144.34 | 107.75 | 105.68 | 100.80 | 93.70 |
| IKKb/IKBKB | 95.58 | 95.22 | 94.67 | 94.13 | 86.76 | 82.06 |
| IKKe/IKBKE | 110.26 | 108.28 | 96.80 | 95.05 | 115.84 | 114.63 |
| IR | 98.37 | 95.58 | 101.73 | 97.94 | 85.46 | 84.44 |
| IRAK1 | 112.23 | 107.37 | 107.05 | 105.55 | 79.94 | 78.52 |
| IRAK4 | 92.12 | 88.09 | 97.83 | 97.00 | 103.45 | 102.26 |
| IRR/INSRR | 95.98 | 93.76 | 75.90 | 70.29 | 71.87 | 70.84 |
| ITK | 106.70 | 99.31 | 92.77 | 92.29 | 94.41 | 91.41 |
| JAK1 | 98.67 | 94.40 | 107.40 | 103.94 | 72.22 | 71.47 |
| JAK2 | 98.19 | 95.41 | 96.46 | 88.12 | 95.04 | 94.99 |
| JAK3 | 102.01 | 100.23 | 98.66 | 96.18 | 96.73 | 95.21 |
| JNK1 | 57.60 | 55.85 | 49.13 | 47.91 | 76.30 | 74.25 |
| JNK2 | 34.12 | 33.90 | 22.70 | 21.84 | 51.87 | 50.09 |
| JNK3 | 7.81 | 6.08 | 8.85 | 8.76 | 10.47 | 9.63 |
| KDR/VEGFR2 | 95.19 | 94.57 | 88.29 | 87.45 | 88.22 | 87.45 |
| KHS/MAP4K5 | 99.13 | 94.61 | 102.78 | 102.05 | 98.39 | 96.58 |
| KSR1 | 100.82 | 100.22 | 104.82 | 100.19 | 102.95 | 102.74 |
| KSR2 | 106.91 | 104.96 | 92.66 | 91.89 | 99.22 | 94.21 |
| LATS1 | 105.98 | 105.37 | 93.53 | 92.23 | 97.22 | 96.57 |
| LATS2 | 95.97 | 92.68 | 103.57 | 101.69 | 94.69 | 94.42 |
| LCK | 99.10 | 91.26 | 94.20 | 92.42 | 46.53 | 44.32 |
| LCK2/ICK | 112.41 | 110.26 | 100.84 | 96.59 | 100.39 | 100.15 |
| LIMK1 | 96.16 | 96.01 | 104.47 | 98.61 | 104.69 | 104.17 |
| LIMK2 | 96.76 | 96.21 | 93.98 | 93.07 | 112.92 | 98.20 |
| LKB1 | 118.26 | 115.31 | 94.65 | 94.10 | 97.61 | 96.97 |
| LOK/STK10 | 87.86 | 87.02 | 88.98 | 87.45 | 96.39 | 95.76 |
| LRRK2 | 88.23 | 87.94 | 91.27 | 90.24 | 101.06 | 100.86 |
| LYN | 96.75 | 94.36 | 95.30 | 93.32 | 105.59 | 103.36 |
| LYN B | 94.68 | 93.09 | 87.31 | 82.84 | 88.78 | 86.83 |
| MAK | 98.82 | 98.63 | 97.56 | 96.43 | 119.88 | 110.01 |
| MAPKAPK2 | 97.08 | 95.77 | 99.85 | 92.89 | 93.57 | 89.94 |

TABLE 1-continued

| | % Enzyme Activity (relative to DMSO controls) | | | | | |
|---|---|---|---|---|---|---|
| | Compound 17 (5 uM) | | Compound 25 (5 uM) | | Compound 27 (10 uM) | |
| Kinase: | Data 1 | Data 2 | Data 1 | Data 2 | Data 1 | Data 2 |
| MAPKAPK3 | 83.54 | 77.32 | 95.64 | 92.60 | 109.92 | 108.41 |
| MAPKAPK5/PRAK | 92.82 | 91.04 | 99.73 | 96.33 | 96.47 | 95.33 |
| MARK1 | 96.35 | 93.65 | 108.08 | 107.68 | 95.34 | 95.19 |
| MARK2/PAR-1Ba | 104.31 | 104.12 | 90.71 | 89.37 | 99.82 | 97.94 |
| MARK3 | 98.23 | 97.73 | 99.34 | 98.43 | 101.51 | 100.16 |
| MARK4 | 107.82 | 101.29 | 97.91 | 97.87 | 108.32 | 107.61 |
| MAST3 | | | 108.27 | 104.14 | 96.70 | 95.18 |
| MASTL | 96.74 | 96.59 | 93.69 | 93.53 | 110.07 | 108.24 |
| MEK1 | 103.88 | 101.93 | 107.16 | 106.60 | 95.52 | 92.97 |
| MEK2 | 92.15 | 91.56 | 90.56 | 87.91 | 99.54 | 97.50 |
| MEK3 | 103.66 | 103.65 | 110.84 | 98.78 | 88.77 | 81.98 |
| MEK5 | 98.20 | 98.01 | 103.04 | 99.33 | 96.85 | 89.58 |
| MEKK1 | 103.43 | 103.38 | 98.70 | 98.46 | 94.54 | 91.66 |
| MEKK2 | 110.44 | 103.97 | 80.13 | 78.60 | 88.07 | 88.06 |
| MEKK3 | 112.66 | 105.89 | 81.92 | 80.44 | 113.33 | 108.54 |
| MEKK6 | 98.85 | 94.33 | 92.50 | 90.69 | 79.33 | 77.68 |
| MELK | 48.70 | 48.18 | 61.40 | 59.61 | 102.99 | 100.16 |
| MINK/MINK1 | 79.36 | 78.64 | 62.22 | 57.78 | 102.17 | 101.98 |
| MKK4 | 113.08 | 111.42 | 133.47 | 128.10 | 93.03 | 93.02 |
| MKK6 | 96.44 | 95.10 | 94.41 | 84.96 | 86.38 | 85.38 |
| MKK7 | 112.18 | 109.33 | 135.29 | 134.99 | 119.77 | 115.05 |
| MLCK/MYLK | 97.51 | 94.38 | 95.87 | 92.85 | 102.60 | 102.42 |
| MLCK2/MYLK2 | 89.90 | 89.22 | 83.54 | 79.44 | 78.65 | 78.49 |
| MLK1/MAP3K9 | 95.06 | 94.25 | 88.47 | 88.03 | 87.52 | 87.12 |
| MLK2/MAP3K10 | 98.47 | 98.09 | 94.31 | 92.29 | 90.80 | 88.47 |
| MLK3/MAP3K11 | 93.45 | 92.56 | 84.69 | 83.36 | 90.67 | 86.28 |
| MLK4 | 93.15 | 92.52 | 94.32 | 94.11 | 85.24 | 83.89 |
| MNK1 | 94.27 | 94.24 | 103.28 | 103.05 | 94.15 | 93.25 |
| MNK2 | 99.35 | 96.75 | 90.79 | 90.66 | 83.39 | 79.46 |
| MRCKa/CDC42BPA | 99.34 | 96.17 | 98.97 | 97.51 | 104.07 | 101.90 |
| MRCKb/CDC42BPB | 97.10 | 95.66 | 89.02 | 84.42 | 111.73 | 111.02 |
| MSK1/RPS6KA5 | 89.48 | 87.65 | 104.50 | 101.01 | 111.30 | 103.83 |
| MSK2/RPS6KA4 | 90.68 | 90.63 | 99.85 | 99.35 | 104.68 | 104.36 |
| MSSK1/STK23 | 91.94 | 90.93 | 89.79 | 85.70 | 98.87 | 92.65 |
| MST1/STK4 | 99.29 | 94.51 | 96.62 | 92.82 | 107.06 | 105.79 |
| MST2/STK3 | 119.51 | 116.20 | 93.18 | 93.01 | 93.94 | 92.76 |
| MST3/STK24 | 113.14 | 110.47 | 81.61 | 81.18 | 67.27 | 63.25 |
| MST4 | 98.26 | 94.12 | 71.40 | 69.65 | 72.41 | 71.35 |
| MUSK | 94.45 | 91.22 | 86.81 | 86.23 | 103.41 | 102.42 |
| MYLK3 | 95.09 | 90.49 | 101.81 | 92.13 | 111.63 | 109.69 |
| MYLK4 | 85.24 | 83.36 | 91.73 | 90.80 | 108.71 | 108.51 |
| MYO3A | 94.53 | 91.46 | 82.83 | 75.76 | 91.09 | 88.15 |
| MYO3b | 128.21 | 125.72 | 100.86 | 95.64 | 78.67 | 73.50 |
| NEK1 | 115.21 | 111.73 | 77.17 | 68.70 | 90.41 | 89.34 |
| NEK11 | 144.68 | 136.40 | 89.55 | 88.71 | 70.00 | 63.48 |
| NEK2 | 104.16 | 102.20 | 96.24 | 93.32 | 88.02 | 84.41 |
| NEK3 | 102.58 | 98.96 | 87.25 | 82.26 | 87.45 | 86.55 |
| NEK4 | 108.95 | 106.86 | 90.82 | 89.09 | 75.55 | 75.28 |
| NEK5 | 110.33 | 107.26 | 88.09 | 87.92 | 105.32 | 102.25 |
| NEK6 | 102.77 | 99.56 | 87.15 | 86.75 | 93.27 | 92.66 |
| NEK7 | 101.79 | 101.22 | 88.11 | 87.60 | 100.04 | 95.94 |
| NEK8 | 107.28 | 106.90 | | | | |
| NEK9 | 104.35 | 104.34 | 88.36 | 85.75 | 111.28 | 110.53 |
| NIM1 | 101.39 | 101.29 | 70.72 | 69.78 | 107.17 | 107.12 |
| NLK | 99.47 | 96.41 | 87.41 | 87.33 | 85.15 | 83.86 |
| OSR1/OXSR1 | 92.58 | 92.43 | 96.51 | 91.54 | 126.78 | 118.37 |
| P38a/MAPK14 | 141.98 | 140.87 | 104.85 | 103.81 | 93.16 | 85.97 |
| P38b/MAPK11 | 100.86 | 98.03 | 91.71 | 88.84 | 94.33 | 88.02 |
| P38d/MAPK13 | 122.26 | 119.83 | 98.42 | 91.95 | 89.20 | 85.65 |
| P38g | 99.37 | 94.52 | 98.27 | 97.49 | 90.47 | 80.85 |
| p70S6K/RPS6KB1 | 92.11 | 91.11 | 97.74 | 97.56 | 92.12 | 91.12 |
| p70S6Kb/RPS6KB2 | 94.17 | 94.02 | 101.38 | 99.90 | 98.93 | 97.40 |
| PAK1 | 106.01 | 103.66 | 81.20 | 76.08 | 103.67 | 98.15 |
| PAK2 | 90.11 | 86.23 | 95.31 | 92.21 | 105.80 | 103.94 |
| PAK3 | 97.39 | 96.80 | 64.23 | 62.40 | 113.75 | 108.53 |
| PAK4 | 98.87 | 92.17 | 106.73 | 104.75 | 106.39 | 103.46 |
| PAK5 | 92.12 | 90.70 | 92.86 | 92.78 | 103.47 | 103.05 |
| PAK6 | 130.58 | 127.00 | 92.92 | 88.33 | 99.92 | 99.07 |
| PASK | 96.31 | 94.19 | 99.72 | 93.30 | 96.14 | 92.92 |
| PBK/TOPK | 114.88 | 111.94 | 98.16 | 95.69 | 88.48 | 86.39 |
| PDGFRa | 95.25 | 91.67 | 106.99 | 105.80 | 114.34 | 101.61 |
| PDGFRb | 107.18 | 98.53 | 100.99 | 92.40 | 97.93 | 88.31 |
| PDK1/PDPK1 | 100.87 | 94.26 | 99.58 | 99.08 | 99.18 | 95.19 |
| PEAK1 | 91.36 | 90.97 | | | | |

TABLE 1-continued

| | % Enzyme Activity (relative to DMSO controls) | | | | | |
|---|---|---|---|---|---|---|
| | Compound 17 (5 uM) | | Compound 25 (5 uM) | | Compound 27 (10 uM) | |
| Kinase: | Data 1 | Data 2 | Data 1 | Data 2 | Data 1 | Data 2 |
| PHKg1 | 101.60 | 100.36 | 91.24 | 90.46 | 83.95 | 83.21 |
| PHKg2 | 100.57 | 98.24 | 131.01 | 127.31 | 88.50 | 80.45 |
| PIM1 | 64.61 | 64.36 | 73.33 | 72.49 | 95.09 | 93.11 |
| PIM2 | 96.37 | 96.02 | 128.59 | 126.93 | 96.51 | 95.53 |
| PIM3 | 61.24 | 60.47 | 73.91 | 73.07 | 128.82 | 126.62 |
| PKA | 99.81 | 96.77 | 107.72 | 102.18 | 94.54 | 92.47 |
| PKAcb | 98.97 | 97.74 | 98.29 | 86.39 | 104.28 | 104.11 |
| PKAcg | 104.45 | 101.81 | 97.57 | 97.05 | 99.03 | 97.39 |
| PKCa | 101.32 | 100.41 | 90.65 | 90.27 | 95.91 | 92.54 |
| PKCb1 | 101.55 | 100.64 | 100.22 | 98.69 | 110.62 | 104.62 |
| PKCb2 | 102.73 | 102.48 | 98.95 | 98.60 | 98.35 | 96.76 |
| PKCd | 112.31 | 107.07 | 101.26 | 100.19 | 98.01 | 95.12 |
| PKCepsilon | 101.98 | 98.35 | 94.25 | 92.54 | 101.17 | 99.42 |
| PKCeta | 102.59 | 100.01 | 99.05 | 97.40 | 91.56 | 84.37 |
| PKCg | 97.98 | 97.24 | 98.35 | 95.74 | 101.69 | 100.79 |
| PKCiota | 95.54 | 94.16 | 87.37 | 81.40 | 90.83 | 90.48 |
| PKCmu/PRKD1 | 113.86 | 105.64 | 90.68 | 88.67 | 93.35 | 93.19 |
| PKCnu/PRKD3 | 104.21 | 100.90 | 104.98 | 102.96 | 104.52 | 102.17 |
| PKCtheta | 113.89 | 100.22 | 94.74 | 92.16 | 96.88 | 96.03 |
| PKCzeta | 105.39 | 101.79 | 93.62 | 92.76 | 103.63 | 103.55 |
| PKD2/PRKD2 | 94.93 | 92.84 | 102.17 | 98.13 | 95.68 | 95.36 |
| PKG1a | 110.14 | 107.44 | 93.23 | 93.09 | 120.40 | 109.05 |
| PKG1b | 87.55 | 86.19 | 99.99 | 98.34 | 87.31 | 84.74 |
| PKG2/PRKG2 | 100.92 | 97.41 | 100.85 | 99.42 | 100.48 | 96.50 |
| PKMYT1 | 86.96 | 86.80 | 89.61 | 89.25 | | |
| PKN1/PRK1 | 109.51 | 108.34 | 96.50 | 94.16 | 76.85 | 73.93 |
| PKN2/PRK2 | 111.95 | 109.14 | 105.38 | 104.85 | 87.07 | 86.46 |
| PKN3/PRK3 | 92.46 | 91.58 | 76.19 | 74.34 | 98.61 | 97.90 |
| PLK1 | 97.01 | 94.28 | 95.55 | 92.77 | 103.87 | 102.40 |
| PLK2 | 86.05 | 85.33 | 100.13 | 99.51 | 95.21 | 93.24 |
| PLK3 | 96.08 | 93.64 | 96.04 | 95.88 | 101.94 | 100.40 |
| PLK4/SAK | 88.18 | 87.95 | 84.29 | 83.82 | 100.36 | 99.38 |
| PRKX | 103.95 | 102.07 | 91.49 | 88.11 | 87.49 | 79.11 |
| PYK2 | 93.53 | 92.71 | 91.04 | 89.71 | 103.87 | 101.80 |
| RAF1 | 86.96 | 82.02 | 92.48 | 88.10 | 92.60 | 85.53 |
| RET | 97.80 | 95.48 | 98.13 | 98.08 | 113.39 | 110.76 |
| RIPK2 | 120.34 | 113.72 | 80.24 | 75.68 | 89.29 | 87.55 |
| RIPK3 | 100.98 | 98.09 | 97.55 | 92.71 | | |
| RIPK4 | 89.19 | 77.00 | 96.69 | 92.28 | 102.82 | 98.45 |
| RIPK5 | 102.02 | 101.13 | 95.51 | 94.86 | 96.59 | 95.70 |
| ROCK1 | 108.96 | 108.68 | 78.18 | 75.70 | 96.81 | 96.41 |
| ROCK2 | 100.38 | 99.37 | 107.03 | 102.48 | 93.57 | 91.72 |
| RON/MST1R | 108.15 | 94.20 | 99.98 | 96.90 | 96.89 | 88.05 |
| ROS/ROS1 | 102.99 | 101.59 | 85.55 | 85.00 | 102.30 | 102.23 |
| RSK1 | 92.36 | 91.37 | 96.32 | 95.98 | 93.18 | 90.97 |
| RSK2 | 100.61 | 95.11 | 79.87 | 78.52 | 73.04 | 71.41 |
| RSK3 | 102.78 | 102.31 | 90.06 | 89.38 | 100.27 | 94.06 |
| RSK4 | 107.17 | 102.38 | 92.19 | 91.27 | 115.69 | 115.36 |
| SBK1 | 99.08 | 98.84 | 97.70 | 95.71 | 87.45 | 80.58 |
| SGK1 | 93.72 | 92.96 | 95.38 | 91.71 | 115.37 | 114.27 |
| SGK2 | 101.25 | 100.07 | 88.57 | 88.54 | 97.24 | 94.05 |
| SGK3/SGKL | 93.77 | 86.54 | 95.34 | 86.29 | 90.11 | 89.10 |
| SIK1 | 102.09 | 100.71 | 98.34 | 96.55 | 99.79 | 95.43 |
| SIK2 | 97.01 | 96.84 | 95.77 | 95.38 | 89.82 | 88.74 |
| SIK3 | 92.41 | 91.64 | 94.50 | 93.35 | 86.93 | 81.60 |
| SLK/STK2 | 89.71 | 87.93 | 94.99 | 94.62 | 99.70 | 99.11 |
| SNARK/NUAK2 | 99.78 | 97.60 | 97.80 | 95.90 | 111.83 | 111.42 |
| SNRK | 96.83 | 90.60 | 98.76 | 94.52 | 102.32 | 100.60 |
| SRMS | 99.78 | 99.25 | 104.82 | 102.21 | 103.66 | 102.62 |
| SRPK1 | 98.71 | 94.40 | 103.79 | 99.01 | 96.92 | 96.82 |
| SRPK2 | 95.64 | 94.96 | 94.00 | 93.75 | 113.80 | 111.56 |
| SSTK/TSSK6 | 103.45 | 102.43 | 102.90 | 92.58 | 94.01 | 87.61 |
| STK16 | 98.61 | 94.14 | 106.54 | 100.13 | 94.36 | 94.26 |
| STK21/CIT | 90.14 | 87.64 | | | 98.81 | 97.63 |
| STK22D/TSSK1 | 101.70 | 97.48 | 106.56 | 101.81 | 102.88 | 102.11 |
| STK25/YSK1 | 106.06 | 105.80 | 96.11 | 94.22 | 70.55 | 69.19 |
| STK32B/YANK2 | 122.29 | 122.14 | 102.97 | 101.16 | 89.81 | 81.71 |
| STK32C/YANK3 | 113.00 | 105.00 | 90.70 | 85.47 | 112.12 | 111.17 |
| STK33 | 99.34 | 95.39 | 81.81 | 80.29 | 87.62 | 87.51 |
| STK38/NDR1 | 99.16 | 98.55 | 95.53 | 95.29 | 91.50 | 88.33 |
| STK38L/NDR2 | 102.63 | 100.37 | 94.75 | 93.00 | 95.14 | 93.75 |
| STK39/STLK3 | 87.51 | 83.27 | 82.30 | 74.78 | 64.55 | 62.58 |
| SYK | 103.79 | 100.71 | 90.34 | 86.91 | 88.53 | 85.46 |
| TAK1 | 98.00 | 97.75 | 109.47 | 109.41 | 98.42 | 97.70 |

TABLE 1-continued

| | % Enzyme Activity (relative to DMSO controls) | | | | | |
|---|---|---|---|---|---|---|
| | Compound 17 (5 uM) | | Compound 25 (5 uM) | | Compound 27 (10 uM) | |
| Kinase: | Data 1 | Data 2 | Data 1 | Data 2 | Data 1 | Data 2 |
| TAOK1 | 122.31 | 121.33 | 90.64 | 89.61 | 109.94 | 108.33 |
| TAOK2/TAO1 | 101.21 | 101.17 | 88.17 | 84.66 | 93.26 | 88.63 |
| TAOK3/JIK | 103.32 | 102.95 | 90.15 | 88.00 | 97.96 | 94.36 |
| TBK1 | 102.03 | 99.45 | 98.79 | 98.48 | 97.79 | 95.84 |
| TEC | 97.16 | 95.04 | 97.65 | 97.28 | 91.08 | 90.91 |
| TESK1 | 100.67 | 100.49 | 91.00 | 84.69 | 88.70 | 87.96 |
| TESK2 | 93.34 | 91.78 | 80.12 | 78.64 | 99.22 | 97.37 |
| TGFBR2 | 113.33 | 104.08 | 82.58 | 82.14 | 86.85 | 86.82 |
| TIE2/TEK | 100.42 | 97.21 | 105.44 | 104.23 | 86.64 | 85.92 |
| TLK1 | 104.55 | 102.03 | 53.36 | 48.17 | 105.12 | 102.81 |
| TLK2 | 99.08 | 98.73 | 109.31 | 106.34 | 97.16 | 94.14 |
| TNIK | 53.25 | 51.88 | 84.33 | 83.10 | 94.47 | 93.91 |
| TNK1 | 100.42 | 98.27 | 91.54 | 90.74 | 105.21 | 102.24 |
| TRKA | 99.96 | 95.41 | 87.82 | 87.48 | 80.99 | 76.75 |
| TRKB | 84.15 | 83.82 | 91.45 | 88.25 | 92.37 | 82.95 |
| TRKC | 64.31 | 64.04 | 38.61 | 36.52 | 85.97 | 85.08 |
| TSSK2 | 91.55 | 90.03 | 95.14 | 95.11 | 84.68 | 84.23 |
| TSSK3/STK22C | 97.71 | 97.63 | 101.08 | 96.70 | 100.00 | 99.06 |
| TTBK1 | 97.25 | 92.57 | 82.32 | 80.80 | 113.33 | 101.61 |
| TTBK2 | 106.96 | 105.69 | 103.68 | 102.18 | 97.61 | 92.08 |
| TXK | 89.75 | 87.45 | 90.81 | 90.15 | 76.68 | 73.77 |
| TYK1/LTK | 99.18 | 94.47 | 92.19 | 91.35 | 114.12 | 109.99 |
| TYK2 | 95.87 | 91.08 | 89.26 | 88.73 | 114.21 | 109.10 |
| TYRO3/SKY | 75.40 | 75.37 | 68.40 | 65.60 | 98.80 | 96.81 |
| ULK1 | 133.53 | 131.26 | 93.93 | 91.13 | 77.26 | 70.77 |
| ULK2 | 196.10 | 194.58 | 105.22 | 90.15 | 74.92 | 69.83 |
| ULK3 | 111.12 | 103.36 | 76.58 | 74.98 | 105.03 | 99.50 |
| VRK1 | 109.03 | 98.12 | 91.87 | 91.08 | 108.94 | 104.53 |
| VRK2 | 103.33 | 102.70 | 102.23 | 101.89 | 101.73 | 100.17 |
| WEE1 | 124.04 | 121.51 | 85.22 | 72.39 | 97.27 | 91.19 |
| WNK1 | 99.70 | 97.40 | 93.27 | 92.88 | 88.89 | 87.30 |
| WNK2 | 96.35 | 95.59 | 91.94 | 88.67 | 91.10 | 90.51 |
| WNK3 | 99.55 | 96.88 | 91.80 | 87.30 | 102.15 | 100.53 |
| YES/YES1 | 96.53 | 91.46 | 91.00 | 90.52 | 81.42 | 81.19 |
| YSK4/MAP3K19 | 105.00 | 104.03 | 126.35 | 97.32 | 95.47 | 92.17 |
| ZAK/MLTK | 100.61 | 98.53 | 90.44 | 88.52 | 89.88 | 85.41 |
| ZAP70 | 101.56 | 98.40 | 103.97 | 103.52 | 103.24 | 98.81 |
| ZIPK/DAPK3 | 100.30 | 95.77 | 107.76 | 100.23 | 100.51 | 99.46 |

3.1 Crystallization

Purification of JNK3 39-402 and its crystallization with ATP was done following previously published procedures. The JNK3 inhibitor was soaked into JNK3-ATP crystals by adding 1 mM of the compound into the crystallization drop and incubating for 24 hrs. The crystals were then transferred to mounting loops and excess drop solutions were removed and flash frozen by plunging into liquid nitrogen.

3.2 Data Collection and Refinement

Diffraction datasets were collected on Dectris Eiger 9M at the APS beamline 21-ID-D. The datasets were processed with HKL2000 (HKL Research, Inc) and were phased using Phaser (Phenix suite) with PDB ID 1JNK as the search model for molecular replacements. Initial phased map showed positive density for the target compounds in the ATP pocket. Restraints and coordinates for the compounds were generated using eLBOW (Phenix suite) and incorporated into JNK3 coordinate. The models were refined using phenix.refine (Phenix suite). The models were manually inspected and adjusted after each refinement cycle using Coot.

3.3 the Co-Crystal Structure of Compound 17 in Human JNK3

FIG. 1. Shows the transparent sphere and wire model of residues involved in hydrophobic pocket formation. The residues, 170 and A151 sandwich the thiophene ring. V78, A91 (not visible), and V196 VdW contact with pyrazole ring. The residues K93, 1124, L126 and L144 wraps around Cl-phenyl ring. 17 is colored blue and the protein residues are colored grey.

3.4 the Co-Crystal Structure of Compound 17 in Human JNK3

Figure 2:
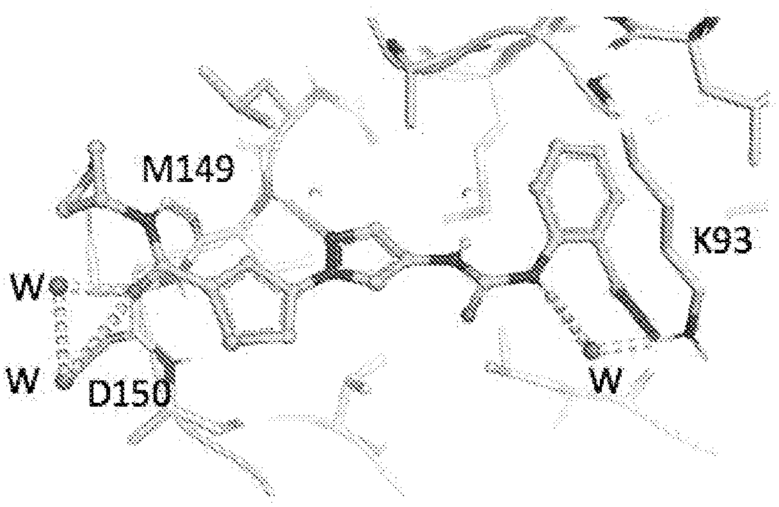
FIG. 2 shows the stick model of residues involved in H-bond/Halogen bond interactions. The hinge residue M149 make two H-bonds. K93 and D150 are involved in water-mediated H-bonds. K93 also makes halogen bond with Cl of Cl-phenyl.

FIG. 2 shows the stick model of residues involved in H-bond/Halogen bond interactions. The hinge residue M149 make two H-bonds. K93 and D150 are involved in water-mediated H-bonds. K93 also makes halogen bond with Cl of Cl-phenyl.

4. Pharmacology Experiment

4.1 Pharmacokinetics

Pharmacokinetics studies were conducted in C57Bl/6J mice. The compound was formulated in a generic formulation at 1 mg/mL (e.g. 10:40:4:46, DMSO:PEG 400: tween 80: PBS, v:v:v:v) or other specified formulations and dosed at 1 mg/kg intravenous into the femoral vein or 1-10 mg/kg by oral gavage, or 5-20 mg ip. Blood was obtained at t=5 min, 15 min, 30 min, 1 hr, 2 hr, 4 hr, 6 hr, and 8 hr. Blood was collected by heart puncture into EDTA containing tubes and plasma was generated by standard centrifugation methods. Brains were collected following perfusion with ice-cold saline, and snap frozen in liquid N2. Both plasma and brains were stored at −80° C. until processing. All procedures and handling were according to standard operating procedures approved by IAPUC at Scripps Florida and/or Ohio State University. In order to assess in vivo pharmacokinetic parameters an LC-MS/MS bioanalytical method was developed where 25 TI of plasma was treated with 125 TI of acetonitrile containing an internal standard in a Millipore Multscreen Slovinter 0.45 micron low binding PTFE hydrophilic filter plate (#MSRLN0450) and allowed to shake at room temperature for five minute. The plate was then centrifuged for 5 minutes at 4000 rpm in a tabletop centrifuge and the filtrate was collected in a polypropylene capture plate. The filtrate (10 TI) is injected using an Agilent 1200 HPLC equipped with a Thermo Betasil C18 HPLC column 5 T (50×2.1 mm) #70105-052130. Mobile Phase A was water with 0.1% formic acid. Mobile phase B was acetonitrile with 0.1% formic acid. Flow rate was 375 TI/min using a gradient of 90% A/10% B from, 0-0.5 min, ramped to 5% A/95% B at 2 min, held at 5% A/95% B until 3.0 min, ramped to 90% A/10% B at 4 min, and held at 90% A/10% B until 7 min. An API Sciex 4000 equipped with a turbo ion spray source was used for all analytical measurement. MRM methods were developed in position ion mode. Peak areas of the analyte ion were measured against the peak areas of the internal standard. Data was fit using WinNonLin using an IV bolus model.

4.2 P450s Inhibition

P450s inhibition for four major isoforms are evaluated using a cocktail inhibition assay where the metabolism of specific marker substrate (CYP1A2 phenaceten demethylation to acetaminophen); CYP2C9, tolbutamide hydroxylation to hydrocytolbutamide; CYP2D6, bufuralol hydroxylation to 4'-Hydroxybufuralol; and CYP3A4, midazolam hydroxylation to 1'-Hydroxymidazolam) in the presence or absence of 10 TM probe compound is evaluated. The concentration of each marker substrate is approximately its Km. Conditions were similar to those described by Tesino and Patonay (Testino, S. A., Jr.; Patonay, G. High-throughput inhibition screening of major human cytochrome P450 enzymes using an in vitro cocktail and liquid chromatography-tandem mass spectrometry. *J Pharm Biomed Anal* 2003, 30, 1459-67) except 2C19 was not evaluated as we found that stock solution of the 2C19 probe substrate, omeprazole, had poor stability. Specific inhibitors for each isoform are included in each run to validate the system.

Results and Discussion

Figure 3:
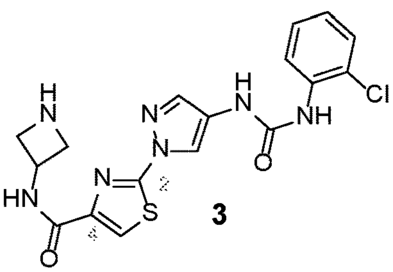
FIG. 3 shows the replacement of the benzamide phenyl ring by a 5-membered aromatic moiety.
Figure 3:
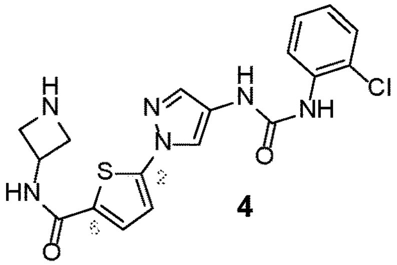
Figure 3:
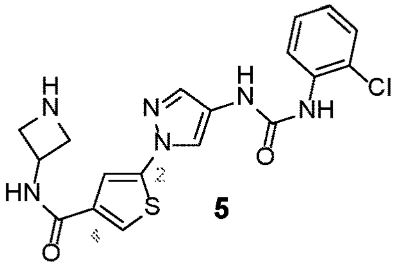
Figure 3:
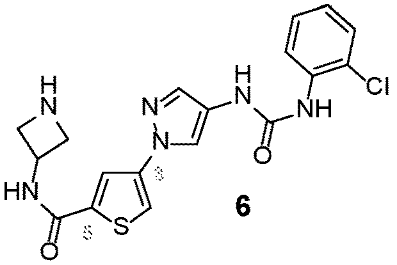

The first step was to replace the phenyl ring in Area-A with a 5-membered aromatic moiety. A thiazole ring was first investigated. As shown in FIG. 3, the thiazole analog 3 showed no inhibition to both JNK3 and JNK1. It was reasoned that the H-bond acceptor nitrogen in the thiazole ring might have disturbed the optimal hinge-binding patterns for the inhibitor to JNK3. Next, non-nitrogen-containing thiophene moieties were investigated. Indeed, much better JNK3 inhibitory activities were observed. The 2,6-disubstitution pattern analog 4 gave a sub-micromolar $IC_{50}$ JNK3 inhibition (0.8 μM) while still keeping a good isoform selectivity against JNK1. Even higher JNK3 inhibition (and isoform selectivity against JNK1) was observed for the 2,4-disubstitution analog 5 ($IC_{50}$: 0.2 μM). The best JNK3 inhibitor was obtained when a 3,5-disubstituted thiophene ring was applied (analog 6), which exhibited a JNK3 inhibition $IC_{50}$ of 0.05 μM and had high isoform selectivity against JNK1 ($IC_{50}$: 3.6 μM, 72-fold selectivity). Moreover, both 5 and 6 had almost no inhibitions to their closely related kinase p38 ($IC_{50}$>20 μM). Therefore, the chemotype incorporating a 3,5-disubstituted thiophene ring (as in 6) will be used for further optimizations.

Next, the amide moiety in compound 6 was varied. As shown in Table 2, various amides were prepared to investigate JNK3 inhibitory potency and isoform selectivity against JNK1 and JNK2 (assessed by the ratio of the $IC_{50}$ value of JNK1 or JNK2 over JNK3). In terms of JNK3 inhibitory activity, simple alkyl amides (7 and 8) resulted in a reduction of JNK3 inhibition compared to the heterocyclic ring-containing amide 6. Replacing the azetidine with an R-configured pyrrolidine (9) also reduced the JNK3 inhibition. N-Methylation to the ring-nitrogen (10) gained some activity. Interestingly, deuteration to the N-methyl group (11) did not affect the activity at all. On the other hand, changing the chirality of the pyrrolidine ring from R to S (12) led to an increase in JNK3 inhibitory activity. Moreover, application of a bulkier N-substitution (13) further increased the JNK3 inhibition. Further increasing the ring size led to a slight decrease in JNK3 inhibition (14 vs 12). However, replacing the ring nitrogen by an oxygen (15) could gain JNK3 inhibitory activity. In addition, replacing the 2H-pyran in 15 by a tetrahydrofuran ring (16) led to a compound with a very high JNK3 inhibitory activity ($IC_{50}$: 8 nM). Further decreasing the ring size by applying an oxetane moiety (17) resulted in some loss of JNK3 inhibitory activity, but the $IC_{50}$ of 17 was still comparable to or slightly better than that of lead 6. Interestingly, -methyl substitution to the oxetane ring (18) did not significantly affect the JNK3 inhibition. Insertion of a methylene group between the heterocyclic ring and the amine moiety (compounds 19 to 24) led to deteriorated JNK3 inhibitors. Generally, these compounds had lower JNK3 inhibitions as compared to their corresponding analogs, such as 19 vs 14, 21 vs 12, and 22 vs 16. The only exception is compound 24. Its $IC_{50}$ value was about half that of its corresponding analog 15.

TABLE 2
SAR studies for the amide moiety.
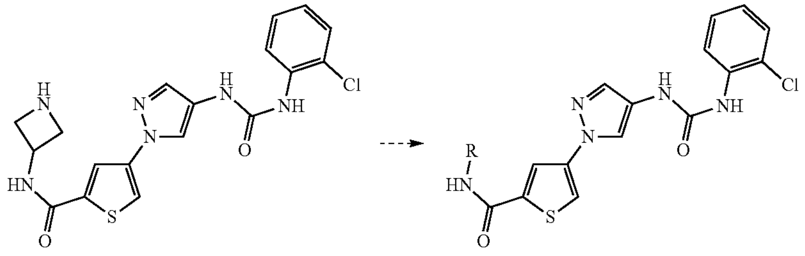
6 7-24
| | | Biochemical inhibition $IC_{50}$ (µM)[a] | | | |
|---|---|---|---|---|---|
| cmpd | R | JNK3 | JNK1 (R)* | JNK2 (R)* | p38α |
| 6 | 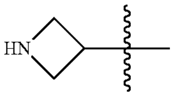 [SMILES: *C1CNC1] | 0.05 | 3.6 (72) | nd[b] | >20 |
| 7 | Me | 0.118 | >20 (>100) | nd[b] | >20 |
| 8 | 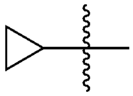 [SMILES: *C1CC1] | 0.08 | 7.4 (93) | 3.20 (40) | >20 |
| 9 | 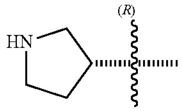 | 0.132 | 5.9 (45) | nd[b] | >20 |
| 10 | 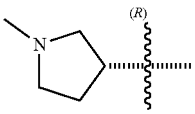 | 0.085 | 5.1 (60) | nd[b] | >20 |
| 11 | 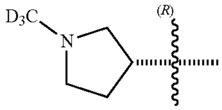 | 0.083 | 5.1 (61) | nd[b] | >20 |
| 12 | 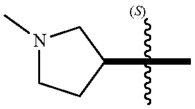 | 0.039 | 2.2 (56) | 1.51 (39) | >20 |
| 13 | 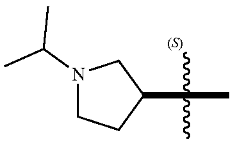 | 0.012 | 0.72 (60) | nd[b] | >20 |
| 14 | 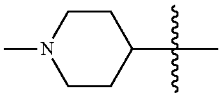 | 0.084 | 4.2 (50) | 2.77 (33) | >20 |
| 15 | 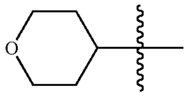 [SMILES: *C1CCOCC1] | 0.05 | 1.9 (38) | 1.05 (21) | >20 |

TABLE 2-continued
SAR studies for the amide moiety.
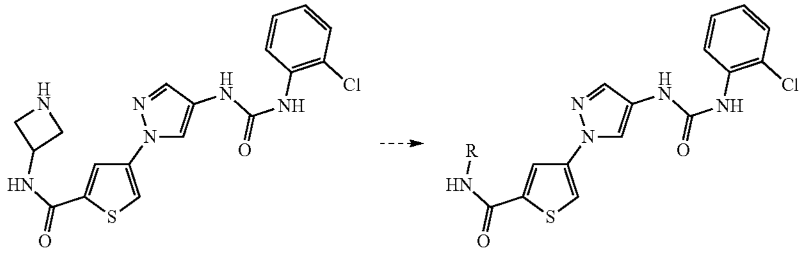
6 7-24
| cmpd | R | Biochemical inhibition $IC_{50}$ (μM)[a] | | | |
|---|---|---|---|---|---|
| | | JNK3 | JNK1 (R)* | JNK2 (R)* | p38α |
| 16 | 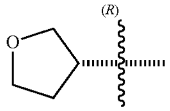 | 0.008 | 1.5 (188) | 2.02 (253) | >20 |
| 17 | 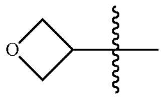 [SMILES: *C1COC1] | 0.035 | 5.9 (170) | 1.36 (39) | >20 |
| 18 | 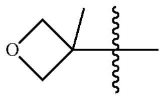 [SMILES: *C1(C)COC1] | 0.045 | 3.3 (73) | nd[b] | >20 |
| 19 | 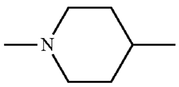 | 0.142 | 5.8 (41) | nd[b] | >20 |
| 20 | 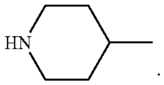 | 0.186 | 6.6 (35) | nd[c] | >20 |
| 21 | 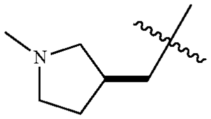 [SMILES: *C[C@H]1CCN(C)C1] | 0.222 | 10.3 (46) | nd[c] | >20 |
| 22 | 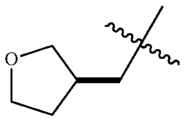 [SMILES: *C[C@H]1CCOC1] | 0.071 | 2.2 (31) | nd[c] | >20 |
| 23 | 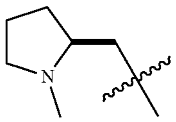 [SMILES: *C[C@@H]1CCCN1C] | 0.085 | 9.1 (107) | nd[c] | >20 |
| 24 | 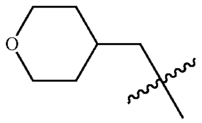 [SMILES: *CC1CCOCC1] | 0.024 | 1.5 (63) | 0.81 (34) | >20 |
[a]IC50 values are the mean of ≥2 experiments with errors within 30% of the mean.
[b]Not determined.
*R: ratio of $IC_{50}$ values of JNK1 over JNK3 or JNK2 over JNK3.

Similar to lead inhibitors 5 and 6, the $IC_{50}$ values against p38a for compounds listed in Table 2 were all greater than 20 M, indicating a generally excellent selectivity of this pyrazole-urea based scaffold against kinase p38a (the selectivity for most compounds is >100-fold). In terms of the isoform selectivity against JNK1, some compounds showed a fair selectivity (R value between 20 to 50), such as compounds 9, 14, 15, 19-22; many compounds exhibited a good selectivity (R value between 50-100), such as compounds 6, 8, 10-14, 18, and 24; and a few compounds demonstrated an excellent selectivity (R value greater than 100), such as compounds 7, 16, 17, and 23. In summary, amides with a nitrogen-containing heterocyclic ring gave lower selectivity, and amides with a methylene moiety inserted between the heterocycle and the amino group exhibited worse isoform selectivity against JNK1. The rationales for isoform selectivity of JNK3 over JNK1 have been elucidated in our previous publications.[26]

In previous studies, we demonstrated that, by crystallography and sequence residue mutation studies, isoform selectivity against JNK2 is not easy to achieve.[26] Nevertheless, fair to excellent isoform selectivity against JNK2 in some of THE compounds was observed. For example (Table 2), compounds 14, 15, and 24 all had a JNK2 $IC_{50}$ value in the μM range and gave an isoform selectivity vs JNK3 between 20-30 folds. Compounds 8, 12, and 17 exhibited an even better selectivity of around 40-folds. An exceptional high isoform selectivity was observed for compound 16, which is >250-folds. Although the residues inside and around the binding pockets are almost identical, it is believed that the sequence difference between JNK2 and JNK3 can still yield different sizes and shapes for their binding pockets, and that might be the reasons for the observed isoform selectivity of JNK3 against JNK2 for some of the compounds.

In order to identify the compounds for further investigation, in vitro DMPK and cytotoxicity assays were performed to evaluate selected compounds in Table 2. As shown in Table 3, these JNK3 inhibitors were clean in CYPs inhibitions and they exhibited low inhibitory activities against the four select P450 isozymes. Stabilities in human and mouse microsomes were also fair to good for most compounds listed in Table 2. In human microsome, amides with a nitrogen-containing heterocyclic ring gave better stability than those compounds with an oxygen-containing heterocyclic ring (12/14 vs 15/16). Interestingly, opposite trend was observed in cytotoxicity assays; compounds with an oxygen-containing hetero-cyclic ring demonstrated lower toxicity than compounds with a nitrogen-containing heterocyclic ring (16/17 vs 12/14). Although compound 24 was very potent for JNK3 and had isoform selectivity, it had serious liability in human microsomal stability. Therefore, based on overall consideration of JNK3 inhibitory potency, isoform selectivity (against JNK1/JNK2), in vitro DMPK properties, and cytotoxicity, compounds 16 and 17 were selected as new leads for further optimizations.

TABLE 3

Data for P450 inhibition, microsomal stability, and MTT cytotoxicity assays for selected JNK3 inhibitors.

| cmpd | CYP-450 % inh.[a] 1A2/2C9/2D6/3A4 | Mic. stability $t_{1/2}$ (min) Human | Mic. stability $t_{1/2}$ (min) Mouse | MTT cell viability at 10M[b] |
|---|---|---|---|---|
| 8 | −2/−4/−29/−45 | 49 | 35 | 103% |
| 12 | −1/−9/20/−18 | 54 | 20 | 94% |
| 14 | −6/−19/−5/−34 | 92 | 15 | 89% |
| 15 | 32/7/0/−35 | 32 | 16 | 97% |
| 16 | 17/38/1/−20 | 33 | 13 | 112% |
| 17 | 6/8/−15/−34 | 66 | 24 | 104% |
| 24 | 36/64/32/21 | 8 | 15 | 95% |

TABLE 3-continued

[a]% inh. at 10 μM.

[b]Data were the average of ≥2 experiments performed in SHSY5Y cells.

F-substitution of compounds 16 and 17 was next investigated. This extra F-substitution is expected to stabilize the aniline moiety, thus could lead to improved DMPK properties. In addition, the electron-withdrawing character of a F-substituent might also be able to reduce the potential metabolic toxicities associated with anilines.

As shown below, the 6-F substituted analog 25 gave a similar JNK3 inhibitory potency while the 4-F substituted analog 26 exhibited a slightly lower potency as compared to lead 17. Performing α-methylation to the thiophene ring of 25 resulted in a compound (27) which had also a slightly reduced JNK3 inhibitory potency. On the other hand, applications of both a 6-F substitution and an α-methylation (on the thiophene ring) to 16 resulted in a compound (28) which had a 7-fold reduction in JNK3 inhibitions. It is important to point out that new compounds incorporating these structural modifications still had high selectivity against p38a and still kept a high isoform selectivity against JNK1 (all >100-folds) and JNK2.

25

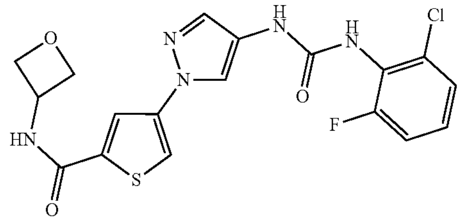

Kinase inh. $IC_{50}$
JNK3: 0.033 μM
JNK1: 4.9 μM
JNK2: 2.0 μM
p38[α]: >20 μM

26

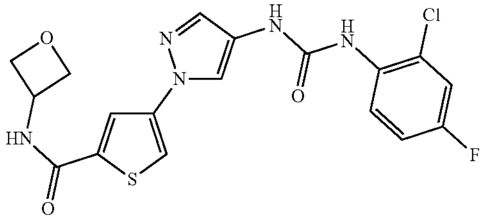

Kinase inh. $IC_{50}$
JNK3: 0.053 μM
JNK1: >10 μM
JNK2: >10 μM
p38[α]: >20 μM

-continued

27

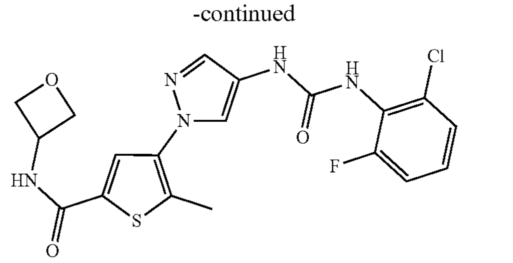

Kinase inh. $IC_{50}$
JNK3: 0.067 μM
JNK1: 8.3 μM
JNK2: 0.15 μM
$p38^{\alpha}$: >20 μM

28

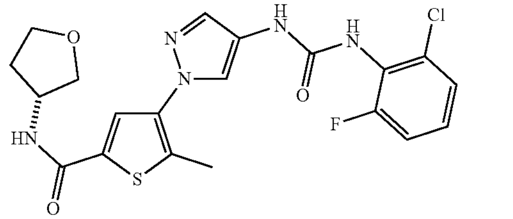

Kinase inh. $IC_{50}$
JNK3: 0.053 μM
JNK1: 7.3 μM
JNK2: 2.7 μM
$p38^{\alpha}$: >20 μM As shown in Table 4, the fluorinated analogs were also clean in CYPs inhibitions, and their cytotoxicity were still low at 10 μM. As expected, the microsomal stabilities (in both human and mouse microsomes) were much higher as compared to leads 16 and 17. Interestingly, α-methylation to the thiophene ring resulted in a lower microsomal stability in mice (27 vs 25).

TABLE 4

Data for P450 inhibition, microsomal stability, and MTT cytotoxicity assays for optimized JNK3 inhibitors.

| | CYP-450 % inh.[a] | Mic. stability $t_{1/2}$ (min) | | MTT cell viability at |
|---|---|---|---|---|
| cmpd | 1A2/2C9/2D6/3A4 | Human | Mouse | 10M[b] |
| 25 | 36/48/31/24 | 100 | 72 | 102% |
| 26 | 38/47/30/−5 | >120 | 68 | 104% |
| 27 | 22/33/1/16 | 110 | 57 | 111% |
| 28 | 34/35/17/26 | 40 | 38 | 114% |

[a]% inh. at 10 μM.
[b]Data were the average of ≥2 experiments performed in SHSY5Y cells.

Kinase panel profiling studies were applied to evaluate the general selectivity of lead JNK3 inhibitors. Thus, 17 at 5 μM, 25 at 5 μM, and 27 at 10 μM (the profiling concentration was set to be >100-fold of the JNK3 $IC_{50}$ value of each compound) were subjected to profiling studies against a panel of ~374 wild-type kinases (Reaction Biology Corporation, www.reactionbiology.com). Table 1 showed that all three compounds had significant inhibition (>80% inhibition) against only JNK3 at the profiled concentrations. These results demonstrated that JNK3 inhibitors derived from this thiophenyl-pyrazolourea scaffold had not only isoform selectivity (vs. JNK1/2) but also a broadly high selectivity against other kinases.

Figure 4:
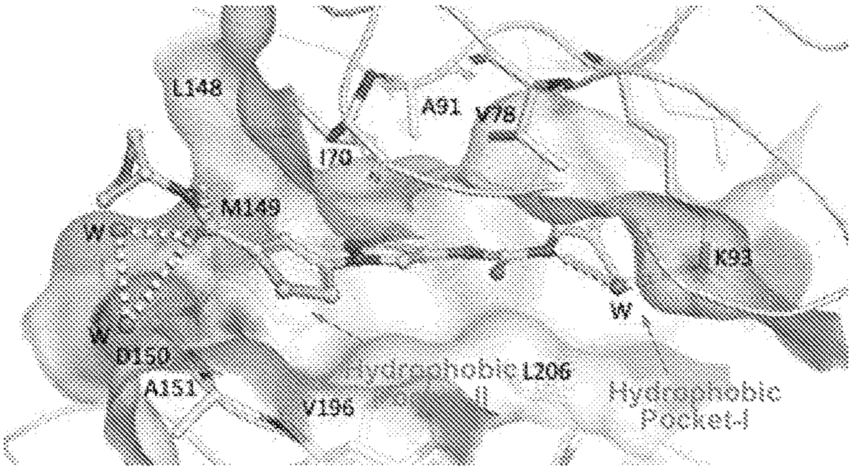
FIG. 4 shows the overlay X-ray crystal structure of inhibitor 17 in human JNK3 (2.0 Å).

Crystallography studies were applied to reveal rationales for the favored JNK3 inhibition of this thiophenyl pyrazolourea chemotype. Thus, co-crystal structures of inhibitors 17 and 27 (shown in the TOC Graphic) with human JNK3 were pursued. The 2.0 Å crystal structure of 17 (FIG. 4) showed that, in the ATP-binding pocket, the pyrazole nitrogen atom and the amide NH moiety H-bound to hinge residue M149 of JNK3. Another key H-bonding interaction from this mode was the water-bridged H-bonds between the aniline-urea NH and the side-chain NH2 of residue K93. Water-bridged H-bonds were also observed for the amide carbonyl group with near-by protein residues. The amide heterocyclic ring pointed to the outside of the binding pocket, and toward the solvent. The urea-aniline moiety bound to hydrophobic pocket-I (the selectivity pocket), which is mainly responsible for the isoform selectivity against JNK1. The thiophenyl moiety positioned around hydrophobic pocket-II and its aromatic ring was a little twisted (~30°) with the central pyrazole ring. Hydrophobic interactions in both hydrophobic pocket-I and hydrophobic pocket-II and that around the pyrazole ring all contributed to the high JNK3 affinity.

Figures 5A, 5B, 5C:
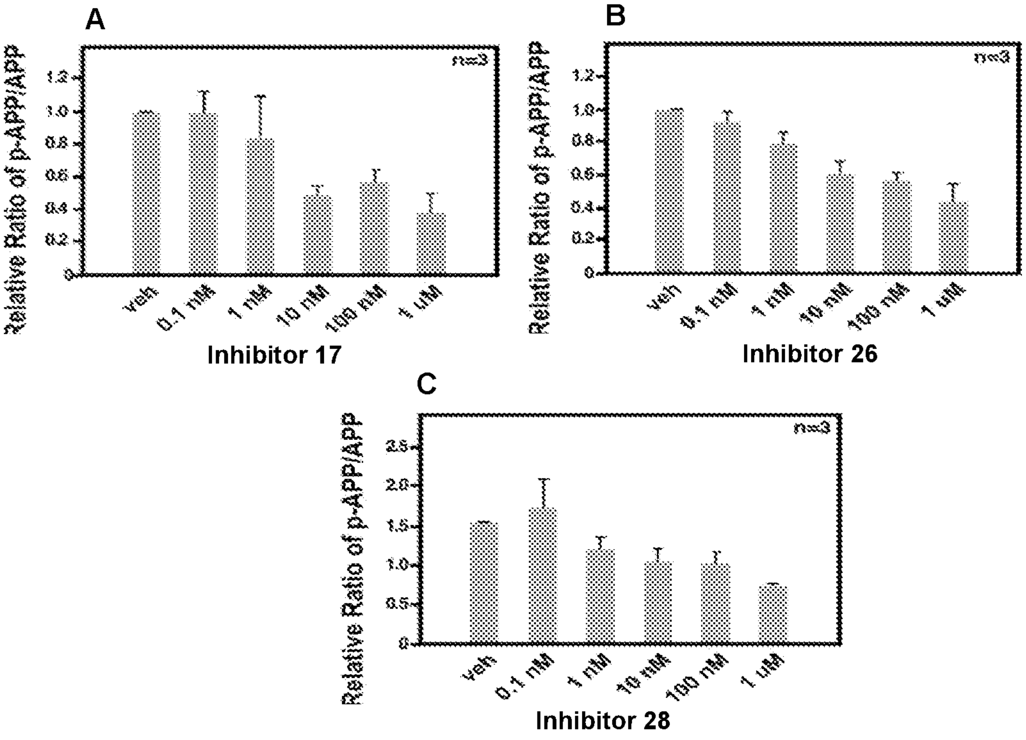
FIGS. 5A-5C show the cell-based inhibition of $APP^{T668}$ phosphorylation in the presence or absence of JNK3 inhibitors: (5A) inhibitor 17, (5B) inhibitor 26, and (5C) inhibitor 28.

It was previously reported that, JNK3 phosphorylates APP, facilitates its rapid endocytosis and processing, producing Aβ42.[4] Aβ42 then activates AMP-activated protein kinase (AMPK) in neurons, which inhibits the mTOR translational pathway by phosphorylating Raptor. This translational block leads to ER stress, which activates JNK3 again, forming a positive feedback loop that accelerates Aβ42 production. To assess the feasibility of applying our newly developed JNK3 inhibitors to reduce and/or to slow down this process, the cell-based inhibition capability of selected compounds on the phosphorylation of $APP^{T668}$ was investigated. As shown in FIGS. 5A-5C, JNK3 inhibitors 17, 26, and 28 significantly inhibited the phosphorylation of residue T668 of APP, even at a concentration of as low as 10 nM.

Finally, in vivo brain exposure experiments were performed for compound 17 in mice to assess the oral bioavailability and brain penetration capability of lead JNK3 inhibitors. As shown in Table 5, po dosing for compound 17 exhibited significant brain presence of the JNK3 inhibitor, indicating 17 is brain penetrant and has oral bioavailability.

TABLE 5

Brain concentration of inhibitors 17 and 27 in mice[a]

| Cmpd (dosing) | Plasma Concentration | Brain Concentration |
|---|---|---|
| 17 (po, 10 mg/kg) | 0.96 μM | 1.08 μM |

In summary, a class of highly selective (including isoform selectivity) and potent JNK3 inhibitors based on a thiophenyl pyrazolourea chemotype has been developed. The inhibitors had significant inhibition to only JNK3 in a panel of 374 wild-type kinases, and were potent in inhibiting the phosphorylation of $APP^{T668}$ of primary cortical and hippocampal neurons. In addition, the optimized JNK3 inhibitors had good in vitro and in vivo DMPK properties, and more importantly, had oral bioavailability and were brain penetrant, which are important for CNS applications.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

REFERENCES

1. Derijard, B.; Hibi, M.; Wu, I. H.; Barrett, T.; Su, B.; Deng, T. L.; Karin, M.; Davis, R. J. Jnk1—a Protein-Kinase Stimulated by Uv-Light and Ha-Ras That Binds and Phosphorylates the C-Jun Activation Domain. *Cell* 1994, 76, 1025-1037.
2. Gupta, S.; Barrett, T.; Whitmarsh, A. J.; Cavanagh, J.; Sluss, H. K.; Derijard, B.; Davis, R. J. Selective interaction of JNK protein kinase isoforms with transcription factors. *Embo. J.* 1996, 15, 2760-2770.
3. Zhang, H.; Shi, X. Q.; Zhang, Q. J.; Hampong, M.; Paddon, H.; Wahyuningsih, D.; Pelech, S. Nocodazole-induced p53-dependent c-Jun N-terminal kinase activation reduces apoptosis in human colon carcinoma HCT116 cells. *Journal of Biological Chemistry* 2002, 277, 43648-43658.
4. Yoon, S. O.; Park, D. J.; Ryu, J. C.; Ozer, H. G.; Tep, C.; Shin, Y. J.; Lim, T. H.; Pastorino, L.; Kunwar, A. J.; Walton, J. C.; Nagahara, A. H.; Lu, K. P.; Nelson, R. J.; Tuszynski, M. H.; Huang, K. JNK3 perpetuates metabolic stress induced by Abeta peptides. *Neuron* 2012, 75, 824-37.
5. Wang, D.; Fei, Z.; Luo, S.; Wang, H. MiR-335-5p Inhibits beta-Amyloid (Abeta) Accumulation to Attenuate Cognitive Deficits Through Targeting c-jun-N-terminal Kinase 3 in Alzheimer's Disease. *Curr Neurovasc Res* 2020, 17, 93-101.
6. Morishima, Y.; Gotoh, Y.; Zieg, J.; Barrett, T.; Takano, H.; Flavell, R.; Davis, R. J.; Shirasaki, Y.; Greenberg, M. E. beta-amyloid induces neuronal apoptosis via a mechanism that involves the c-Jun N-terminal kinase pathway and the induction of Fas ligand. *Journal of Neuroscience* 2001, 21, 7551-7560.
7. Gourmaud, S.; Paquet, C.; Dumurgier, J.; Pace, C.; Bouras, C.; Gray, F.; Laplanche, J. L.; Meurs, E. F.; Mouton-Liger, F.; Hugon, J. Increased levels of cerebrospinal fluid JNK3 associated with amyloid pathology: links to cognitive decline. *J Psychiatry Neurosci* 2015, 40, 151-61.
8. Crocker, C. E.; Khan, S.; Cameron, M. D.; Robertson, H. A.; Robertson, G. S.; LoGrasso, P. JNK Inhibition Protects Dopamine Neurons and Provides Behavioral Improvement in a Rat 6-Hydroxydopamine Model of Parkinson's Disease. *ACS Chem. Neurosci.* 2011, 2, 207-212.
9. Hunot, S.; Vila, M.; Teismann, P.; Davis, R. J.; Hirsch, E. C.; Przedborski, S.; Rakic, P.; Flavell, R. A. JNK-mediated induction of cyclooxygenase 2 is required for neurodegeneration in a mouse model of Parkinson's disease. *Proc Natl Acad Sci USA* 2004, 101, 665-70.
10. Ries, V.; Silva, R. M.; Oo, T. F.; Cheng, H. C.; Rzhetskaya, M.; Kholodilov, N.; Flavell, R. A.; Kuan, C. Y.; Rakic, P.; Burke, R. E. JNK2 and JNK3 combined are essential for apoptosis in dopamine neurons of the substantia nigra, but are not required for axon degeneration. *J Neurochem* 2008, 107, 1578-88.
11. Morfini, G. A.; You, Y. M.; Pollema, S. L.; Kaminska, A.; Liu, K.; Yoshioka, K.; Bjorkblom, B.; Coffey, E. T.; Bagnato, C.; Han, D.; Huang, C. F.; Banker, G.; Pigino, G.; Brady, S. T. Pathogenic huntingtin inhibits fast axonal transport by activating JNK3 and phosphorylating kinesin. *Nat Neurosci* 2009, 12, 864-71.
12. Yang, D. D.; Kuan, C. Y.; Whitmarsh, A. J.; Rincon, M.; Zheng, T. S.; Davis, R. J.; Rakic, P.; Flavell, R. A. Absence of excitotoxicity-induced apoptosis in the hippocampus of mice lacking the Jnk3 gene. *Nature* 1997, 389, 865-870.
13. Kuan, C. Y.; Whitmarsh, A. J.; Yang, D. D.; Liao, G.; Schloemer, A. J.; Dong, C.; Bao, J.; Banasiak, K. J.; Haddad, G. G.; Flavell, R. A.; Davis, R. J.; Rakic, P. A critical role of neural-specific JNK3 for ischemic apoptosis. *Proc Natl Acad Sci USA* 2003, 100, 15184-9.
14. de Lemos, L.; Junyent, F.; Verdaguer, E.; Folch, J.; Romero, R.; Pallas, M.; Ferrer, I.; Auladell, C.; Camins, A. Differences in activation of ERK1/2 and p38 kinase in Jnk3 null mice following KA treatment. *J Neurochem* 2010, 114, 1315-22.
15. Genabai, N. K.; Ahmad, S.; Zhang, Z.; Jiang, X.; Gabaldon, C. A.; Gangwani, L. Genetic inhibition of JNK3 ameliorates spinal muscular atrophy. *Hum Mol Genet* 2015, 24, 6986-7004.
16. Zheng, K.; Iqbal, S.; Hernandez, P.; Park, H.; LoGrasso, P. V.; Feng, Y. Design and synthesis of highly potent and isoform selective JNK3 inhibitors: SAR studies on aminopyrazole derivatives. *J Med Chem* 2014, 57, 10013-30.
17. Zheng, K. Pyridopyrimidinone Derivatives as Potent and Selective c-Jun N-Terminal Kinase (JNK) Inhibitors. 2015, 6, 413-8.
18. Graczyk, P. P.; Khan, A.; Bhatia, G. S.; Palmer, V.; Medland, D.; Numata, H.; Oinuma, H.; Catchick, J.; Dunne, A.; Ellis, M.; Smales, C.; Whitfield, J.; Neame, S. J.; Shah, B.; Wilton, D.; Morgan, L.; Patel, T.; Chung, R.; Desmond, H.; Staddon, J. M.; Sato, N.; Inoue, A. The neuroprotective action of JNK3 inhibitors based on the 6,7-dihydro-5H-pyrrolo[1,2-a]imidazole scaffold. *Bioorg Med Chem Lett* 2005, 15, 4666-70.
19. Jung, H.; Aman, W.; Hah, J. M. Novel scaffold evolution through combinatorial 3D-QSAR model studies of two types of JNK3 inhibitors. *Bioorg Med Chem Lett* 2017, 27, 2139-2143.
20. Tuffaha, G. O.; Hatmal, M. M.; Taha, M. O. Discovery of new JNK3 inhibitory chemotypes via QSAR-Guided selection of docking-based pharmacophores and comparison with other structure-based pharmacophore modeling methods. *J Mol Graph Model* 2019, 91, 30-51.
21. Zhang, T.; Inesta-Vaquera, F.; Niepel, M.; Zhang, J.; Ficarro, S. B.; Machleidt, T.; Xie, T.; Marto, J. A.; Kim, N.; Sim, T.; Laughlin, J. D.; Park, H.; LoGrasso, P. V.; Patricelli, M.; Nomanbhoy, T. K.; Sorger, P. K.; Alessi, D. R.; Gray, N. S. Discovery of potent and selective covalent inhibitors of JNK. *Chem. Biol.* 2012, 19, 140-154.
22. Dou, X.; Huang, H.; Li, Y.; Jiang, L.; Wang, Y.; Jin, H.; Jiao, N.; Zhang, L.; Zhang, L.; Liu, Z. Multistage Screening Reveals 3-Substituted Indolin-2-one Derivatives as Novel and Isoform-Selective c-Jun N-terminal Kinase 3 (JNK3) Inhibitors: Implications to Drug Discovery for Potential Treatment of Neurodegenerative Diseases. *J Med Chem* 2019, 62, 6645-6664.
23. Dou, X.; Huang, H.; Jiang, L.; Zhu, G.; Jin, H.; Jiao, N.; Zhang, L.; Liu, Z.; Zhang, L. Rational modification, synthesis and biological evaluation of 3,4-dihydroquinoxalin-2(1H)-one derivatives as potent and selective c-Jun N-terminal kinase 3 (JNK3) inhibitors. *Eur J Med Chem* 2020, 201, 112445.
24. Oh, Y.; Jang, M.; Cho, H.; Yang, S.; Im, D.; Moon, H.; Hah, J. M. Discovery of 3-alkyl-5-aryl-1-pyrimidyl-1H-pyrazole derivatives as a novel selective inhibitor scaffold of JNK3. *J Enzyme Inhib Med Chem* 2020, 35, 372-376.

25. Manning, A. M.; Davis, R. J. Targeting JNK for therapeutic benefit: From JuNK to gold? *Nature Reviews Drug Discovery* 2003, 2, 554-565.

26. Park, H.; Iqbal, S.; Hernandez, P.; Mora, R.; Zheng, K.; Feng, Y.; LoGrasso, P. Structural Basis for JNK2/3 Isoform Selective Aminopyrazoles. *Sci. Rep.* 2015, 5:8047.

What is claimed is:

1. A compound having a structure represented by a formula:

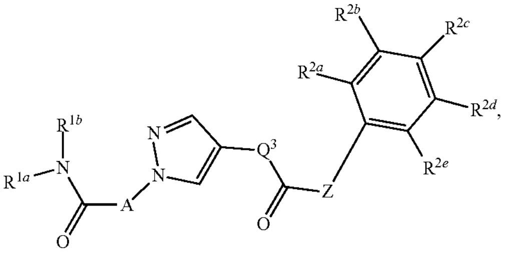

wherein each of $R^{1a}$ and $R^{1b}$ are independently selected from hydrogen, C1-C8 nitrile, C1-C8 alkyl, C1-C8 alkoxy, C1-C8 haloalkyl, C3-C8 cycloalkyl, C3-C8 heterocyclyl, heteroaryl, and aryl;

wherein each of $R^{2a}$, $R^{2b}$, $R^{2c}$, $R^{2d}$, and $R^{2e}$ are independently selected from hydrogen, halo, hydroxy, nitro, azido, —$SF_5$, C1-C3 alkyl, C1-C3 haloalkyl, C1-C3 alkoxy, C1-C3 aminoalkyl, C1-C3 hydroxyalkyl, and —(C1-C3 alkanediyl)-$NR^{5a}R^{5b}$;

wherein each occurrence of $R^{5a}$ and $R^{5b}$ is independently selected from hydrogen, C1-C3 alkyl, C3-C8 cycloalkyl, C3-C8 heterocycloalkyl, aryl and heteroaryl;

wherein A is a structure represented by a formula:

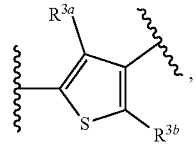, 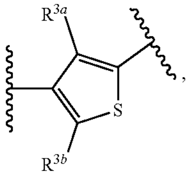, or

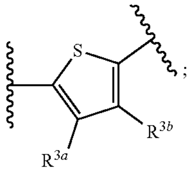;

wherein each of $R^{3a}$ and $R^{3b}$ is selected from hydrogen, halo, hydroxy, nitro, amino, azido, —$SF_5$, C1-C3 alkyl, C1-C3 haloalkyl, C1-C3 alkoxy, C1-C3 aminoalkyl, and C1-C3 hydroxyalkyl;

wherein $Q^3$ is $NR^{4c}$, $CR^{4c}$, or O;

wherein $R^{4c}$ is selected from hydrogen, halo, hydroxy, nitro, azido, —$SF_5$, C1-C3 alkyl, C1-C3 haloalkyl, C1-C3 alkoxy, C1-C3 aminoalkyl, C1-C3 hydroxyalkyl, and —(C0-C3 alkanediyl)-$NR^{5a}R^{5b}$;

wherein Z is selected from —O—, —S—, and —$NR^6$—;

wherein $R^6$ is selected from hydrogen and C1-C3 alkyl;

or a pharmaceutically acceptable salt thereof.

2. The compound of claim 1, having a structure represented by a formula:

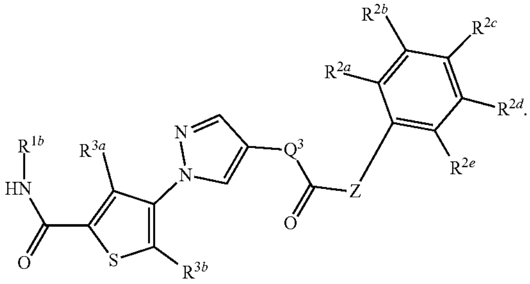

3. The compound of claim 1, wherein Z is —O— or —NH— and $Q^3$ is —O— or —NH—.

4. The compound of claim 1, wherein Z and $Q^3$ are —NH—.

5. The compound of claim 1, wherein $R^{2b}$, $R^{2c}$, and $R^{2d}$ are hydrogen and $R^{2a}$ is selected from —Cl and —F.

6. The compound of claim 5, wherein $R^{2a}$ is halo and $R^{2e}$ is hydrogen.

7. The compound of claim 1, wherein $R^{2a}$ is —Cl and at least one of $R^{2b}$, $R^{2c}$, $R^{2d}$, and $R^{2e}$ is —F.

8. The compound of claim 1, wherein R1b is selected from C1-C8 alkyl, C1-C8 haloalkyl, C1-C8 alkoxy, C3-C8 cycloalkyl, C3-C8 heterocyclyl, and heteroaryl.

9. The compound of claim 1, wherein $R^{1a}$ is hydrogen.

10. The compound of claim 1, wherein $R^{3a}$ is hydrogen.

11. The compound of claim 1, wherein $R^{3a}$ and $R^{3b}$ are hydrogen or C1-C3 alkyl.

12. The compound of claim 1, having a structure represented by a formula:

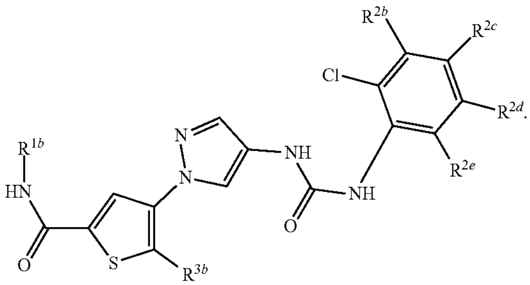

13. The compound of claim 12, wherein $R^{3b}$ is hydrogen or C3-C6 heterocyclyl.

14. The compound of claim 12, wherein at least one of $R^{2b}$, $R^{2c}$, $R^{2d}$, and $R^{2e}$ is —F.

15. The compound of claim 12, wherein $R^{1b}$ is C3-C6 heterocyclyl.

16. The compound of claim 12, wherein $R^{1b}$ is

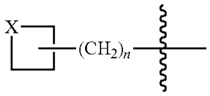, 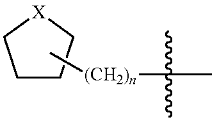, or

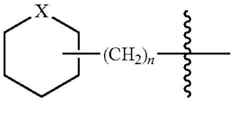;

wherein X is O or $NR^7$, wherein R7 is hydrogen or C1-C8 alkyl, and n is an integer from 0 to 5.
17. The compound of claim 12, wherein $R^{1b}$ is
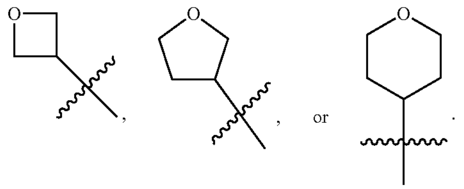 [SMILES: *C1COC1 ; *C1CCOC1 ; *C1CCOCC1]
18. The compound of claim 1, wherein the compound is
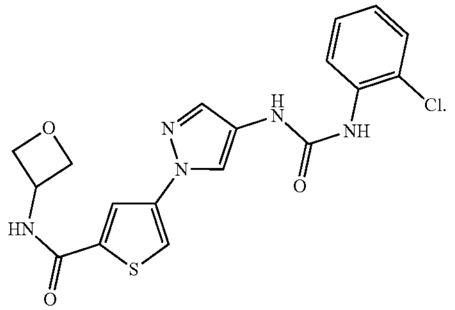 [SMILES: O=C(Nc1cnn(-c2csc(C(=O)NC3COC3)c2)c1)Nc1ccccc1Cl]
19. The compound of claim 1, wherein the compound is a pharmaceutically acceptable salt thereof.
* * * * *